US007943745B2

(12) United States Patent
Tahara et al.

(10) Patent No.: US 7,943,745 B2
(45) Date of Patent: May 17, 2011

(54) ANTI-CD98 ANTIBODY

(75) Inventors: Tomoyuki Tahara, San Diego, CA (US); Yoshikatsu Kanai, Suita (JP); Hitoshi Endou, Tokyo-to (JP); Shiro Kataoka, Tokyo-to (JP); Kazumasa Hasegawa, Takasaki (JP); Tetsuya Yoshino, Takasaki (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 161 days.

(21) Appl. No.: 12/295,991

(22) PCT Filed: Apr. 5, 2007

(86) PCT No.: PCT/JP2007/057680
§ 371 (c)(1),
(2), (4) Date: Oct. 17, 2008

(87) PCT Pub. No.: WO2007/114496
PCT Pub. Date: Oct. 11, 2007

(65) Prior Publication Data
US 2010/0143367 A1    Jun. 10, 2010

(30) Foreign Application Priority Data
Apr. 6, 2006    (JP) ................................. 2006-105013

(51) Int. Cl.
*C12P 21/08* (2006.01)
*C12P 21/04* (2006.01)
*C07K 16/00* (2006.01)
*C07K 17/00* (2006.01)
*C07K 17/14* (2006.01)
*A61K 39/395* (2006.01)
*A61K 39/00* (2006.01)

(52) U.S. Cl. .......... 530/388.15; 530/388.1; 530/388.25; 530/391.1; 424/130.1; 424/142.1; 424/178.1; 435/69.6

(58) Field of Classification Search .................. None
See application file for complete search history.

(56) References Cited

U.S. PATENT DOCUMENTS

| 7,326,414 B2 * | 2/2008 | Bedian et al. .............. 424/141.1 |
| 7,498,420 B2 * | 3/2009 | Michaud et al. .......... 530/388.15 |

FOREIGN PATENT DOCUMENTS

| EP | 1 111 048 A2 | 6/2001 |
| JP | 2000-157286 | 6/2000 |
| WO | WO 02/43478 A2 | 6/2002 |
| WO | WO 03/001884 A2 | 1/2003 |
| WO | WO 2004/035607 A2 | 4/2004 |
| WO | WO 2008/017828 A2 | 2/2008 |

OTHER PUBLICATIONS

Burgess, Shaheen, Ravera, Jaye, Donohue, and Winkles. Possible dissociation of the heparin-binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1452.*
Rudikoff, Giusti, Cook and Scharff. Single amino acid substitution altering antigen-binding specificity. Proceedings of the National Academy of Sciences, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an anti-ErbB2 antibody obtained by shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Schwartz, G.P., Burke, G.T., and Katsoyannis, P.G. A superactive insulin: [B10-Aspartic acid]insulin (human). Proceedings of the National Academy of Sciences, 1987. vol. 84, pp. 6408-6411.*
Lin, M.C., Wright, D.E., Hruby, V.J., and Rodbell, M. Structure-function relationships in glucagon: properties of highly purified Des-His1- Monoiodo-, and [Des-Asn28, Thr29](homoserine lactone27)glucagon. Biochemistry, 1975. vol. 14, pp. 1559-1563.*

(Continued)

*Primary Examiner* — Anne M. Gussow
(74) *Attorney, Agent, or Firm* — Stephen A. Bent; Foley & Lardner LLP

(57) ABSTRACT

A human antibody or a functional fragment thereof having specific binding ability to CD98 which is derived from the cell membrane of cancer cells and is in the form of a complex with a protein having an amino acid transporter activity (for example, LAT1) is disclosed. This antibody binds to CD98 in the form of a dimer with LAT1 on the surface of cancer cells, specifically attacks cancer cells expressing CD98 via the immune system by ADCC or CDC, and further inhibits amino acid uptake of the cancer cells via LAT1, to suppress growth of the cancer cells. Accordingly, a preventive and therapeutic agent for cancer comprising this antibody or a fragment thereof, which acts on various cancers, is specific to cancer, and causes no side effect, is provided.

8 Claims, 22 Drawing Sheets

OTHER PUBLICATIONS

Acland, Dixon, Peters, and Dickson. Subcellular fate of the Int-2 oncoprotein is determined by choice of initiation codon. Nature, 1990. vol. 343, pp. 662-665.*

Verma and Somia. Gene therapy—promises, problems, and prospects. Nature, 1997. vol. 389, pp. 239-242.*

Pfeifer and Verma. Gene therapy: promises and problems. Annual Reviews in Genomics and Human Genetics, 2001. vol. 2, pp. 177-211.*

Kelland. "Of mice and men": values and liabilities of the athymic nude mouse model in anticancer drug development. European Journal of Cancer, 2004. vol. 40, pp. 827-836.*

Eck and Wilson. Gene Based Therapy. Goodman & Gilman, eds. The Pharmacological basis of Therapeutics, 1996. McGraw-Hill, New York, NY. pp. 77-101.*

Granziero, Krajewski, Farness, Yuan, Courtney, Jackson, Peterson, and Vitiello. Adoptive immunotherapy prevents prostate cancer in a transgenic animal model. European Journal of Immunology, 1999. vol. 29, pp. 1127-1138.*

Byers. What can randomized controlled trials tell us about nutrition and cancer prevention? CA Cancer Journal Clin. 1999. vol. 49, pp. 353-361.*

Osamu Yanagida et al., "Human L-type amino acid transporter 1 (LAT1): characterization of function and expression in tumor cell lines", Biochimica et Biophysica Acta 1514 (2001) 291-302.

Eijiro Nakamura et al., "4F2 (CD98) Heavy Chain Is Associated Covalently with an Amino Acid Transporter and Controls Intracellular Trafficking and Membrane Topology of 4F2 Heterodimer", The Journal of Biological Chemistry, vol. 274, No. 5, Issue of Jan. 29, 1999, pp. 3009-3016.

Kaori Hara et al., "Malignant Transformation of NIH3T3 Cells by Overexpression of Early Lymphocyte Activation Antigen CD98", Biochemical and Biophysical Research Communications 262, 720-725, 1999.

Kaori Hara et al., "Enhanced tumorigenicity caused by truncation of the extracellular domain of GP125/CD98 heavy chain", Oncogene (2000) 19, 6209-6215.

Tsuroka, et al., "Characterization of Human IgG Recognizing Intracellular CD98hc Epitope," Proceedings of the $63^{rd}$ Annual Meeting of the Japanese Cancer Association, Sep. 29-Oct. 1, 2004, Fukuoka, Japan, Cancer Science, vol. 95 Supplement, 2004, p. 310, p. 0808. (English Translation provided).

Tsuroka, et al., "Characterization of Human IgG Recognizing Intracellular CD98hc Epitope," Proceedings of the $63^{rd}$ Annual Meeting of the Japanese Cancer Association, Sep. 29-Oct. 1, 2004, Fukuoka, Japan, Cancer Science, vol. 95 Supplement, 2004, p. 310, p. 0808.

Supplementary European Search Report EP 07 74 1116 dated Feb. 17, 2010.

Hiroshi Nawashiro et al., "The Role of CD98 in Astrocytic Neoplasms", Human Cell, vol. 15, No. 1, (2002), pp. 25-31.

Do Kyung Kim et al., "Expression of L-type Amino Acid Transporter 1 (LAT1) and 4F2 Heavy Chain (4F2hc) in Oral Squamos Cell Carcinoma and it's Precursor Lesions", Anticancer Research 24: 16741-1676 (2004).

* cited by examiner

ANTI-CD98 ANTIBODY

REFERENCE TO RELATED APPLICATION

The present patent application claims the priority of Japanese Patent Application No. 2006-105013 (filing date: Apr. 6, 2006). The entire content disclosed in Japanese Patent Application No. 2006-105013 is incorporated herein by reference.

BACKGROUND OF THE INVENTION

The present invention relates to the results of the development involved in commission of new technology development concerning "anti-amino acid transporter protein antibody anticancer drug" assigned by Japan Science and Technology Agency.

FIELD OF THE INVENTION

The present invention relates to a monoclonal antibody having a specific binding ability to CD98 which is derived from the cell membrane of cancer cells and is in the form of a complex with a protein having an amino acid transporter activity, and pharmaceutical use thereof for suppression of tumor growth or cancer therapy.

BACKGROUND ART

Cancer (malignant tumor) is the primary cause of death in Japan. The number of cancer patients has been increasing year by year, and there are strong needs for development of drugs and therapeutic methods having high efficacy and safety. Conventional anticancer agents frequently have low ability to specifically kill cancer cells and act even on normal cells, leading to a great number of adverse drug reactions. Recently, development of anticancer agents targeting a molecule that is highly expressed in cancer cells (cancer-related antigen) has been progressed and these drugs have become effective therapeutic agents for leukemia, breast cancer, lung cancer, and the like.

It has been shown that an antibody that specifically binds to a cancer-related antigen expressed on the cell membrane attacks cancer cells via immunoreaction of antibody-dependent cellular cytotoxicity (ADCC), complement-dependent cell-mediated cytotoxicity (CDC) or the like, or suppresses cell growth signaling required for growth of cancer cells, and thus is useful for cancer therapy.

However, antibodies are used only for the treatment of limited types of cancers such as breast cancer, refractory chronic lymphoma, non-Hodgkin lymphoma, acute myelogenous leukemia and the like, and there is still no antibody that can be used alone for the treatment of various types of cancers. Accordingly, there is a demand to obtain an antibody that binds strongly to various types of cancer cells and has an anti-cancer activity.

CD98 (4F2) is a type II transmembrane glycoprotein chain of about 80 kDa composed of 529 amino acid residues, which is known to be highly expressed in various types of cancer cells. CD98 forms a heterodimer with a protein of about 40 kDa having an amino acid transporter activity via a disulfide bond and is expressed on the cell membrane. Six types of amino acid transporter proteins that are considered to bind to CD98 are known. Although CD98 is identified as a lymphocyte activation antigen, it is considered to be involved in a great number of biological functions such as cell growth signaling, integrin activation, cell fusion and the like (Haynes B. F. et al., J. Immunol., (1981), 126, 1409-1414, Lindsten T. et al., Mol. Cell Biol., (1988), 8, 3820-3826, Teixeira S. et al., Eur. J. Biochem., (1991), 202, 819-826, L. A. Diaz Jr. et al., J Biol Regul Homeost Agents, (1998) 12, 25-32).

Cancer cells have various mechanisms to ensure its dominance in the growth. For example, cancer cells overexpress neutral amino acid transporter in order to preferentially uptake essential amino acids necessary for the growth over surrounding cells; which is considered to be one of such mechanisms. L-type amino acid transporter 1 (LAT1), an amino acid transporter that is specifically and highly expressed in cancer cells, was recently cloned (Kanai et al., J. Biol. Chem. (1998), 273, 23629-23632). LAT1 forms a complex with CD98 and transports neutral amino acids having large side chains, such as leucine, valine, phenylalanine, tyrosine, tryptophan, methionine, histidine and the like in a sodium ion-independent manner. In addition, it is known that LAT1 is poorly or not expressed in most normal tissues except for the brain, placenta, bone marrow and testis, but its expression increases together with CD98 in tissues of human malignant tumors such as colorectal cancer, gastric cancer, breast cancer, pancreatic cancer, renal cancer, laryngeal cancer, esophageal cancer, lung cancer and the like (Yanagida et al., Biochem. Biophys. Acta, (2001), 1514, 291-302). It has been reported that when expression of LAT1 is reduced to suppress amino acid uptake, growth of a tumor is suppressed in a mouse model transplanted with cancer (Japanese Patent Laid-Open No. 2000-157286), and suppression of LAT1 activity is thus considered to be promising for cancer therapy.

With respect to antibodies against human CD98, a mouse monoclonal antibody that is prepared by immunizing a non-human mammal such as a mouse with a human CD98-expressing cell line has been reported (Haynes et al (ibid.), Masuko T. et al., Cancer Res., (1986), 46, 1478-1484, and Freidman A W. et al., Cell. Immunol., (1994), 154, 253-263). It has not been known, however, whether or not these anti-CD98 antibodies suppress amino acid uptake by LAT1. Further, although an antibody against the intracellular region of LAT-1 has been obtained, no antibody that can bind to LAT1 present on the cell membrane of a living cell has been reported. Accordingly, if an antibody that can bind to CD98 or LAT1 expressed on the cancer cell membrane to suppress amino acid uptake by LAT1 is obtained, the antibody is considered to be an excellent cancer therapeutic agent against cancers in a broad range.

SUMMARY OF THE INVENTION

The present inventors have now successfully obtained an antibody having specific binding ability to CD98 which is derived from a cell membrane of a cancer cell and is in the form of a complex with a protein having an amino acid transporter activity, and found that the antibody has an effect of suppressing the growth of cancer cells, and thus is useful as an active ingredient of a pharmaceutical composition, more specifically as an active ingredient of a preventive or therapeutic agent for tumors. The present invention is based on such findings.

Accordingly, an object of the present invention is to provide a human antibody having specific binding ability to CD98 which is derived from a cell membrane of a cancer cell and is in the form of a complex with a protein having an amino acid transporter activity, and a functional fragment thereof.

Another object of the present invention is to provide a pharmaceutical composition or a preventive or therapeutic agent for tumors, comprising the human antibody and a functional fragment thereof according to the present invention as an active ingredient.

The human antibody and a functional fragment thereof according to the present invention is characterized by having specific binding ability to CD98 which is derived from a cell membrane of a cancer cell and is in the form of a complex with a protein having an amino acid transporter activity.

Further, the pharmaceutical composition or the preventive or therapeutic agent for tumors according to the present invention comprises the human antibody and a functional fragment thereof according to the present invention as an active ingredient.

DETAILED DESCRIPTION OF THE INVENTION

Deposit of Microorganisms

Figure 1:
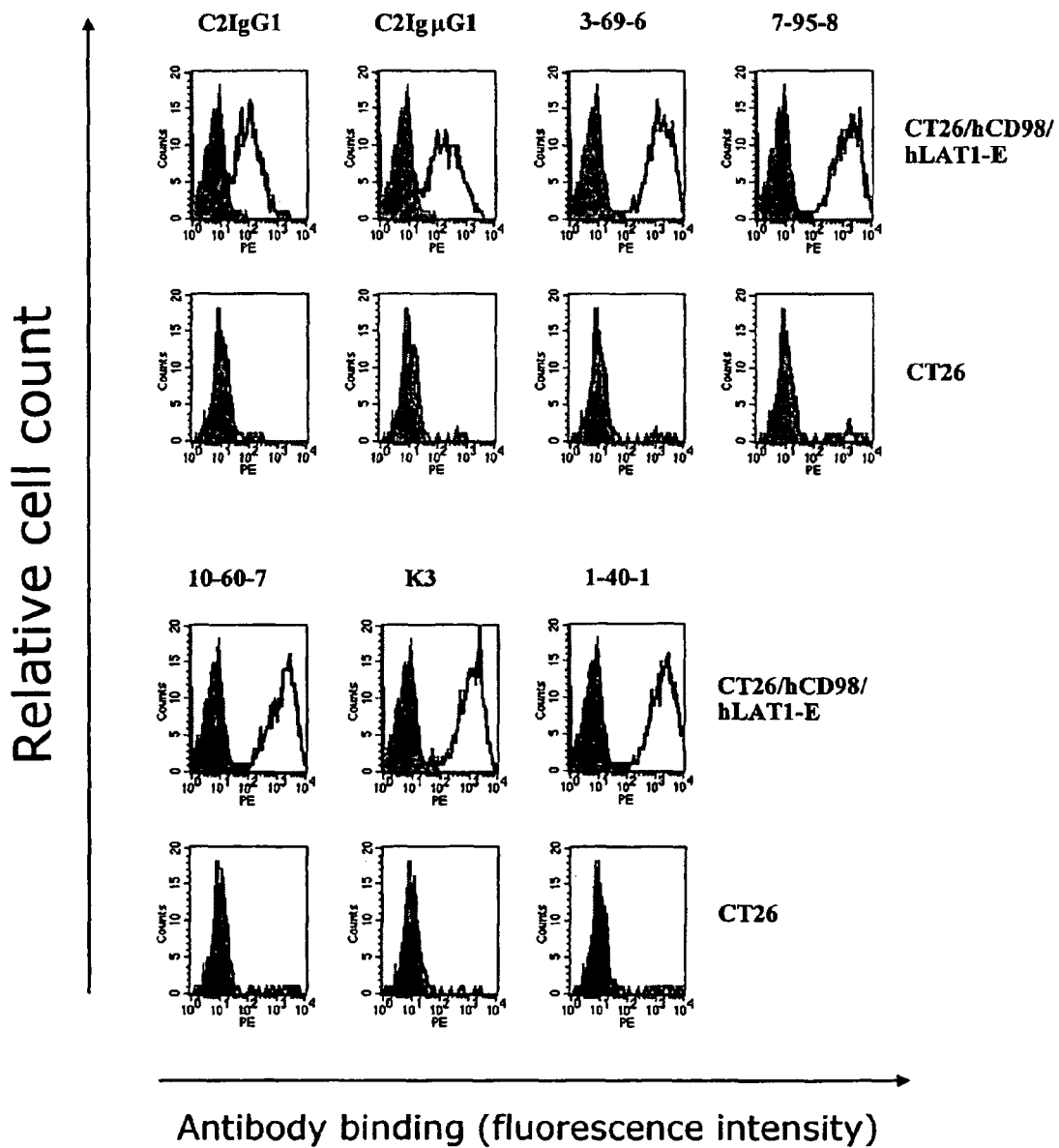
FIG. 1 shows the binding of human anti-CD98 monoclonal antibodies to a human CD98/human LAT1-expressing CT26 cell line.

Plasmid vectors C2IgG1/pCR4 and K3/pCR4 containing the nucleotide sequences coding for the variable region of the human antibody provided by the present invention were deposited on Mar. 14, 2006 to the International Patent Organism Depositary, National Institute of Advanced Industrial Science and Technology (Tsukuba Central 6, 1-1, Higashi 1-chome, Tsukuba-shi, Ibaraki-ken, Japan) with the accession Nos. FERM BP-10551 (indication for identification: C2IgG1/pCR4) and FERM BP-10552 (indication for identification: K3/pCR4), respectively.

Definitions

One-letter notations used for the description of amino acids in the present specification and Figures refer to the following respective amino acids: (G) glycine, (A) alanine, (V) valine, (L) leucine, (I) isoleucine, (S) serine, (T) threonine, (D) aspartic acid, (E) glutamic acid, (N) asparagine, (Q) glutamine, (K) lysine, (R) arginine, (C) cystein, (M) methionine, (F) phenylalanine, (Y) tyrosine, (W) tryptophan, (H) histidine, and (P) proline. One-letter alphabetic notations for the designation of DNA are as follows: (A) adenine, (C) cytocine, (G) guanine, and (T) thymine.

CD98 and Monoclonal Antibody Thereagainst

CD98, to which the human monoclonal antibody and a functional fragment thereof according to the present invention (hereinbelow abbreviated as "antibody according to the present invention," unless otherwise noted) has a specific binding ability, is a type II transmembrane glycoprotein chain composed of 529 amino acid residues and is in the form of a heterodimer with a protein having an amino acid transporter activity on the cell membrane, as described above. A preferred specific example of the protein having an amino acid transporter activity is LAT1. Further, in a preferred embodiment of the present invention, the CD98 is human CD98. The primary structure of the human CD98 protein is known (SEQ ID NO: 66; GenBank/EMBL/DDBJ accession No. AB018010) and that of the human LAT1 protein is also known (SEQ ID NO: 68; GenBank/EMBL/DDBJ accession No. AB018009).

The antibody according to the present invention has a specific binding ability to CD98 which is derived from a cell membrane of a cancer cell and is in the form of a complex with a protein having an amino acid transporter activity, while the antibody does not bind to normal human cells, for example, normal human vascular endothelial cells, normal human peripheral blood monocytes, or lymphocytes. Examples of the cancer cells to which the antibody has a binding ability include cancer cells constituting colorectal cancer, lung cancer, breast cancer, prostatic cancer, melanoma, brain tumor, lymphoma, bladder cancer, pancreatic cancer, multiple myeloma, renal cell carcinoma, leukemia, T-cell lymphoma, gastric cancer, pancreatic cancer, cervical cancer, endometrial cancer, ovarian cancer, esophageal cancer, liver cancer, head and neck squamous cell carcinoma, skin cancer, urinary tract cancer, prostatic cancer, chorionic carcinoma, pharyngeal cancer, laryngeal cancer, pleural tumor, arrhenoblastoma, endometrial hyperplasia, endometriosis, embryoma, fibrosarcoma, Kaposi's sarcoma, angioma, cavernous angioma, hemangioblastoma, retinoblastoma, astrocytoma, neurofibroma, oligodendroglial tumor, medulloblastoma, neuroblastoma, gliocystoma, rhabdomyoblastoma, glioblastoma, osteogenic sarcoma, leiomyosarcoma, thyroid sarcoma, Wilms tumor or the like, more specifically, colorectal cancer cell lines (DLD-1, Colo205, SW480, SW620, LOVO, LS180, and HT29), a lung cancer cell line (H226), a prostate cancer cell line (DU145), a melanoma cell line (G361, SKMEL28, and CRL1579), a non-Hodgkin lymphoma cell line (Ramos), a bladder cancer cell line (T24), a breast cancer cell line (MCF and MDA-MB-231), a pancreatic cancer cell line (HS766T), a multiple myeloma cell line (IM9), an erythroblastic leukemia cell line (K562). The antibody according to the present invention is advantageous in terms of the binding ability to such a variety of cancer cells.

The specific binding ability of the antibody according to the present invention to cancer cells increases usefulness of the antibody according to the present invention. In other words, as described below, the antibody according to a preferred embodiment of the present invention advantageously binds only to cancer cells in order to significantly inhibit the amino acid uptake into cells via LAT1, and the antibody according to the present invention can be advantageously used, as a targeting agent, to bind to another drug and deliver the drug to cancer cells.

Further, the antibody according to the present invention has an anti-tumor activity. The antibody according to a preferred embodiment of the present invention has a property of significantly inhibiting the amino acid uptake into cells via LAT1. Accordingly, the anti-tumor activity of the antibody according to the present invention is considered to be attributable to giving a specific damage using an immune system by ADCC and CDC, as well as to inhibiting the amino acid uptake as in the above. In a more specific embodiment of the present invention, the antibody according to the present invention significantly inhibits the amino acid uptake of bladder cancer cell line T24 cells.

In a preferred embodiment of the present invention, the antibody according to the present invention has any pair of sequences of (a) SEQ ID NOs: 29 and 31, (b) SEQ ID NOs: 41 and 47, and (c) SEQ ID NOs: 43 and 47 described below as a heavy chain variable region and a light chain variable region thereof. Further, in another embodiment of the present invention, the antibody according to the present invention has, as variable regions, sequences encoded by sequences contained in a plasmid vector K3/pCR4 (FERM BP-10552) or C2IgG1/pCR4 (FERM BP-10551) provided that the sequence from a vector pCR4 is excluded. The amino acid sequences of the variable regions of the antibody according to this embodiment are encoded by a BglII-BsiWI fragment (light chain variable region) and a SalI-NheI fragment (heavy chain variable region), which are obtained from any of the plasmid vectors described above and contain no sequence from a vector pCR4.

The functional fragment of the antibody according to the present invention refers to a fragment of the antibody specifically binding to the antigen to which the antibody according to the present invention specifically binds, and more specifically includes F(ab')2, Fab', Fab, Fv, disulphide-linked FV, Single-Chain FV (scFV) and polymers thereof, and the like (D. J. King., Applications and Engineering of Monoclonal Antibodies., 1998, T.J. International Ltd). These antibody fragments can be obtained by a conventional method, for example, digestion of an antibody molecule by a protease such as papain, pepsin and the like, or by a known genetic engineering technique.

"Human antibody" used in the present invention refers to an antibody that is an expression product of a human-derived antibody gene. The human antibody can be obtained by administration of an antigen to a transgenic animal to which a human antibody locus has been introduced and which has an ability of producing human-derived antibody. An example of the transgenic animal includes a mouse, and a method of creating a mouse capable of producing a human antibody is described in, for example, WO 02/43478 pamphlet.

The antibody according to the present invention also includes a monoclonal antibody composed of a heavy chain and/or a light chain, each having an amino acid sequence in which one or several amino acids are deleted, substituted, or added in each amino acid sequence of a heavy chain and/or a light chain constituting the antibody. Such a partial modification (deletion, substitution, insertion, or addition) of an amino acid(s) can be introduced into the amino acid sequence of the antibody according to the present invention by partially modifying the nucleotide sequence encoding the amino acid sequence. The partial modification of a nucleotide sequence can be introduced by an ordinary method using known site-specific mutagenesis (Proc Natl Acsd Sci USA., 1984, Vol 8, 15662; Sambrook et al., Molecular Cloning A Laboratory Manual (1989) Second edition, Cold Spring Harbor Laboratory Press).

In a preferred embodiment of the present invention, the antibody according to the present invention is an antibody in which isoleucine at position 117 of the light chain is substituted with another amino acid residue, for example, methionine, asparagine, leucine or cystein. Preferred examples of such an antibody include those having, as a heavy chain variable region and a light chain variable region, any pair of sequences of (d) SEQ ID NOs: 43 and 77, (e) SEQ ID NOs: 43 and 79, (f) SEQ ID NOs: 43 and 81, and (g) SEQ ID NOs: 43 and 83.

The antibody according to the present invention includes an antibody having any immunoglobulin class and subclass. In a preferred embodiment of the present invention, the antibody is an antibody of human immunoglobulin class and subclass, and preferred class and subclasses are immunoglobulin G (IgG), especially, IgG1, and a preferred light chain is K.

Further, the antibody according to the present invention also includes an antibody converted into a different subclass by modification by genetic engineering known by the person skilled in the art (for example, EP0314161). In other words, an antibody of a subclass different from the original subclass can be obtained from a DNA encoding a variable region of the antibody according to the present invention by genetic engineering technique.

ADCC refers to a cytotoxic activity that is induced by recognition of a cell through binding to a constant region of an antibody via an Fc receptor expressed on the surface of macrophages, NK cells, neutrophils, and the like and activation of the recognized cell. On the other hand, CDC refers to a cytotoxic activity caused by the complement system activated by binding of an antibody to an antigen. It has been revealed that the strength of these activities differs depending on the subclass of antibody and the difference is due to a difference in the structure of a constant region of an antibody (Charles A. Janeway, et. al. Immunobiology, 1997, Current Biology Ltd/ Garland Publishing Inc.).

Accordingly, for example, an antibody having a lower binding strength to an Fc receptor can be obtained by converting the subclass of the antibody according to the present invention to IgG2 or IgG4. On the contrary, an antibody having a higher binding strength to an Fc receptor can be obtained by converting the subclass of the antibody according to the present invention into IgG1 or IgG3. When the above ADCC and CDC activities are expected, the subclass of antibody is desirably IgG1.

When an antibody of a different subclass is converted into IgG1, IgG1 can be prepared, for example, by isolating only a variable region from an antibody-producing hybridoma and introducing the variable region into a vector containing the constant region of human IgG1, for example, N5KG1-Val Lark vector (IDEC Pharmaceuticals, N5KG1 (U.S. Pat. No. 6,001,358)).

Further, it is possible to change a binding strength to an Fc receptor by modifying the amino acid sequence of the constant region of the antibody according to the present invention by genetic engineering, or by binding a constant region sequence having such a sequence (see Janeway C A. Jr. and Travers P. (1997), Immunobiology, Third Edition, Current Biology Ltd./Garland Publishing Inc.), or to change a binding strength to a complement (see Mi-Hua Tao, et al., 1993, J. Exp. Med). For example, a binding strength to a complement can be changed by substituting proline with serine by mutating the sequence CCC encoding proline (P) at position 331 according to the EU Numbering System (see Sequences of proteins of immunological interest, NIH Publication No. 91-3242) of the constant region of the heavy chain into the sequence TCC encoding serine (S).

For example, if the antibody according to the present invention by itself does not possess a cell death-inducing activity, an antibody having antitumor activity due to antibody-dependent cell-mediated cytotoxicity (ADCC) and complement-dependent cytotoxicity (CDC) via an Fc receptor is desirable. However, when the antibody by itself has a cell death-inducing activity, an antibody having a lower binding strength to an Fc receptor may be more desirable in some cases.

Considering immunosuppressants, an antibody having no ADCC activity or no CDC activity is desired, when sterically inhibiting only the binding of T cells and antigen-presenting cells, and the like. In addition, when an ADCC activity or a CDC activity may be a cause of toxicity, an antibody in which an activity causing toxicity is avoided by mutating the Fc region or changing the subclass may be desirable in some cases.

Considering above, the antibody according to the present invention may be an antibody that can specifically damage cancer cells by ADCC or CDC by converting to another subclass through genetic engineering, if necessary.

In another preferred embodiment of the present invention, the antibody according to the present invention preferably recognizes an epitope constituted by at least 8 consecutive or non-consecutive amino acid residues in the amino acid sequence of human CD98 (SEQ ID NO: 66). In a more preferred embodiment of the present invention, the antibody according to the present invention preferably has a binding ability to part of the region of amino acids 371 to 529 or part of the region of amino acids 1 to 371 of the amino acid sequence of human CD98.

In another embodiment of the present invention, an antibody having cross-reactivity to human CD98 and monkey CD98 is provided as the antibody according to the present invention. Such an antibody is assumed to recognize the same or a highly similar epitope structure in human CD98 and monkey CD98, and has an advantage that various tests can be conducted in monkeys as experimental animals prior to clinical studies in human.

Preparation of CD98 Antibody

The antibody according to the present invention can be produced by, for example, the following method. Immunization is conducted by immunizing non-human mammals such as mice, rabbits, goats, horses and the like with human CD98/ human LAT1 or a part thereof, or a conjugate thereof with an appropriate substance (for example, bovine serum albumin) to enhance antigenicity of an antigen, or cells on the surface of which human CD98/human LAT1 is expressed in a large amount, in combination with an immunostimulant (Freund's Adjuvant, etc.), if required, or by administering an expression vector incorporated with human CD98/human LAT1 to the non-human mammals. The antibody according to the present invention can be obtained by preparing a hybridoma from antibody-producing cells obtained from an immunized animal and myeloma cells lacking autoantibody producing ability, cloning the hybridoma, and selecting a clone producing a monoclonal antibody exhibiting specific affinity to the antigen used for immunization.

The method for preparing the antibody according to the present invention will be more specifically described in detail below, but the method for preparing the antibody is not limited thereto, and, for example, antibody-producing cells other than spleen cells and myeloma can also be used.

As the antigen, a transformant that is obtained by incorporating a DNA encoding CD98 into an expression vector for animal cells and introducing the expression vector to animal cells can be used.

Since CD98 forms a heterodimer with LAT1 on the cell surface of many cancer cells, an antibody that inhibits amino acid uptake by LAT1 is expected to be obtained by incorporating a DNA encoding LAT1 into an expression vector in a similar manner and using a transformant in which CD98 and LAT1 are coexpressed as an antigen.

As the expression vector for animal cells, for example, vectors such as pEGF-N1 (manufactured by Becton Dickinson Bioscience Clontech) can be used. A vector for introducing an intended gene can be prepared by cleaving an insertion site by an appropriate restriction enzyme and linking the human CD98 or human LAT1 cleaved by the same enzyme. The prepared expression vector can be introduced into cells, for example, L929 cells (American Type Culture Collection No. CCL-1) as a host to prepare cells highly expressing human CD98 and human LAT1.

The methods for introducing a gene into a host are known and include, for example, any methods (for example, a method using a calcium ion, an electroporation method, a spheroplast method, a lithium acetate method, a calcium phosphate method, a lipofection method and the like).

The transformed cells thus prepared can be used as an immunogen for preparing a CD98 antibody. The expression vector itself can also be used as an immunogen.

Human CD98 can be produced by appropriately using a method known in the art, such as a genetic recombination technique as well as a chemical synthesis method and a cell culture method based on the known nucleotide sequence or amino acid sequence of the CD98. The human CD98 protein thus obtained can also be used as an antigen to prepare a CD98 antibody. A partial sequence of human CD98 can also be produced by a gene recombination technique or a chemical synthesis in accordance with a method known in the art described below, or produced by cleaving human CD98 appropriately using a protein degradation enzyme, or the like.

The antigen obtained as described above can be used for immunization as described below. Specifically, the prepared antigen is mixed with an appropriate substance for enhancing the antigenicity (for example, bovine serum albumin and the like) and an immunostimulant (Freund complete or incomplete adjuvant, and the like), as required, and used for immunization of a non-human mammal such as a mouse, rabbit, goat, and a horse. In addition, preferably, the antibody according to the present invention may be obtained as a human antibody using a non-human animal that has an unrearranged human antibody gene and produces a human antibody specific to the antigen by immunization. In this case, examples of the animals producing human antibody include transgenic mice producing human antibody described in the literature of Tomizuka et al. (Tomizuka et al., Proc. Natl. Acad. Sci. USA, 2000, Vol 97: 722).

A hybridoma secreting a monoclonal antibody can be prepared by a method of Kohler and Milstein (Nature, 1975, Vol. 256: 495-497) or in accordance with the method. In other words, a hybridoma is prepared by cell fusion between antibody producing cells contained in the spleen, lymph nodes, bone marrow, tonsil, or the like, preferably contained in the lymph nodes or spleen, obtained from an animal immunized as described above, and myeloma cells that are derived preferably from a mammal such as a mouse, a rat, a guinea pig, hamster, a rabbit, a human or the like and incapable of producing any autoantibody. Cell fusion can be performed by mixing antibody-producing cells with myeloma cells in a high concentration solution of a polymer such as polyethylene glycol (for example, molecular weight of 1500 to 6000) usually at about 30 to 40° C. for about 1 to 10 minutes. A hybridoma clone producing a monoclonal antibody can be screened by culturing a hybridoma on, for example, a microtiter plate, and measuring reactivity of a culture supernatant from wells in which the hybridoma is grown to an immunization antigen using an immunological method such as an enzyme immunoassay (for example, ELISA), a radioimmunoassay, or a fluorescent antibody method.

A monoclonal antibody can be produced from a hybridoma by culturing the hybridoma in vitro and then isolating monoclonal antibodies from a culture supernatant. A monoclonal antibody can also be produced by a hybridoma by culturing the hybridoma in ascites or the like of a mouse, a rat, a guinea pig, a hamster, a rabbit, or the like in vivo and isolating the monoclonal antibody from the ascites. Further, a recombinant antibody can be prepared by a genetic recombination technique by cloning a gene encoding a monoclonal antibody from antibody-producing cells such as a hybridoma and the like, and incorporating the gene into an appropriate vector, introducing the vector to a host (for example, cells from a mammalian cell line, such as Chinese hamster ovary (CHO) cells and the like, *E. coli*, yeast cells, insect cells, plant cells and others (P. J. Delves. ANTIBODY PRODUCTION ESSENTIAL TECHNIQUES., 1997, WILEY, R Shepherd and C. Dean., Monoclonal Antibodies., 2000, OXFORD UNIVERSITY PRESS, J. W. Goding, Monoclonal Antibodies: principles and practice., 1993, ACADEMIC PRESS). Further, by preparing a transgenic bovine, goat, sheep or porcine in which a gene of a target antibody is incorporated into an endogenous gene using a transgenic animal production technique, a large amount of a monoclonal antibody derived from the antibody gene may be obtained from the milk of the transgenic animal. When a hybridoma is cultured in vitro, the hybridoma is grown, maintained, and stored depending on the various conditions such as properties of a cell species to be cultured, objectives of a study, and culture methods and the like, and the culture may be conducted using a known nutritional medium or any nutritional mediums induced and prepared from a known basic medium that are used to produce a monoclonal antibody in a culture supernatant.

The produced monoclonal antibody can be purified by a method known in the art, for example, by appropriate combination of chromatography using a protein A column, ion-exchange chromatography, hydrophobic chromatography, ammonium sulfate salting-out, gel filtration, affinity chromatography, and the like.

Pharmaceutical Use of Antibody

The antibody according to the present invention can form a complex that may be used for the purpose of treatment such as drug delivery to cancer cells, missile therapy, and the like, by conjugating the antibody with a therapeutic agent, because of the specific binding ability to CD98 which is derived from the cell membrane of cancer cells and is in the form of a complex with a protein having an amino acid transporter activity.

Examples of the therapeutic agent to be conjugated to the antibody include, but not limited to, radionuclides such as iodine ($^{131}$iodine: $^{131}$I, $^{125}$iodine: $^{125}$I), yttrium ($^{90}$yttrium: $^{90}$Y), indium ($^{111}$indium: $^{111}$In), technetium ($^{99m}$technetium: $^{99m}$Tc) and the like (J. W. Goding. Monoclonal Antibodies: principles and practice., 1993, ACADEMIC PRESS); bacterial toxins such as *Pseudomonas exotoxin*, diphtheria toxin, and ricin; and chemotherapeutic agents such as methotrexate, mitomycin, calicheamicin and the like (D. J. King., Applications and Engineering of Monoclonal Antibodies., 1998, T.J. International Ltd, M. L. Grossbard., Monoclonal Antibody-Based Therapy of Cancer., 1998, Marcel Dekker Inc), preferably a selenium compound inducing a radical production.

An antibody may be bound to a therapeutic agent via covalent bonding or non-covalent bonding (for example, ion bonding). For example, the complex of the present invention can be obtained, using a reactive group (for example an amine group, a carboxyl group, or a hydroxy group) in a molecule or a coordination group, after binding to a more reactive group or being converted into a reactive group, as required, by bringing an antibody into contact with a therapeutic agent having an functional group capable of reacting with the reactive group to form bonding (in the case of bacterial toxin or chemotherapeutic agent) or an ionic group capable of forming a complex with the coordination bond (in the case of radionuclide). Alternatively, a biotin-avidin system can also be utilized for complex formation.

When the therapeutic agent is a protein or a peptide, a fusion protein of the antibody and the protein or peptide can be produced by a genetic engineering technique.

Further, since the antibody according to the present invention has an antitumor activity, the antibody itself can be used as an anti-tumor agent. In addition, the antibody can be used as an active ingredient of a pharmaceutical composition, especially a preventive or therapeutic agent for tumors.

Accordingly, the antibody or the pharmaceutical composition according to the present invention can be applied to treatment or prevention of various diseases or symptoms that may be attributable to the cells expressing human CD98/ human LAT1. Examples of the disease or symptom include various malignant tumors, and examples of the tumor include colorectal cancer, lung cancer, breast cancer, prostatic cancer, melanoma, brain tumor, lymphoma, bladder cancer, pancreatic cancer, multiple myeloma, renal cell carcinoma, leukemia, T-cell lymphoma, gastric cancer, pancreatic cancer, cervical cancer, endometrial cancer, ovarian cancer, esophageal cancer, liver cancer, head and neck squamous cell carcinoma, skin cancer, urinary tract cancer, prostatic cancer, chorionic carcinoma, pharyngeal cancer, laryngeal cancer, pleural tumor, arrhenoblastoma, endometrial hyperplasia, endometriosis, embryoma, fibrosarcoma, Kaposi's sarcoma, angioma, cavernous angioma, hemangioblastoma, retinoblastoma, astrocytoma, neurofibroma, oligodendroglial tumor, medulloblastoma, neuroblastoma, gliocystoma, rhabdomyoblastoma, glioblastoma, osteogenic sarcoma, leiomyosarcoma, thyroid sarcoma, Wilms tumor and the like. The antibody according to the present invention may be applied not only to one tumor but multiple tumors complicated together. The human monoclonal antibody according to the present invention may be applied for prolongation of the life of a patient with primary local cancer. Further, the pharmaceutical composition according to the present invention is allowed to act selectively on immunocompetent cells expressing CD98.

A medicament containing the antibody according to the present invention or the antibody bound to a therapeutic agent is preferably provided as a pharmaceutical composition.

Such a pharmaceutical composition contains a therapeutically effective amount of a therapeutic agent and is formulated into various forms for oral or parenteral administration. The therapeutically effective amount used herein refers to an amount that exhibits a therapeutic effect on a given symptom in a given dosage regimen.

The composition according to the present invention may comprises, in addition to the antibody, one or more physiologically acceptable pharmaceutical additives, for example, diluents, preservatives, solubilizers, emulsifiers, adjuvants, antioxidants, tonicity agents, excipients, and carriers. Further, the composition can be a mixture with other drugs such as other antibodies or antibiotics.

Examples of the appropriate carrier include, but not limited to, physiological saline, phosphate buffered physiological saline, phosphate buffered physiological saline glucose solution and buffered physiological saline. Stabilizers such as amino acids, sugars, surfactants and the like and surface-adsorption inhibitors that are known in the art may be contained.

As the form of the formulation, a formulation can be selected depending on an object of the treatment and therapeutic regimen from formulations including lyophilized formulations (that can be used after reconstitution by addition of a buffered aqueous solution as described above), sustained-release formulations, enteric formulations, injections, drip infusions and the like.

A route of administration may be determined appropriately, and an oral route as well as a parenteral route including intravenous, intramuscular, subcutaneous and intraperitoneal injections and drug deliveries may be considered. Alternatively, a method in which the composition according to the present invention is brought into contact directly with an affected site of a patient may also be conducted.

The dose can be appropriately determined by animal studies and clinical studies, but in general, should be determined in consideration of a condition or severity, age, body weight, sex, and the like of a patient. In general, for oral administration, the dose is about 0.01 to 1000 mg/day for adults, which may be administered once daily or divided into several times a day. For parenteral administration, about 0.01 to 1000 mg/dose can be administered by subcutaneous injection, intramuscular injection or intravenous injection.

The present invention encompasses a preventive or therapeutic method of the diseases described above using the antibody or pharmaceutical composition according to the present invention, and also encompasses use of the antibody according to the present invention for the manufacture of a preventive or therapeutic agent for the diseases described above.

In a preferred embodiment of the present invention, the antibody according to the present invention is used as an ampoule containing a sterile solution or suspension obtained by dissolving the antibody in water or a pharmacologically acceptable solution. In addition, a sterile powder formulation (preferably, a molecule of the present invention is lyophilized) may be filled in an ampoule and reconstituted with a pharmacologically acceptable solution at the time of use.

EXAMPLES

The present invention will be illustrated in more detail by the following Examples, but the present invention is not limited to the embodiments described in these Examples.

Example 1

Preparation of Human CD98 or Human LAT1 Expression Vector

Polymerase chain reaction (PCR) was conducted using plasmid vectors pcDNA3.1-hCD98 and pcDNA3.1-hLAT1 containing DNA of human CD98 (hCD98, GenBank/EMBL/DDBJ accession no. AB018010; SEQ ID NO: 65) and human LAT1 (hLAT1, GenBank/EMBL/DDBJ accession no. AB018009; SEQ ID NO: 67), respectively, as templates. In order to add the EcoRI sequence to the 5' end of the full length human CD98 cDNA and the NotI sequence and a termination codon to the 3' end, primers 5'-CCG GAA TTC CCA CCA TGA GCC AGG ACA CCG AGG TGG ATA TGA-3' (SEQ ID NO: 59) and 5'-AAG GAA AAA AGC GGC CGC TCA TCA GGC CGC GTA GGG GAA GCG GAG CAG CAG-3' (SEQ ID NO: 60) were used and KOD-Plus DNA Polymerase (manufactured by Toyobo) and hCD98c DNA (about 20 ng) were used as templates to perform 30 cycles of PCR at 94° C. for 15 seconds, at 55° C. for 30 seconds, and at 68° C. for 1 minute 30 seconds. The modified hCD98 sequence was isolated as an EcoRI-NotI fragment and ligated to a pTracer-EF/Bsd vector (manufactured by Invitrogen) that had been cleaved by the same enzyme. The obtained plasmid was used as a template and CD98 v2 U (5'-AGT CTC TTG CAA TCG GCT AAG AAG AAG AGC ATC CGT GTC ATT CTG-3' (SEQ ID NO: 61)) primer and CD98 v2 L (5'-CAG AAT GAC ACG GAT GCT CTT CTT CTT AGC CGA TTG CAA GAG ACT-3' (SEQ ID NO: 62)) primer were used to change A of positions of 591 and 594 of hCD98 DNA (positions of 702 and 705 in SEQ ID NO: 65) to G. An EcoRI-hCD98-NotI fragment was prepared from the obtained plasmid and ligated to pEF6myc-His/Bsd (Invitrogen) vector that had been cleaved by the same enzyme. The obtained plasmid was named as pEF6/hCD98.

In a similar manner, in order to add the EcoRI sequence to the 5' end of the full length human LAT1 cDNA and the KpnI sequence to the 3' end, primers 5'-CCG GAA TTC CCA CCA TGG CGG GTG CGG GCC CGA AGC GGC-3' (SEQ ID NO: 63) and 5'-CGG GGT ACC GTC TCC TGG GGG ACC ACC TGC ATG AGC TTC-3' (SEQ ID NO: 64) were used and KOD-Plus DNA polymerase and hLAT1 cDNA (about 20 ng) were used as templates to perform 30 cycles of PCR reaction at 94° C. for 15 seconds; at 55° C. for 30 seconds; and at 68° C. for 1 minute 30 seconds. The modified hLAT1 sequence was isolated as an EcoRI-KpnI fragment and ligated to a pEGFP-N1 (manufactured by Clontech) vector that had been cleaved by the same enzyme. Further, the obtained plasmid was isolated as an EcoRI-NotI fragment and ligated to a pEF1V5His/Neo (manufactured by Invitrogen) vector that had been cleaved by the same enzyme. The obtained plasmid was named as pEF1/hLAT1-EGFP.

Example 2

Preparation of hCD98/hLAT1-Expressing Cells hCD98/hLAT1-expressing cells were prepared by introducing the expression vectors pEF6/hCD98 and pEF1/hLAT1-EGFP (hLAT1-E) prepared in Example 1 to Colon 26 (CT26) cells and L929 cells (American Type Culture Collection No. CCL-1) using Lipofectamine and Plus reagent manufactured by Invitrogen. The gene introduction was conducted in accordance with the method described in the manual. The transgenic cells were cultured in a cell culture plate (6-well plate, manufactured by Becton Dickinson) at 37° C. in 5% carbonate gas for 24 hours and then cultured in a culture medium containing blasticidin (5 μg/mL) and G418 (500 μg/mL) in the case of the CT26 cell line and a culture medium containing blasticidin (5 μg/mL) and G418 (1 mg/mL) in the case of the L929 cell line for further 3 days. hLAT1-E and CD98 positive cells were then separated by FACS Vantage using RPE fluorescently-labeled mouse anti-human CD98 antibody (Becton Dickinson, Ca. No. 556076). hCD98-expressing L929 cells or hLAT1-E-expressing L929 cells were prepared in a similar manner.

Example 3

Preparation of Human Antibody-Producing Mice

Mice used for immunization have a genetic background of being homozygous for disruption of both endogenous Ig heavy chain and K light chain and retaining a chromosome 14 fragment (SC20) containing a human Ig heavy chain locus and a human IgK chain transgene (KCo5) simultaneously. These mice were prepared by crossing a mouse of line A having a human Ig heavy chain locus and a mouse of line B having a human Ig K chain transgene. The mice of line A are homozygous for disruption of both endogenous Ig heavy chain and K light chain and retain a chromosome 14 fragment (SC20) that is transmissible to progeny, and are described, for example, in the report of Tomizuka, et al. (Tomizuka. et al., Proc Natl Acad Sci USA, 2000, Vol 97: 722). The mice of line B are transgenic mice, which are homozygous for disruption of both endogenous Ig heavy chain and K light chain and retain a human Ig K chain transgene (KCo5), and are described, for example, in the report of Fishwild, et al. (Nat. Biotechnol., 1996, Vol 14: 845).

Progeny mice obtained by crossing a male mouse of line A and a female mouse of line B or a female mouse of line A and a male mouse of line B were analyzed by the method described in the report of Tomizuka (Tomizuka et al., Proc Natl Acad Sci USA, 2000, Vol 97: 722), and individuals (human antibody-producing mice) for which human Ig heavy chain and K light chain were detected simultaneously in serum were screened (Ishida & Lonberg, IBC's 11th Antibody Engineering, Abstract, 2000; Ishida, I. et al., Cloning & Stem Cells 4, 85-96 (2002)) and used in the following immunization experiments. In the immunization experiments, mice and the like having altered genetic backgrounds of the above mice were also used (Ishida Isao (2002), Jikken Igaku, 20, 6846851).

Example 4

Preparation of Human Monoclonal Antibodies

Monoclonal antibodies were prepared in accordance with a general method as described in, for example, "Introduction of Experimental Protocols for Monoclonal Antibody" (Monoclonal Antibody Jikken Sosa Nyumon, written by Tamie ANDO et al., KODANSHA, 1991).

As an immunogen hCD98/hLAT1, the hCD98/hLAT1-E-expressing CT26 cells prepared in Example 2 and human colorectal cancer cell line Colo205 cells for which expression of hCD98 was confirmed were used.

As animals for immunization, the human antibody-producing mice producing human immunoglobulin that had been prepared in Example 3 were used.

When the hCD98/hLAT1-E-expressing CT26 cells were used, $5 \times 10^6$ cells were mixed with RIBI adjuvant (manufactured by Corixa) and given intraperitoneally for primary immunization. On days 7 and 24 after the primary immunization, $5 \times 10^6$ cells/mouse were given intraperitoneally for booster immunization. The cells were further immunized in the same manner 3 days prior to acquisition of spleen cells described below.

When Colo205 cells were used, $5 \times 10^6$ cells were given intraperitoneally for primary immunization. On day 14 after the primary immunization, $5 \times 10^6$ cells/mouse were given intraperitoneally for booster immunization, and spleen cells described below were obtained 3 days later.

The spleen was obtained surgically from the immunized mice, and the spleen cells recovered were mixed with mouse myeloma SP2/0 (ATCC No. CRL1581) cells at a ratio of 5:1 and the cells were fused using polyethylene glycol 1500 (manufactured by Roche) as a fusing agent to prepare a large number of hybridomas. The hybridomas were cultured in a HAT-containing DMEM medium (manufactured by Gibco) containing 10% fetal calf serum (FCS) and hypoxanthine (H), aminopterin (A), and thymidine (T) for screening. Single clones were obtained using a HT-containing DMEM medium by limiting dilution. A 96-well microtiter plate (manufactured by Becton Dickinson) was used for culturing. Selection (screening) for hybridoma clones producing an intended human monoclonal antibody and characterization of the human monoclonal antibodies produced by the respective hybridomas were conducted by measurement with a fluorescence-activated cell sorter (FACS) described below.

Screening for human monoclonal antibody-producing hybridomas was conducted as described below. In other words, 200 or more hybridomas producing human monoclonal antibodies, which contained a human immunoglobulin μ chain (hIgμ), a γ chain (hIgγ), and a human immunoglobulin light chain κ (hIgκ) and had specific reactivity to hCD98/hLAT1-E-expressing CT26 cells, were obtained by the FACS analysis described below.

In Examples in the present specification, the hybridoma clones that produced each of the human monoclonal antibodies are named using the symbols in Tables and Figures showing the results. The following hybridoma clones represent single clones: 4-35-14 (C2), 4-32-9 (K3), 7-95-8, 10-60-7, 3-69-6, 5-80-1 (for the above clones, the immunogen is hCD98/hLAT1-E-expressing CT26 cells); and 1-40-1 (for the clone, the immunogen is Colo205 cells).

Example 5

Identification of Subclasses of Each of the Monoclonal Antibodies

The subclass of each of the monoclonal antibodies obtained in Example 4 was identified by FACS analysis.

2×10⁶/mL of Colo205 cells were suspended in a Staining Buffer (SB) of PBS containing 1 mM EDTA, 0.1% NaN₃, and 5% FCS. The cell suspension was dispensed in a 96-well round-bottomed plate (manufactured by Becton Dickinson) at 50 μL/well. Further, the culture supernatant (50 μL) of the hybridoma cultured in Example 4 was added thereto, and the mixture was stirred, allowed to react at ice temperature for 30 minutes, and then centrifuged (2000 rpm, 4° C., 2 minutes) to remove the supernatant. After the pellets were washed once with 100 μL/well of SB, an FITC fluorescently-labeled rabbit anti-human Igμ F(ab')₂ antibody (manufactured by Dako Cytomation) diluted 50 time with SB, or an RPE fluorescently-labeled goat anti-human Igγ F(ab')₂ antibody (manufactured by SuthernBiotech) diluted 200 times with SB, or an RPE fluorescently-labeled rabbit anti-human Igκ F(ab')₂ antibody (manufactured by Dako Cytomation) diluted 200 times with SB was added thereto, and the mixture was allowed to react at ice temperature for 30 minutes. After washing once with SB, the cells were suspended in 300 μL of SB and a fluorescence intensity indicating antibody binding was measured with an FACS (FACSCan, manufactured by Becton Dickinson). The results for parts of the obtained antibodies are shown in Table 1. For the C2, the heavy chain was μ chain and the light chain was κ chain, and for all of the K3, 3-69-6, 7-95-8, 10-60-7, 1-40-1, and 5-80-1, the heavy chain was γ chain and the light chain was κ chain.

TABLE 1

Subclass of antibodies

| Clone | Light chain | Heavy chain |
|---|---|---|
| K3 | Human κ | Human γ |
| C2 | Human κ | Human μ |
| 1-40-1 | Human κ | Human γ |
| 3-69-6 | Human κ | Human γ |
| 7-95-8 | Human κ | Human γ |
| 10-60-7 | Human κ | Human γ |
| 5-80-1 | Human κ | Human γ |

Example 6

Preparation of Genes Encoding Monoclonal Antibodies and Construction of Recombinant Antibody-Expression Vectors Cloning of the genes of the respective antibodies C2, K3, 7-95-8, 10-60-7, 3-69-6 and 1-40-1 and construction of expression vectors were conducted in accordance with the methods described below.
(1) cDNA Cloning of Antibody Genes and Preparation of Expression Vectors The hybridoma was cultured in a DMEM medium (manufactured by Gibco) containing 10% FCS, the cells were collected by centrifugation, and then ISOGEN (manufactured by Nippon Gene) was added to extract total RNA in accordance the instruction manual. Cloning of the variable region of the antibody cDNAs was conducted using a SMART RACE cDNA amplification Kit (manufactured by Clontech) in accordance with the attached instruction manual.

The 1st strand cDNA was prepared using 5 μg of the total RNA as a template.
(a) Synthesis of 1st Strand cDNA A reaction solution having a composition of 5 μg/3 μL of the total RNA, 1 μL of 5'CDS, and 1 μL of SMART oligo was incubated at 70° C. for 2 minutes, then 2 μL of 5× buffer, 1 μL of DTT, 1 μL of DNTP mix, and 1 μL of Superscript II were added, and then the resultant mixture was incubated at 42° C. for 15 hours. After 100 μL of Tricine Buffer was added, the resultant mixture was incubated at 72° C. for 7 minutes to obtain 1st strand cDNA.
(b) Amplification by PCR of Heavy Chain Genes and Light Chain Genes and Construction of Recombinant Antibody Expression Vectors KOD-Plus cDNA of Toyobo was used for amplification of cDNA.

A reaction solution having a composition of 15 μL of cDNA, 5 μL of 10×KOD-Plus Buffer, 5 μL of dNTP mix, 1 μL of KOD-Plus, 3 μL of 25 mM MgSO₄, primer 1, and primer 2 was prepared in a final volume of 50 μL with double distilled water and subjected to PCR.

Regarding K3, 1-40-1, 3-69-6, and C2, experimental examples are specifically shown below.
K3

For amplification of the light chain, UMP and an hk-2 (5'-GTT GAA GCT CTT TGT GAC GGG CGA GC-3' (SEQ ID NO: 1)) primer were used and a cycle of 94° C. for 5 seconds and 72° C. for 3 minutes was repeated 5 times, then a cycle of 94° C. for 5 seconds, 70° C. for 10 seconds, and 72° C. for 3 minutes was repeated 5 times, and further a cycle of 94° C. for 5 seconds, 68° C. for 10 seconds, and 72° C. for 3 minutes was repeated 25 times. Further, 1 μL of a 5-time diluted solution of this reaction solution was used as a template, NUMP and a hk5 (5'-AGG CAC ACA ACA GAG GCA GTT CCA GAT TTC-3' (SEQ ID NO: 2)) primer were used, and a cycle of 94° C. for 15 seconds, 60° C. for 30 seconds, and 68° C. for 1 minute was repeated 30 times. This reaction solution was subjected to 2% agarose gel electrophoresis, and the amplified PCR product was purified with a QIA quick gel extraction kit (manufactured by Quiagen). The purified PCR product was ligated to a pCR4Blunt-TOPO vector (manufactured by Invitrogen) for subcloning in accordance with the attached instruction manual. T3 (5'-ATT AAC CCT CAC TAA AGG GA-3' (SEQ ID NO: 3)) and the hk5 were then used as primers to determine the nucleotide sequence. Based on the sequence information, DNPL15Bglp (5'-AGA GAG AGA GAT CTC TCA CCA TGG AAG CCC CAG CTC AGC TTC TCT-3' (SEQ ID NO: 4)) was synthesized. The light chain gene subcloned using the pCR4Blunt-TOPO vector was used as a template, the DNPL15Bglp and a 202LR (5'-AGA GAG AGA GCG TAC GTT TAA TCT CCA GTC GTG TCC CTT GGC-3' (SEQ ID NO: 5)) primer were used, and a cycle of 94° C. for 15 seconds, 55° C. for 30 seconds, and 68° C. for 1 minute was repeated 30 times. This reaction solution was subjected to 2% agarose gel electrophoresis, and a fragment of about 400 bp was purified by a QIAquick gel extraction kit (manufactured by Quiagen). The amplified light chain cDNA fragment was digested with BglII and BsiWI and the digested product was introduced into an N5KG1-Val Lark vector (IDEC Pharmaceuticals, a modified vector of N5KG1 (U.S. Pat. No. 6,001,358)) that had been cleaved by the same enzymes. The vector thus obtained was named N5KG1-Val K3L.

For amplification of the heavy chain, UMP and an IgG1p (5'-TCT TGT CCA CCT TGG TGT TGC TGG GCT TGT G-3' (SEQ ID NO: 6)) primer were used, and a cycle of 94° C. for 5 seconds and 72° C. for 3 minutes was repeated 5 times, then a cycle of 94° C. for 5 seconds, 70° C. for 10 seconds, and 72° C. for 3 minutes was repeated 5 times, further a cycle of 94° C. for 5 seconds, 68° C. for 10 seconds, and 72° C. for 3 minutes was repeated 25 times. Further, 1 μL of a 5-time diluted solution of this reaction solution was used as a template, NUMP and IgG2p (5'-TGC ACG CCG CTG GTC AGG GCG CCT GAG TTC C-3' (SEQ ID NO: 7)) were used, and a cycle of 94° C. for 15 seconds, 60° C. for 30 seconds, and 68° C. for 1 minute was repeated 30 times. This reaction solution was subjected to 2% agarose gel electrophoresis, and the amplified PCR product was purified by the QIAquick gel extraction kit. The purified PCR product was ligated to the pCR4Blunt-TOPO vector for subcloning. T3 and hh2 (5'-GCT GGA GGG CAC GGT CAC CAC GCT G-3' (SEQ ID NO: 8)) were then used as primers to determine the nucleotide sequence. Based on the sequence information, K3HcSalI (5'-AGA GAG AGA GGT CGA CCA CCA TGG GGT CAA CCG CCA TCC TCG CCC TCC TC-3' (SEQ ID NO: 9)) was synthesized. The heavy chain gene subcloned using the pCR4Blunt-TOPO vector was used as a template, K3HcSalI and F24HNhe (5'-AGA GAG AGA GGC TAG CTG AGG AGA CGG TGA CCA GGG TTC-3' (SEQ ID NO: 10)) were used, and a cycle of 94° C. for 15 seconds, 55° C. for 30 seconds, and 68° C. for 1 minute was repeated 25 times. This reaction solution was subjected to 2% agarose gel electrophoresis, and a fragment of about 450 bp was purified by the QIAquick gel extraction kit. The amplified heavy chain cDNA fragment was digested with SalI and NheI, and the digested product was introduced into the N5KG1-Val K3L that had been cleaved by the same enzymes. The DNA nucleotide sequence of the inserted portion was determined and it was confirmed that the sequence that had been amplified by PCR and inserted was identical to the gene sequence used as a template. The obtained vector was named N5KG1-Val K3IgG1. Whether or not a recombinant K3 antibody obtained by introducing the N5KG1-Val K3IgG1 into FreeStyle293 cells described below was identical to the antibody derived from a K3 hybridoma was confirmed by determining the binding activity to the hCD98/hLAT1-expressing cell line.

1-40-1

For amplification of the heavy chain, UMP and an IgG1p primer were used, and a cycle of 94° C. for 5 seconds and 72° C. for 3 minutes was repeated 5 times, then a cycle of 94° C. for 5 seconds, 70° C. for 10 seconds, and 72° C. for 3 minutes was repeated 5 times, further a cycle of 94° C. for 5 seconds, 68° C. for 10 seconds, and 72° C. for 3 minutes was repeated 25 times. Further, 1 µL of a 5-time diluted solution of this reaction solution was used as a template, NUMP and an IgG2p primer were used, and a cycle of 94° C. for 15 seconds, 60° C. for 30 seconds, and 68° C. for 1 minute was repeated 30 times. This reaction solution was subjected to 0.8% agarose gel electrophoresis, and the amplified PCR product was purified by the QIAquick gel extraction kit. The purified PCR product was ligated to the pCR4Blunt-TOPO vector for subcloning. T3 and hh2 were then used as primers to determine the nucleotide sequence. Based on the sequence information, 205HP5SalI (5'-AGA GAG AGA GGT CGA CCA CCA TGG AGT TTG GGC TGA GCT GGG TTT-3' (SEQ ID NO: 11)) was synthesized, and the heavy chain gene subcloned using the pCR4Blunt-TOPO vector was used as a template, 205HP5SalI and the F24Hnhe primer were used, and a cycle of 94° C. for 15 seconds, 55° C. for 30 seconds, and 68° C. for 1 minute was repeated 25 times. This reaction solution was subjected to 2% agarose gel electrophoresis, and a fragment of about 450 bp was purified by the QIAquick gel extraction kit. The amplified heavy chain cDNA fragment was digested with SalI and NheI and the digested product was introduced into the N5KG1-Val Lark vector that had been cleaved by the same enzymes. The obtained vector was named N5KG1-Val 1-40-1H.

For amplification of the light chain, UMP and the hk-2 primer were used, and a cycle of 94° C. for 5 seconds and 72° C. for 3 minutes was repeated 5 times, then a cycle of 94° C. for 5 seconds, 70° C. for 10 seconds, and 72° C. for 3 minutes was repeated 5 times, further a cycle of 94° C. for 5 seconds, 68° C. for 10 seconds, and 72° C. for 3 minutes was repeated 25 times. Further, 1 µL of a 5-time diluted solution of this reaction solution was used as a template, NUMP and the hk5 were used, and a cycle of 94° C. for 15 seconds, 60° C. for 30 seconds, and 68° C. for 1 minute was repeated 30 times. This reaction solution was subjected to 2% agarose gel electrophoresis, and the amplified PCR product was purified by the QIAquick gel extraction kit. The purified PCR product was ligated to the pCR4Blunt-TOPO vector for subcloning. T3 and hk5 were then used as primers to determine the nucleotide sequence. Based on the sequence information, A27RN202 (5'-AGA GAG AGA GCG TAC GTT TGA TTT CCA CCT TGG TCC CTT GGC-3' (SEQ ID NO: 12)) was synthesized, and the light chain gene subcloned using the pCR4Blunt-TOPO vector was used as a template, the DNPL15Bglp and the A27RN205 were used, and a cycle of 94° C. for 15 seconds, 55° C. for 30 seconds, and 68° C. for 1 minute was repeated 25 times. This reaction solution was subjected to 2% agarose gel electrophoresis, and a fragment of about 400 bp was purified by the QIAquick gel extraction kit. The amplified light chain cDNA fragment was digested with BglII and BsiWI and the digested product was introduced into the N5KG1-Val 1-40-1H vector that had been cleaved by the same enzymes. The DNA nucleotide sequence of the inserted portion was determined and it was confirmed that the sequence that had been amplified by PCR and inserted was identical to the gene sequence used as a template. The obtained vector was named N5KG1-Val 1-40-1IgG1. Whether or not a recombinant 1-40-1 antibody obtained by introducing the N5KG1-Val 1-40-1IgG1 into the FreeStyle293 cells described below was identical to the antibody derived from a 1-40-1 hybridoma was confirmed by determining the binding activity to the hCD98/hLAT1-expressing cell line.

3-69-6

For amplification of the light chain, UMP and the hk-2 primer were used, a cycle of 94° C. for 15 seconds and 72° C. for 3 minutes was repeated 5 times, then a cycle of 94° C. for 15 seconds, 70° C. for 10 seconds, and 72° C. for 3 minutes was repeated 5 times, further a cycle of 94° C. for 15 seconds, 68° C. for 15 seconds, and 72° C. for 3 minutes was repeated 25 times. Further, 2 µL of a 5-time diluted solution of this reaction solution was used as a template, NUMP and the hk5 were used, and a cycle of 94° C. for 15 seconds, 60° C. for 30 seconds, and 68° C. for 1 minute was repeated 30 times. This reaction solution was subjected to 0.8% agarose gel electrophoresis, and the amplified PCR product was purified by the QIAquick gel extraction kit. The purified PCR product was ligated to the pCR4Blunt-TOPO vector for subcloning. A M13Foward(−20) primer (5'-GTA AAA CGA CGG CCA G-3' (SEQ ID NO: 13)), a M13 Reverse primer (5'-CAG GAA ACA GCT ATG AC-3' (SEQ ID NO: 14)), and the hk5 (5'-AGG CACACA ACA GAG GCAG TTCCAGA TTT C-3' (SEQ ID NO: 2)) were then used as primers to determine the nucleotide sequence. Based on the sequence information, A27_F (5'-AGA GAG AGA GAT CTC TCA CCA TGG AAA CCC CAG CGCAGC TTC TCT TC-3' (SEQ ID NO: 15)) and 39_20_L3Bsi (5'-AGA GAG AGA GCG TAC GTT TGA TCT CCA GCT TGG TCC CCT G-3' (SEQ ID NO: 16)) were synthesized. The light chain gene subcloned using the pCR4Blunt-TOPO vector was used as a template, the A27_F and the 39_20_L3Bsi were used, a cycle of 94° C. for 30 seconds, 55° C. for 30 seconds, and 68° C. for 1 minute was repeated 25 times. This reaction solution was subjected to 0.8% agarose gel electrophoresis, and a fragment of about 400 bp was purified by the QIAquick gel extraction kit. The amplified light chain cDNA fragment was digested by BglII and BsiWI and the digested product was introduced into the N5KG1-Val Lark vector that had been cleaved by the same enzymes. The obtained vector was named N5KG1-Val 3-69-6L.

For amplification of the heavy chain, UMP and the IgG1p (5'-TCT TGT CCA CCT TGG TGT TGC TGG GCT TGT G-3' (SEQ ID NO: 6)) primer were used, a cycle of 94° C. for 15 seconds, and 72° C. for 3 minutes was repeated 5 times, then a cycle of 94° C. for 15 seconds, 70° C. for 10 seconds, and 72° C. for 3 minutes was repeated 5 times, further a cycle of 94° C. for 15 seconds, 68° C. for 15 seconds, and 72° C. for 3 minutes was repeated 30 times. Further, 2 μL of a 5-time diluted solution of this reaction solution was used as a template, NUMP and IgG2p (IgG1.3.4)(5'-TGC ACG CCG CTG GTCAGG GCG CCT GAG TTC C-3' (SEQ ID NO: 7)) were used, a cycle of 94° C. for 30 seconds, 55° C. for 30 seconds, and 68° C. for 1 minute was repeated 25 times. This reaction solution was subjected to 0.8% agarose gel electrophoresis, and the amplified PCR product was purified by the QIAquick gel extraction kit. The purified PCR product was ligated to the pCR4Blunt-TOPO vector for subcloning. The M13F, M13R, and IgG2p were then used as primers to determine the nucleotide sequence. Based on the sequence information, Z3HP5Sal (5'-AGA GAG AGA GGT CGA CCCACCATG GAC TGG AGCATC CTT TT-3' (SEQ ID NO: 17)) and F24HNhe (5'-AGA GAG AGA GGC TAG CTG AGG AGA CGG TGA CCA GGG TTC-3' (SEQ ID NO: 10)) were synthesized. The heavy chain gene subcloned using the pCR4Blunt-TOPO vector was used as a template, the Z3HP5SalF and the F24HNhe were used, a cycle of 94° C. for 30 seconds, 55° C. for 30 seconds, and 68° C. for 1 minute second was repeated 25 times. This reaction solution was subjected to 0.8% agarose gel electrophoresis, and a fragment of about 450 bp was purified by the QIAquick gel extraction kit. The amplified heavy chain cDNA fragment was digested with SalI and NheI and the digested product was introduced into the N5KG1-Val 3-69-6L vector that had been cleaved by the same enzymes. The DNA nucleotide sequence of the inserted portion was determined and it was confirmed that the sequence that had been amplified by PCR and inserted was identical to the gene sequence used as a template. The obtained vector was named N5KG1-Val 3-69-6IgG1. Whether or not a recombinant 3-69-6 antibody obtained by transfecting the N5KG1-Val 3-69-6IgG1 into the FreeStyle293 cells described below was identical to the antibody derived from a 3-69-6 hybridoma was confirmed by determining the binding activity to the hCD98/hLAT1-expressing cell line.

C2IgG1

Since the subclass of the hybridoma-producing C2 is IgM, a C2 antibody variable region (C2 IgG1) was isolated by PCR using a primer that was designed to contain a variable region assumed from IgG derived from the same germ line.

For amplification of the light chain, UMP and the hk-2 primer were used, a cycle of 94° C. for 5 seconds, and 72° C. for 3 minutes was repeated 5 times, then a cycle of 94° C. for 5 seconds, 70° C. for 10 seconds, and 72° C. for 3 minutes was repeated 5 times, further a cycle of 94° C. for 5 seconds, 68° C. for 10 seconds, and 72° C. for 3 minutes was repeated 25 times. Further, 1 μL of a 5-time diluted solution of this reaction solution was used as a template, NUMP and the hk5 were used, and a cycle of 94° C. for 15 seconds, 60° C. for 30 seconds, and 68° C. for 1 minute was repeated 30 times. This reaction solution was subjected to 0.8% agarose gel electrophoresis, and the amplified PCR product was purified by the QIAquick gel extraction kit. The purified PCR product was ligated to the pCR4Blunt-TOPO vector for subcloning. The M13F, M13R, and hk5 were then used as primers to determine the nucleotide sequence. Based on the sequence information, C2-1 Lc Bgl II F (5'-AGA GAG AGA GAT CTC TCA CCA TGG AAA CCC CAG CGCAGC TTC TCT TC 3' (SEQ ID NO: 18)) and C2-1 Lc BsiWI R (5'-AGA GAG AGA GCG TAC GTT TGA TAT CCA CTT TGG TCC CAG GG-3' (SEQ ID NO: 19)) were synthesized. The light chain gene subcloned using the pCR4Blunt-TOPO vector was used as a template, the C2-1 Lc Bgl II F and the C2-1 Lc BsiWI R were used, and a cycle of 94° C. for 15 seconds, 60° C. for 30 seconds, and 68° C. for 1 minute was repeated 25 times. This reaction solution was subjected to 0.8% agarose gel electrophoresis, and a fragment of about 400 bp was purified by the QIAquick gel extraction kit. The amplified light chain cDNA fragment was digested with BglII and BsiWI and the digested product was introduced into the N5KG1-Val Lark vector that had been cleaved by the same enzymes. The obtained vector was named N5KG1-Val C2L.

For amplification of the heavy chain, UMP and the M655R (5'-GGC GAA GAC CCG GAT GGC TAT GTC-3' (SEQ ID NO: 20)) primer were used, and a cycle of 94° C. for 15 seconds, 60° C. for 30 seconds, and 68° C. for 1 minute was repeated 30 times. Further, 1 μL of a 5-time diluted solution of this reaction solution was used as a template, NUMP and the M393R (5'-AAA CCC GTG GCC TGG CAG ATG AGC-3' (SEQ ID NO: 21)) were used, and a cycle of 94° C. for 15 seconds, 60° C. for 30 seconds, and 68° C. for 1 minute was repeated 30 times. This reaction solution was subjected to 0.8% agarose gel electrophoresis, and the amplified PCR product was purified by the QIAquick gel extraction kit. The purified PCR product was ligated to the pCR4Blunt-TOPO vector for subcloning. The M13Foward (−20) primer (5'-GTA AAA CGA CGG CCA G-3' (SEQ ID NO: 13)), the M13 Reverse primer (5'-CAG GAA ACA GCT ATG AC-3' (SEQ ID NO: 14)), and the M393R were then used as primers to determine the nucleotide sequence. Based on the sequence information, C2hcSalIF (5'-AGA GAG AGA GGT CGA CCA CCA TGA AGCACC TGT GGT TCT TCC TCC TGC T-3' (SEQ ID NO: 22)) and C2hcNheI (5'-AGA GAG AGA GGC TAG CTG AGG AGA CGG TGA CCA GGG TTC CCT GG-3' (SEQ ID NO: 58)) were synthesized. The heavy chain gene subcloned using the pCR4Blunt-TOPO vector was used as a template, C2hcSalIF and C2hcNheI were used, a cycle of 94° C. for 15 seconds, 60° C. for 30 seconds, and 68° C. for 30 seconds was repeated 25 times. This reaction solution was subjected to 0.8% agarose gel electrophoresis, and a fragment of about 450 bp was purified by the QIAquick gel extraction kit. The amplified heavy chain cDNA fragment was digested with SalI and NheI and the digested product was introduced into the N5KG1-Val C2L vector that had been cleaved by the same enzymes. The DNA nucleotide sequence of the inserted portion was determined and it was confirmed that the sequence that had been amplified by PCR and inserted was identical to the gene sequence used as a template. The obtained vector was named N5KG1-Val C2IgG1.

C2IgG1NS

The frame region of the heavy chain in the C2IgG1 gene cloned as described above contained a mutation that is not observed in the original germ line. A C2 variable region sequence having a sequence of the original germ line was thus isolated by the method described below.

The vector N5KG1-Val C2IgG1 obtained above was used as a template and the C2hc NS F (5'-CGT CCA AGA ACC AGT TCT CCC TGA AGC TGA-3' (SEQ ID NO: 23)) primer and the C2hc NS R (5'-TCA GCT TCA GGG AGA ACT GGT TCT TGG ACG-3' (SEQ ID NO: 24)) primer were used to replace G and T at positions 290 and 299 of the C2 antibody heavy chain with A and C, respectively, to prepare N5KG1-Val C2IgG1NS. Whether or not the recombinant C2IgG1 and C2IgG1NS antibodies that were obtained by introducing the N5KG1-Val C2IgG1 and the N5KG1-Val C2IgG1NS into the FreeStyle293 cells described below, respectively, had the same specificity as that of the IgM antibody derived from the C2 hybridoma was confirmed by determination of the binding activity to the hCD98/hLAT1-expressing cell line. The binding activities of the C2IgG1 and the C2IgG1NS were almost the same.

C2IgμG1

Since the forms of binding sites of the heavy chain and the light chain might differ from those of the original IgM when the method used in the above C2IgG1 was used, the sequence conversion described below was conducted. In other words, 26 amino acids contiguous in the variable region side to a common sequence (GCL sequence) in the CH1 constant region of the γ chain of IgG and the μ chain of IgM were used as a μ chain sequence and all amino acids in the constant region side of the GCL sequence was converted into γ chain (C2 IgμG1). The above sequence conversion was conducted by the method described below.

For amplification of the heavy chain of C2 cDNA, UMP and the M655R primer were used, and a cycle of 94° C. for 15 seconds, 60° C. for 30 seconds, and 68° C. for 1 minute was repeated 30 times. Further, 1 μL of a 5-time diluted solution of this reaction solution was used as a template, NUMP and the M393R were used, and a cycle of 94° C. for 15 seconds, 60° C. for 30 seconds, and 68° C. for 1 minute was repeated 30 times. This reaction solution was subjected to 0.8% agarose gel electrophoresis, and the amplified PCR product was purified by the QIAquick gel extraction kit. The purified PCR product was ligated to the pCR4Blunt-TOPO vector for subcloning. The M13Foward(−20) primer (5'-GTA AAA CGA CGG CCA G-3' (SEQ ID NO: 13)), the M13 Reverse primer (5'-CAG GAA ACA GCT ATG AC-3' (SEQ ID NO: 14)), and the M393R were then used as primers to determine the nucleotide sequence. Based on the sequence information, C2hcSalIF (5'-AGA GAG AGA GGT CGA CCA CCA TGA AGC ACC TGT GGT TCT TCC TCC TGC T-3' (SEQ ID NO: 22)) and Mu-GCL-Gamma L(5'-CAC CGG TTC GGG GAA GTA GTC CTT GAC GAG GCAGCA AAC GGC CAC GCT GCT CGT-3' (SEQ ID NO: 25)) were synthesized. The heavy chain gene subcloned using the pCR4Blunt-TOPO vector was used as a template, the C2hcSalIF and the Mu-GCL-Gamma L were used, and a cycle of 94° C. for 15 seconds, 60° C. for 30 seconds, and 68° C. for 1 minute was repeated 25 times. This reaction solution was subjected to 0.8% agarose gel electrophoresis, and the PCR amplification product was purified by the QIAquick gel extraction kit. This PCR amplification product was named C2Vμ. The N5KG1-Val Lark vector was then used as a template, Mu-GCL-Gamma U (5'-ACG AGCAGC GTG GCC GTT GGC TGC CTC GTCAAG GAC TAC TTC CCC GAA CCG GTG-3' (SEQ ID NO: 26)) and hIgG1 BamHI L (5'-CGC GGA TCC TCA TCA TTT ACC CGG AGA CAG GGA GAG GCT-3' (SEQ ID NO: 27)) were used, a cycle of 94° C. for 15 seconds, 60° C. for 30 seconds, and 68° C. for 90 seconds was repeated 25 times. This reaction solution was subjected to 0.8% agarose gel electrophoresis, and the PCR amplification product was purified by the QIAquick gel extraction kit. This PCR amplification product was named Cγ1. Each 5 μL of 3-time diluted solutions of the C2Vμ and the Cγ1 was placed, and a cycle of 94° C. for 15 seconds, 55° C. for 30 seconds, and 68° C. for 2 minutes was repeated 3 times in the absence of a primer. This reaction solution was heated at 99° C. for 5 minutes and then diluted 10 times. 5 μL of the diluted solution was used as a template, the C2hcSalIF and the hIgG1 BamHI L were used, and a cycle of 94° C. for 15 seconds, 60° C. for 30 seconds, and 68° C. for 2 minutes was repeated 25 times. This reaction solution was subjected to 0.8% agarose gel electrophoresis, and the PCR amplification product was purified by the QIAquick gel extraction kit. This PCR-amplified DNA fragment was digested with SalI and SmaI and the digested product was introduced into the N5KG1-Val Lark vector that had been cleaved by the same enzymes and containing the C2 light chain gene described above. The DNA nucleotide sequence of the inserted portion was determined and it was confirmed that the sequence that had been amplified by PCR and inserted was identical to the gene sequence used as a template. The obtained vector was named N5KG1-Val C2IgμG1. The binding activity of the C2IgμG1 antibody was determined by determining the binding activity of the recombinant obtained by gene introduction of the N5KG1-Val C2IgμG1 into the FreeStyle293 cells described below to the hCD98/hLAT1-expressing cell line.

The DNA sequences containing the heavy chain variable region and the light chain variable region of K3, 1-40-1, and 3-69-6 and the amino acid sequences containing the heavy chain variable region and the light chain variable region were sequences represented by the following sequence numbers, respectively.

<Nucleotide Sequence of the K3 Heavy Chain Variable Region> (SEQ ID NO: 28)

```
AGAGAGAGAGGTCGACCACCATGGGGTCAACCGCCATCCTCGCCCTC
CTCCTGGCTGTTCTCCAAGGAGTCTGTGCCGAGGTGCAGCTGGTGCA
GTCTGGAGCAGAAGTGAAAAAGCCCGGGGAGTCTCTGAAGATCTCCT
GTAAGGGTTCTGGATACAGGTTTACCGACTACTGGATCGGCTGGGTGC
GCCAGATGCCCGGGAAAGGCCTGGAGTGGATGGGGATCTTCTATCCT
GGTGACTCTGATGCCAGATACAGCCCGTCCTTCCAAGGCCAGGTCAC
CATCTCAGCCGACAAGTCCATCAACACCGCCTACCTGCAGTGGAGCA
GCCTGAAGGCCTCGGACACCGCCATGTATTATTGTGCGAGACGGCGA
GATATAGTGGGAGGTACTGACTACTGGGGCCAGGGAACCCTGGTCAC
CGTCTCCTCA
```

<Amino Acid Sequence of the K3 Heavy Chain Variable Region> (SEQ ID NO: 29)

```
MGSTAILALLLAVLQGVCAEVQLVQSGAEVKKPGESLKISCKGSGYRFT
DYWIGWVRQMPGKGLEWMGIFYPGDSDARYSPSFQGQVTISADKSIN
TAYLQWSSLKASDTAMYYCARRRDIVGGTDYWGQGTLVTVSS
```

<Nucleotide Sequence of the K3 Light Chain Variable Region> (SEQ ID NO: 30)

```
AGAGAGAGAGATCTCTCACCATGGAAGCCCCAGCTCAGCTTCTCTTCC
TCCTGCTACTCTGGCTCCCAGATACCACCGGAGAAATTGTGTTGACAC
AGTCTCCAGCCACCCTGTCTTTGTCTCCAGGGGAAAGAGCCACCCTCT
CCTGCAGGGCCAGTCAGAGTGTTAGCAGCTACTTAGACTGGTACCAA
CAGAAACCTGGCCAGGCTCCCAGGCTCCTCATCTATGATGCATCCAGC
```

AGGGCCACTGGCATCCCAGCCAGGTTCAGTGGCAGTGGGTCTGGGA

CAGACTTCACTCTCACCATCAGCAGCCTAGAGCCTGAAGATTTTGCAG

TTTATTACTGTCAGCAGCGTAGCAACTGGATCACCTTCGGCCAAGGGA

CACGACTGGAGATTAAA

<K3 Light Chain Variable Region> (SEQ ID NO: 31)

MEAPAQLLFLLLLWLPDTTGEIVLTQSPATLSLSPGERATLSCRASQSVS
SYLDWYQQKPGQAPRLLIYDASSRATGIPARFSGSGSGTDFTLTISSLEP
EDFAVYYCQQRSNWITFGQGTRLEIK

<Nucleotide Sequence of the 1-40-1 Heavy Chain Variable Region> (SEQ ID NO: 32)

AGAGAGAGAGGTCGACCACCATGGAGTTTGGGCTGAGCTGGGTTTTC

CTTGTTGCTATTTTAAAAGGTGTCCAGTGTGAGGTGCAGCTGGTGGAG

TCTGGGGGAGGTGTGGTACGGCCTGGGGGGTCCCTGAGACTCTCCT

GTGCAGCCTCTGGATTCACCTTTGATGATTATGGCATGACCTGGGTCC

GCCAAGCTCCAGGGAAGGGGCTGGAGTGGGTCTCTACTATTAGTTGG

AATGGTGGTGGCACAGGTTATGCAGACTCTGTGAAGGGCCGATTCAC

CATCTCCAGAGACAACGCCAAGAACTCCCTGTATCTGCAAATGAACAG

TCTGAGAGCCGAGGACACGGCCTTGTATTACTGTGCGGGATATTGTAT

TATTACCGGCTGCTATGCGGACTACTGGGGCCAGGGAACCCTGGTCA

CCGTCTCCTCA

<Amino Acid Sequence of the 1-40-1 Heavy Chain Variable Region> (SEQ ID NO: 33)

MEFGLSWVFLVAILKGVQCEVQLVESGGGVVRPGGSLRLSCAASGFTF
DDYGMTWVRQAPGKGLEWVSTISWNGGGTGYADSVKGRFTISRDNA
KNSLYLQMNSLRAEDTALYYCAGYCIITGCYADYWGQGTLVTVSS

<Nucleotide Sequence of the 1-40-1 Light Chain Variable Region> (SEQ ID NO: 34)

AGAGAGAGAGATCTCTCACCATGGAAGCCCCAGCTCAGCTTCTCTTCC

TCCTGCTACTCTGGCTCCCAGATACCACCGGAGAAATTGTGTTGACAC

AGTCTCCAGCCACCCTGTCTTTGTCTCCAGGGGAAAGAGCCACCCTCT

CCTGCAGGGCCAGTCAGAGTGTTAGCAGCTACTTAGCCTGGTACCAA

CAGAAACCTGGCCAGGCTCCCAGGCTCCTCATCTATGATGCATCCAAC

AGGGCCACTGGCATCCCAGCCAGGTTGAGTGGCAGTGGGTCTGGGA

CAGACTTCACTCTCACCATCAGCAGCCTAGAGCCTGAAGATTTTGCAG

TTTATTACTGTCAGCAGCGTAGCAACTGGTGGACGTTCGGCCAAGGGA

CCAAGGTGGAAATCAAA

<Amino Acid Sequence of the 1-40-1 Light Chain Variable Region> (SEQ ID NO: 35)

MEAPAQLLFLLLLWLPDTTGEIVLTQSPATLSLSPGERATLSCRASQSVS
SYLAWYQQKPGQAPRLLIYDASNRATGIPARFSGSGSGTDFTLTISSLEP
EDFAVYYCQQRSNWWTFGQGTKVEIK

<Nucleotide Sequence of the 3-69-6 Heavy Chain Variable Region> (SEQ ID NO: 36)

GTCGACCCACCATGGACTGGACCTGGAGCATCCTTTTCTTGGTGGCA

GCAGCAACAGGTGCCCACTCCCAGGTTCAACTGGTGCAGTCTGGAGC

TGAGGTGAAGAAGCCTGGGGCCTCAGTGAAGGTCTCCTGTAAGGCTT

CTGGTTACACCTTTACCAGCTATGGTATCAGCTGGATGCGACAGGCCC

CTGGACAAGGGCTTGAGTGGATGGGATGGATCAGCGCTTACAATGGT

AATACGAACTATGTACAGAAGTTCCAGGACAGAGTCACCATGACCAGA

GACACATCCACGAGCACAGCCTACATGGAGCTGAGGAGCCTGAGATC

TGACGACACGGCCGTGTATTACTGTGCGAGAGATCGGGGCAGCAATT

GGTATGGGTGGTTCGACCCCTGGGGCCAGGGAACCCTGGTCACCGT

CTCCTCA

<3-69-6 Heavy Chain Variable Region> (SEQ ID NO: 37)

RRPTMDWTWSILFLVAAATGAHSQVQLVQSGAEVKKPGASVKVSCKAS
GYTFTSYGISWMRQAPGQGLEWMGWISAYNGNTNYVQKFQDRVTMT
RDTSTSTAYMELRSLRSDDTAVYYCARDRGSNWYGWFDPWGQGTLVT
VSS

<Nucleotide Sequence of the 3-69-6 Light Chain Variable Region> (SEQ ID NO: 38)

AGATCTCTCACCATGGAAACCCCAGCGCAGCTTCTCTTCCTCCTGCTA

CTCTGGCTCCCAGATACCACCGGAGAAATTGTGTTGACGCAGTCTCCA

GGCACCCTGTCTTTGTCTCCAGGGGAAAGAGCCACCCTCTCCTGCAG

GGCCAGTCAGAGTGTTAGCAGCAGCTACTTAGCCTGGTACCAGCAGA

AACCTGGCCAGGCTCCCAGGCTCCTCATCTATGGTGCATCCAGCAGG

GCCACTGGCATCCCAGACAGGTTCAGTGGCAGTGGGTCTGGGACAG

ACTTCACTCTCACCATCAGCAGACTGGAGCCTGAAGATTTTGCAGTGT

ATTACTGTCAGCAGTATGGTAGCTCGTACACTTTTGGCCAGGGGACCA

AGCTGGAGATCAAA

<Amino Acid Sequence of the 3-69-6 Light Chain Variable Region> (SEQ ID NO: 39)

RSLTMETPAQLLFLLLLWLPDTTGEIVLTQSPGTLSLSPGERATLSCRAS
QSVSSSYLAWYQQKPGQAPRLLIYGASSRATGIPDRFSGSGSGTDFTLTI
SRLEPEDFAVYYCQQYGSSYTFGQGTKLEIK

The DNA sequences containing the C2 heavy chain variable region and the light chain variable region and the amino acid sequences containing the heavy chain variable region and the light chain variable region are shown below, respectively.

5<Nucleotide Sequence of the C2IgG1 Heavy Chain Variable Region> (SEQ ID NO: 40)

GTCGACCACCATGAAGCACCTGTGGTTCTTCCTCCTGCTGGTGGCGG

CTCCCAGATGGGTCCTGTCCCAGCTGCAGCTGCAGGAGTCGGGCCCA

GGACTGGTGAAGCCTTCGGAGACCCTGTCCCTCACCTGCACTGTCTC

TGGTGGCTCCATCAGCAGTAGTAGTTACTACTGGGGCTGGATCCGCCA

GCCCCCAGGGAAGGGGCTGGAGTGGATTGGGAGTATCTATTATAGTG

GGAGTACCTACTACAACCCGTCCCTCAAGAGTCGAGTCACCATATCCG

TAGACACGTCCAAGAGCCAGTTCTTCCTGAAGCTGAGCTCTGTGACC

GCCGCAGACACGGCTGTGTATTACTGTGCGAGACAAGGGACGGGGC

TCGCCCTATTTGACTACTGGGGCCAGGGAACCCTGGTCACCGTCTCCT

CA

<Amino Acid Sequence of the C2IgG1 Heavy Chain Variable Region> (SEQ ID NO: 41)

STTMKHLWFFLLLLVAAPRWVLSQLQLQESGPGLVKPSETLSLTCTVSGG

SISSSSYYWGWIRQPPGKGLEWIGSIYYSGSTYYNPSLKSRVTISVDTS

KSQFFLKLSSVTAADTAVYYCARQGTGLALFDYWGQGTLVTVSS

<Nucleotide Sequence of the C2IgG1Ns Heavy Chain Variable Region> (SEQ ID NO: 42)

GTCGACCACCATGAAGCACCTGTGGTTCTTCCTCCTGCTGGTGGCGG

CTCCCAGATGGGTCCTGTCCCAGCTGCAGCTGCAGGAGTCGGGCCCA

GGACTGGTGAAGCCTTCGGAGACCCTGTCCCTCACCTGCACTGTCTC

TGGTGGCTCCATCAGCAGTAGTAGTTACTACTGGGGCTGGATCCGCCA

GCCCCCAGGGAAGGGGCTGGAGTGGATTGGGAGTATCTATTATAGTG

GGAGTACCTACTACAACCCGTCCCTCAAGAGTCGAGTCACCATATCCG

TAGACACGTCCAAGAACCAGTTCTCCCTGAAGCTGAGCTCTGTGACC

GCCGCAGACACGGCTGTGTATTACTGTGCGAGACAAGGGACGGGGC

TCGCCCTATTTGACTACTGGGGCCAGGGAACCCTGGTCACCGTCTCCT

CA

<Amino Acid Sequence of the C2IgG1Ns Heavy Chain Variable Region> (SEQ ID NO: 43)

STTMKHLWFFLLLLVAAPRWVLSQLQLQESGPGLVKPSETLSLTCTVSGG

SISSSSYYWGWIRQPPGKGLEWIGSIYYSGSTYYNPSLKSRVTISVDTS

KNQFSLKLSSVTAADTAVYYCARQGTGLALFDYWGQGTLVTVSS

<Nucleotide Sequence from the C2IgµG1 Heavy Chain Variable Region to the Binding Site to the Human IgG1> (SEQ ID NO: 44)

GTCGACCACCATGAAGCACCTGTGGTTCTTCCTCCTGCTGGTGGCGG

CTCCCAGATGGGTCCTGTCCCAGCTGCAGCTGCAGGAGTCGGGCCCA

GGACTGGTGAAGCCTTCGGAGACCCTGTCCCTCACCTGCACTGTCTC

TGGTGGCTCCATCAGCAGTAGTAGTTACTACTGGGGCTGGATCCGCCA

GCCCCCAGGGAAGGGGCTGGAGTGGATTGGGAGTATCTATTATAGTG

GGAGTACCTACTACAACCCGTCCCTCAAGAGTCGAGTCACCATATCCG

TAGACACGTCCAAGAGCCAGTTCTTCCTGAAGCTGAGCTCTGTGACC

GCCGCAGACACGGCTGTGTATTACTGTGCGAGACAAGGGACGGGGC

TCGCCCTATTTGACTACTGGGGCCAGGGAACCCTGGTCACCGTCTCCT

CAGGGAGTGCATCCGCCCCAACCCTTTTCCCCCTCGTCTCCTGTGAGA

ATTCCCCGTCGGATACGAGCAGCGTGGCCGTT

<Amino Acid Sequence from the C2IgµG1 Heavy Chain Variable Region to the Binding Site to the Human IgG1> (SEQ ID NO: 45)

STTMKHLWFFLLLLVAAPRWVLSQLQLQESGPGLVKPSETLSLTCTVSGG

SISSSSYYWGWIRQPPGKGLEWIGSIYYSGSTYYNPSLKSRVTISVDTS

KSQFFLKLSSVTAADTAVYYCARQGTGLALFDYWGQGTLVTVSSGSASA

PTLFPLVSCENSPSDTSSVAV

<Nucleotide Sequence of the Light Chain Variable Region of C2IgG1 and C2IgµG1> (SEQ ID NO: 46)

AGATCTCTCACCATGGAAACCCCAGCGCAGCTTCTCTTCCTCCTGCTA

CTCTGGCTCCCAGATACCACCGGAGAAATTGTGTTGACGCAGTCTCCA

GGCACCCTGTCTTTGTCTCCAGGGGAAAGAGCCACCCTCTCCTGCAG

GGCCAGTCAGAGTGTTAGCAGCAGCTTCTTAGCCTGGTACCAGCAGA

AACCTGGCCAGGCTCCCAGGCTCCTCATCTATGGTGCATCCAGCAGG

GCCACTGGCATCCCAGACAGGTTCAGTGGCAGTGGGTCTGGGACAG

ACTTCACTCTCACCATCAGCAGACTGGAGCCTGAAGATTTCGCAGTGT

ATTACTGTCAGCAGTATGGTAGCTCACCTATATTCACTTTCGGCCCTGG

GACCAAAGTGGATATCAAA

<Amino Acid Sequence of the Light Chain Variable Region of C2IgG1 and C2IgµG1> (SEQ ID NO: 47)

RSLTMETPAQLLFLLLLWLPDTTGEIVLTQSPGTLSLSPGERATLSCRAS

QSVSSSFLAWYQQKPGQAPRLLIYGASSRATGIPDRFSGSGSGTDFTLTI

SRLEPEDFAVYYCQQYGSSPIFTFGPGTKVDIK

The light chain variable regions and the heavy chain variable regions of K3 and C2IgG1 (namely, nucleic acids of the sequences represented by SEQ ID NOs: 28 and 30 and SEQ ID NOs: 40 and 46) among the above antibody sequences were introduced into the pCR4Blunt-TOPO vector and the resultants were deposited to the International Patent Organism Depositary, National Institute of Advanced Industrial Science and Technology, and given the accession numbers of FERM BP-10552 (indication for identification: K3/pCR4) and FERM BP-10551 (indication for identification: C2IgG1/pCR4).

The respective antibody variable regions contains the heavy chain and the light chain and also the restriction enzyme recognition sequence used for binding and isolation. The light chain variable regions of the respective antibodies can be isolated using restriction enzymes BglII and BsiWI, and the heavy chain variable regions can be isolated using restriction enzymes SalI and NheI. The gene sequences of those containing the respective antibody variable regions inserted into the pCR4Blunt-TOPO vector, the restriction-enzyme restriction site, and the like are shown below.
<K3/pCR4> (SEQ ID NO: 48)

AGAGAGAGAGATCTCTCACCATGGAAGCCCCAGCTCAGCTTCTCTTCC

TCCTGCTACTCTGGCTCCCAGATACCACCGGAGAAATTGTGTTGACAC

AGTCTCCAGCCACCCTGTCTTTGTCTCCAGGGGAAAGAGCCACCCTCT

CCTGCAGGGCCAGTCAGAGTGTTAGCAGCTACTTAGACTGGTACCAA

CAGAAACCTGGCCAGGCTCCCAGGCTCCTCATCTATGATGCATCCAGC

AGGGCCACTGGCATCCCAGCCAGGTTCAGTGGCAGTGGGTCTGGGA

CAGACTTCACTCTCACCATCAGCAGCCTAGAGCCTGAAGATTTTGCAG

TTTATTACTGTCAGCAGCGTAGCAACTGGATCACCTTCGGCCAAGGGA

CACGACTGGAGATTAAACGTACGCTCTCTCTCTAGAGAGAGAGGTCG

ACCACCATGGGGTCAACCGCCATCCTCGCCCTCCTCCTGGCTGTTCTC

CAAGGAGTCTGTGCCGAGGTGCAGCTGGTGCAGTCTGGAGCAGAAG

TGAAAAAGCCCGGGGAGTCTCTGAAGATCTCCTGTAAGGGTTCTGGA

TACAGGTTTACCGACTACTGGATCGGCTGGGTGCGCCAGATGCCCGG

GAAAGGCCTGGAGTGGATGGGGATCTTCTATCCTGGTGACTCTGATG

CCAGATACAGCCCGTCCTTCCAAGGCCAGGTCACCATCTCAGCCGAC

AAGTCCATCAACACCGCCTACCTGCAGTGGAGCAGCCTGAAGGCCTC

GGACACCGCCATGTATTATTGTGCGAGACGGCGAGATATAGTGGGAG

GTACTGACTACTGGGGCCAGGGAACCCTGGTCACCGTCTCCTCAGCT

AGCCTCTCTCT

<C2IgG1/pCR4> (SEQ ID NO: 49)

AGAGAGAGAGATCTCTCACCATGGAAACCCCAGCGCAGCTTCTCTTCC

TCCTGCTACTCTGGCTCCCAGATACCACCGGAGAAATTGTGTTGACGC

AGTCTCCAGGCACCCTGTCTTTGTCTCCAGGGGAAAGAGCCACCCTC

TCCTGCAGGGCCAGTCAGAGTGTTAGCAGCAGCTTCTTAGCCTGGTA

CCAGCAGAAACCTGGCCAGGCTCCCAGGCTCCTCATCTATGGTGCAT

CCAGCAGGGCCACTGGCATCCCAGACAGGTTCAGTGGCAGTGGGTCT

GGGACAGACTTCACTCTCACCATCAGCAGACTGGAGCCTGAAGATTTC

GCAGTGTATTACTGTCAGCAGTATGGTAGCTCACCTATATTCACTTTCG

GCCCTGGGACCAAAGTGGATATCAAACGTACGCTCTCTCTCTAGAGAG

AGAGGTCGACCACCATGAAGCACCTGTGGTTCTTCCTCCTGCTGGTG

GCGGCTCCCAGATGGGTCCTGTCCCAGCTGCAGCTGCAGGAGTCGG

GCCCAGGACTGGTGAAGCCTTCGGAGACCCTGTCCCTCACCTGCACT

GTCTCTGGTGGCTCCATCAGCAGTAGTAGTTACTACTGGGGCTGGATC

CGCCAGCCCCCAGGGAAGGGGCTGGAGTGGATTGGGAGTATCTATTA

TAGTGGGAGTACCTACTACAACCCGTCCCTCAAGAGTCGAGTCACCAT

ATCCGTAGACACGTCCAAGAGCCAGTTCTTCCTGAAGCTGAGCTCTGT

GACCGCCGCAGACACGGCTGTGTATTACTGTGCGAGACAAGGGACG

GGGCTCGCCCTATTTGACTACTGGGGCCAGGGAACCCTGGTCACCGT

CTCCTCAGCTAGCCTCTCTCTCT

Example 7

Preparation of Recombinant Antibody

The recombinant antibody expression vector constructed in Example 6 was introduced into host cells to prepare recombinant antibody-expressing cells. As the host cells for expression, a dhfr-deficient cell line (ATCC CRL-9096) of CHO cells was used. The vector was introduced into the host cells by electroporation. About 2 µg of the antibody expression vector was linearized by restriction enzymes, the gene was introduced into $4\times10^6$ CHO cells under the conditions of 350V and 500 µF using a Bio-Rad electrophoreter, and the cells were inoculated to a 96-well culture plate. The agent corresponding to a selection marker of the expression vector was added and the cells were continuously cultured. After checking appearance of colonies, the antibody-expressing cell line was screened by the method described in Example 4. The antibody was purified from the screened cells in accordance with the method in Example 8. In addition, the recombinant antibody expression vector was introduced into the FreeStyle293 cells (manufactured by Invitrogen) in accordance with the attached instruction manual to express a recombinant antibody.

Example 8

Purification of Antibody

A hybridoma culture supernatant containing human IgG antibody was prepared by the method described below. The antibody-producing hybridoma was acclimated in an eRDF medium (manufactured by Kyokuto Pharmaceutical Industrial Co., Ltd.) containing bovine insulin (5 µg/mL, manufactured by Gibco), human transferin (5 µg/mL, manufactured by Gibco), ethanolamine (0.01 mM, manufactured by Sigma), and sodium selenite ($2.5\times10^{-5}$ mM, manufactured by Sigma). The hybridoma was cultured in a tissue culture flask, and the culture supernatant was collected when the viable rate of the hybridoma was 90%. The collected supernatant was filtered through 10 µm and 0.2 µm filters (manufactured by Gelman Science) to remove contaminants such as the hybridoma and the like. The culture supernatant containing the antibody was affinity-purified using Protein A (manufactured by Amersham), PBS as an absorption buffer, and 20 mM sodium citrate buffer (pH 3.0) as an elution buffer. The elution fractions were adjusted to around pH 6.0 by adding 50 mM sodium phosphate buffer (pH 7.0). The prepared antibody solution was replaced with PBS using a dialysis membrane (10,000 cut, manufactured by Spectrum Laboratories) and filter-sterilized through a membrane filter MILLEX-GV (manufactured by Millpore) having a pore size of 0.22 μm to yield the purified antibody. The concentration of the purified antibody was obtained by measuring the absorbance at 280 nm and converting a measured value at 1.45 Optimal density to 1 mg/mL.

Example 9

Specificities of Each of the Monoclonal Antibodies

Reactivities of the respective monoclonal antibodies obtained in Example 4 were examined by the same method as the FACS analysis clearly described in Example 5. The cell lines prepared in Example 2 were used to prepare a cell suspension at 2×10$^6$/mL using a Staining Buffer (SB) and the cell suspension was dispensed in a 96-well round-bottomed plate (manufactured by Becton Dickinson) at 50 μL/well. The concentration of each of the recombinant antibodies prepared in Example 4 to Example 8 was adjusted to 5 μg/mL using SB, and 50 μL of the antibody solution was added to the respective wells and stirred. An anti-dinitrophenyl (DNP) human IgG1 antibody prepared in KM mice was used as a negative control. After reaction for 30 minutes, the mixture was centrifuged (2000 rpm, 4° C., 2 minutes) to remove the supernatant. The pellets were washed once with 100 μL/well of SB, then a 200-time diluted RPE fluorescently-labeled rabbit anti-human IgK F(ab')$_2$ antibody (manufactured by Dako Cytomation) was added at 50 μL/well and the resultant solution was reacted at ice temperature for 30 minutes. After washing with SB once, the resultant pellets were suspended in 300 μL of SB, the fluorescence intensity showing the binding of the antibody was measured by the FACS.

As a result, all the antibodies exhibited strong binding activity to the hCD98/hLAT1-E-expressing CT26 cells (FIG. 1) or the hCD98/hLAT1-E-expressing L929 cells (FIG. 2), while no binding activity to CT26 cells or L929 cells was observed. Further, any of the antibodies did not bind to the hLAT1-E-expressing L929 cells, but they bound to the hCD98-expressing L929 cells. It was found accordingly that the binding site of the C2, K3, 7-95-8, 10-60-7, 3-69-6, and 1-40-1 antibodies was located at hCD98 (FIG. 2).

Example 10

Regions of hCD98 Protein Involved in Antigen Binding of Each of the Monoclonal Antibodies The region of the hCD98 molecule that is important for binding of each of the monoclonal antibodies was examined.

First, reactivity to a tunicamycin-treated K562 cell line was examined. 2×10$^5$ K562 cells were inoculated to a 6-well plate (4 mL/well) and cultured at 37° C. in 5% CO$_2$ for 72 hours in the presence/absence of 5 μg/mL tunicamycin (manufactured by Sigma). It was confirmed by Western blotting that the molecular weight of hCD98, whose original molecular weight was about 80 Kda, was about 60 kDa under this condition, which corresponded to a theoretical value after removal of the N-linked carbohydrate chain. The cells were collected after culturing and suspended at 2×10$^6$/mL in a Staining Buffer (SB). The cell suspension was dispensed in a 96-well round-bottomed plate (manufactured by Becton Dickinson) at 50 μL/well. Each of the recombinant antibodies prepared at 5 μg/mL using SB was added at 50 μL/well and the resultant solution was reacted at ice temperature for 30 minutes. An anti-DNP human IgG1 antibody was used as a negative control. After washing once with SB, an RPE fluorescently-labeled goat anti-human Igy F(ab')$_2$ antibody (manufactured by SuthernBiotech) diluted 200 times with SB was added and the mixture was incubated at ice temperature for 30 minutes. After washing once with SB, the cells were suspended in 300 μL of FACS buffer, the fluorescence intensity showing the binding of the antibody was measured by the FACS.

Figure 3:
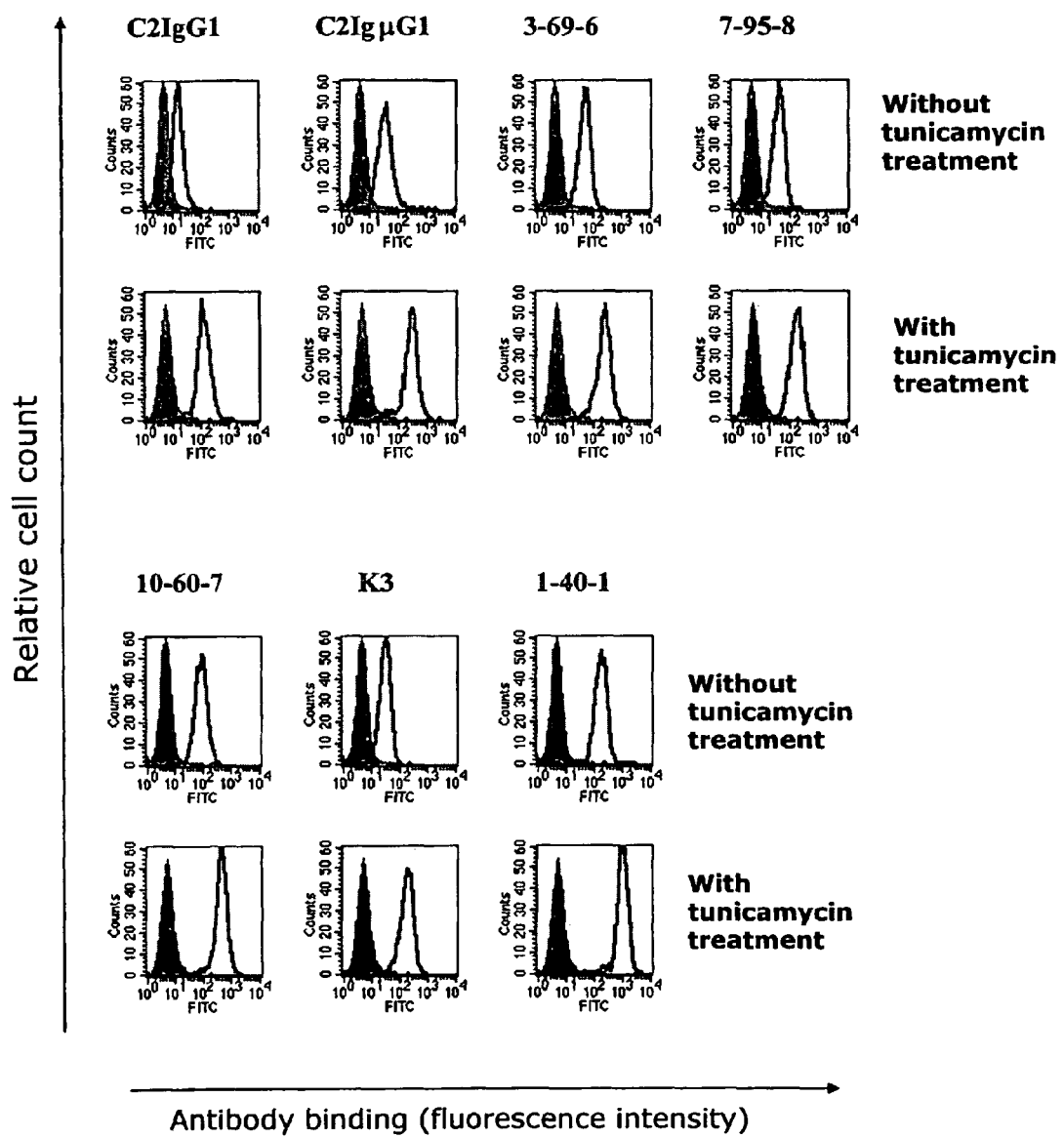
FIG. 3 shows the binding of human anti-CD98 monoclonal antibodies to a tunicamycin-treated K562 human cell line.

As a result, no decrease in binding activity to the tunicamycin-untreated K562 cells as compared with the binding activity to the untreated cells was observed for any of the antibodies (FIG. 3). The above results show that the binding site of the respective antibodies was not the N-linked carbohydrate chain, strongly suggesting that these monoclonal antibodies were an hCD98 antibody. Further, the region of hCD98 that is important for the binding of the respective monoclonal antibodies was examined in Example 11.

Example 11

Region of Human CD98 Protein Important for Binding Reaction of Each of the Antibodies Since each of the antibodies did not have cross-reactivity to mouse CD98 (mCD98), a chimera CD98 prepared by artificially binding of mCD98 and hCD98 was utilized to examine a region of human CD98 protein important for a binding reaction of each of the antibodies.

The chimera CD98 was prepared as described below. Based on the sequence information about mCD98 and hCD98, EcoRI hCD98U (5'-CCG GAA TTC cCa cCa TGA GCC AGG ACA CCG AGG TGG ATA TGA-3' (SEQ ID NO: 50)), NotI hCD98 (5'-AAG GAA AAA AGC GGC CGC TCA TCA GGC CGC GTA GGG GAA GCG GAG CAG CAG-3' (SEQ ID NO: 51)), EcoRI mCD98 (5'-CCG GAA TTC CCA CCA TGA GCC AGG ACA CCG AAG TGG ACA TGA AA-3' (SEQ ID NO: 52)), NotI mCD98L (5'-AAG GAA AAA AGC GGC CGC TCA TCA GGC CAC AAA GGG GAA CTG TAA CAG CA-3' (SEQ ID NO: 53)), cCD98 D2-F (5'-TCA TTC TGG ACC TTA CTC CCA ACT ACC-3' (SEQ ID NO: 54)), cCD98 D2-R (5'-GGT AGT TGG GAG TAA GGT CCA GAA TGA-3' (SEQ ID NO: 55)), cCD98 D3-F (5'-TGC TCT TCA CCC TGC CAG GGA CCC CTG TTT T-3' (SEQ ID NO: 56)), and cCD98 D3-R (5'-AAA ACA GGG GTC CCT GGC AGG GTG AAG AGC A-3' (SEQ ID NO: 57)) were synthesized. In PCR, mCD98 (GenBank/EMBL/DDBJ accession no. U25708), a plasmid vector pcDNA3.1-mCD98 retaining cDNA encoding human CD98, and pEF6/hCD98 prepared in Example 1 were used as templates.

KOD-Plus of Toyobo was used for amplification of cDNA. A reaction solution having a composition of 15 μL of cDNA, 5 μL of 10×KOD-Plus Buffer, 5 μL of dNTP mix, 1 μL of KOD-Plus, 3 μL of 25 mM MgSO4, a F primer, and a R primer was prepared in a final volume of 50 μL using double distilled water and subjected to PCR.

cDNA 1, F primer 1, and R primer 1, or cDNA 2, F primer 2, and R primer 2 were used, and a cycle of 94° C. for 15 seconds, 60° C. for 30 seconds, and 68° C. for 90 seconds (a cycle of 94° C. for 15 seconds, 55° C. for 30 seconds, and 68° C. for 50 seconds) was repeated 25 times. This reaction solution was subjected to 0.8% agarose gel electrophoresis, and the PCR amplification product was purified by a QIAquick gel extraction kit. The PCR amplification products were named P1 and P2, respectively. Each 5 μL of 2 to 3-time diluted P1 and P2 was then placed, and a cycle of 94° C. for 15 seconds, 55° C. for 30 seconds, and 68° C. for 2 minutes was repeated 3 times in the absence of a primer. After this reaction solution was heated to 99° C. for 5 minutes, the solution was diluted 5 to 10 times. 5 μL of this solution was used as a template together with F primer 1 and R primer 2, and a cycle of 94° C. for 15 seconds, 60° C. (55° C.) for 30 seconds, and 68° C. for 2 minutes was repeated 25 times. This reaction solution was subjected to 0.8% agarose gel electrophoresis, and the PCR amplification product was purified by the QIAquick gel extraction kit.

Figure 4A:
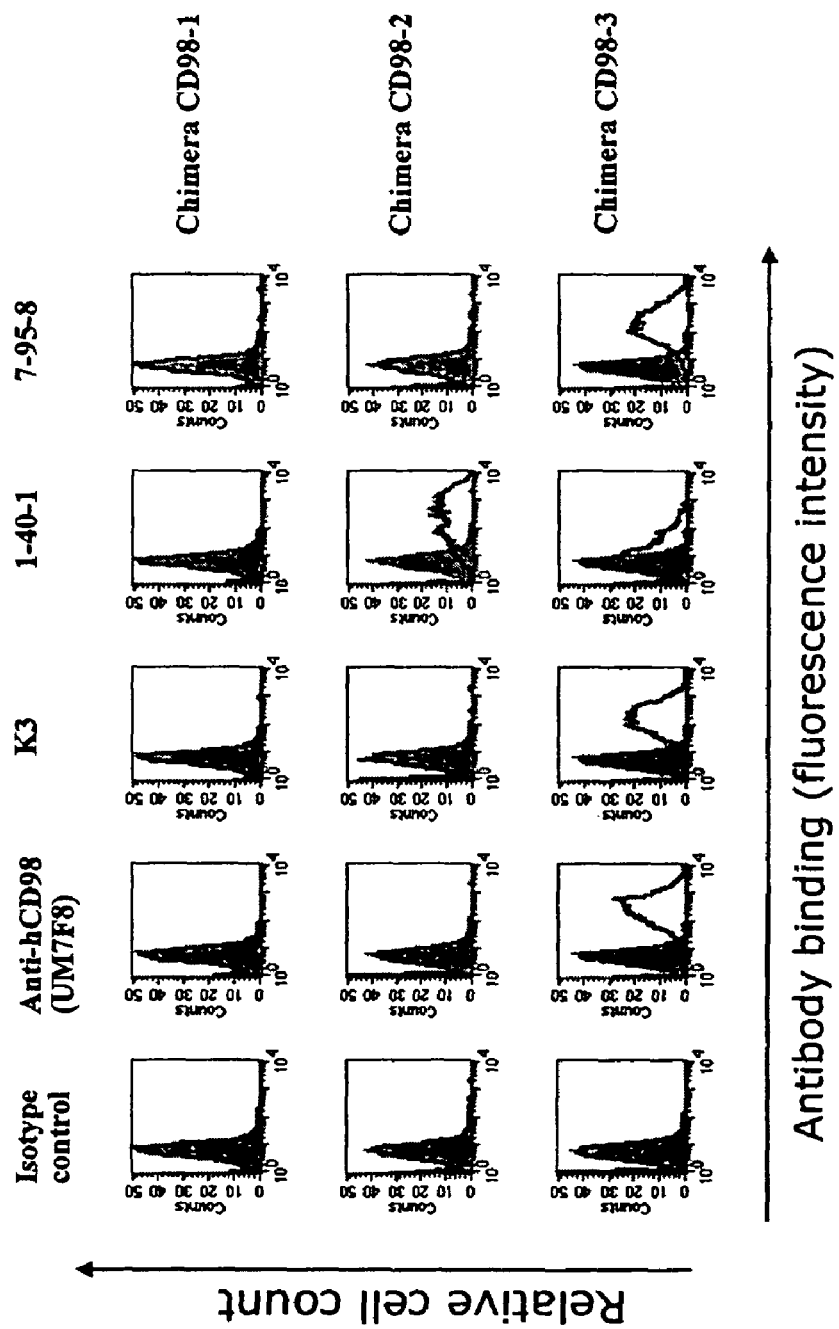
FIG. 4A shows the binding of human anti-CD98 monoclonal antibodies to various mouse/human chimera CD98-expressing L929 cell lines.
Figure 4B:
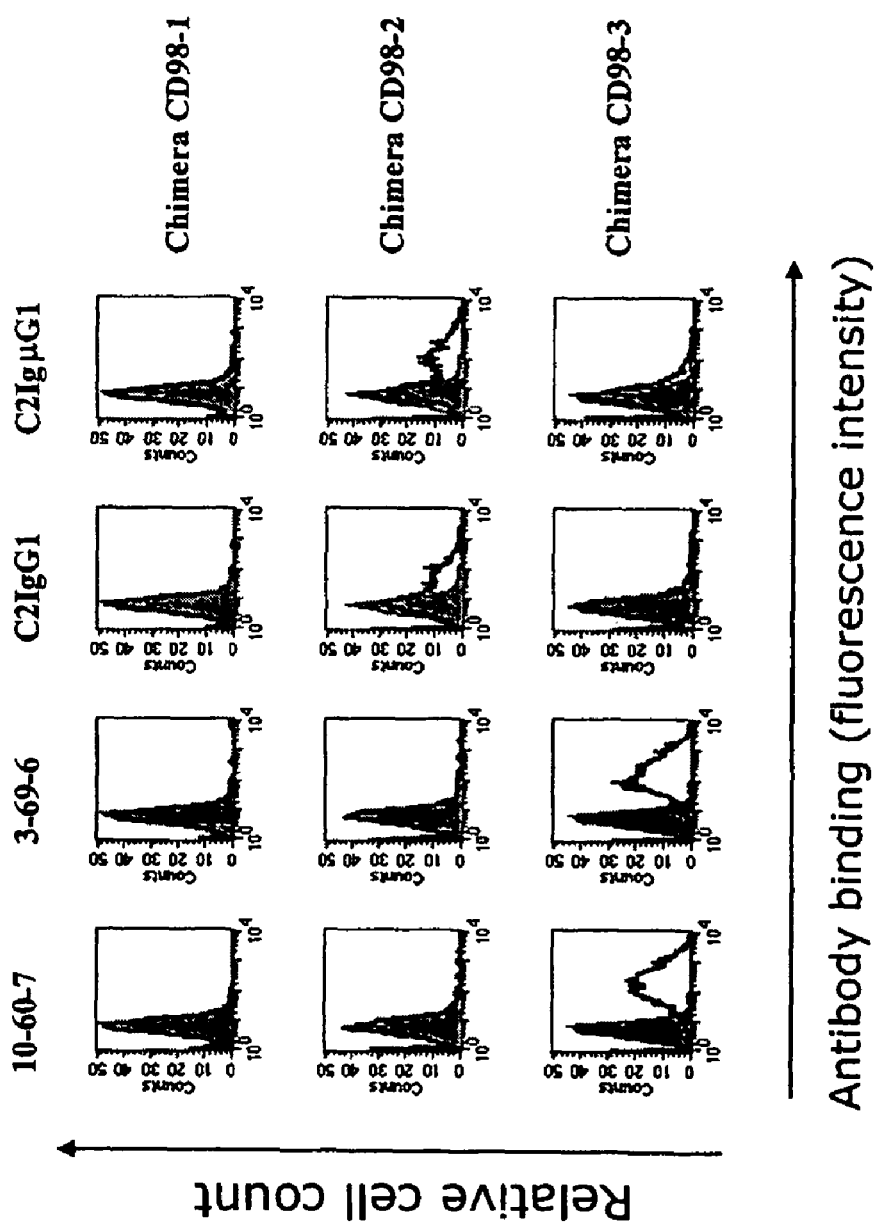
FIG. 4B shows the binding of human anti-CD98 monoclonal antibodies to various mouse/human chimera CD98-expressing L929 cell lines.

Chimera CD98-1, chimera CD98-2, and chimera CD98-3 were prepared using the following combinations (cDNA 1: F primer 1: R primer 1; and cDNA and F primer 2: R primer 2): (pEF6/hCD98: EcoRIhCD98U: cCD98D2-R; and pcDNA3.1-mCD98: cCD98D2-F: NotImCD98L); (pEF6/hCD98: EcoRIhCD98U: cCD98D3-R; and pcDNA3.1-mCD98: cCD98D3-F: NotImCD98L); and (pcDNA3.1-mCD98: EcoRImCD98U: cCD98D2-R; and pEF6/hCD98: cCD98D2-F: NotIhCD98L). The respective PCR-amplified cDNA fragments were digested with EcoRI and NotI and ligated to a pEF6myc-His/Bsd vector (manufactured by Invitrogen) that had been cleaved by the same enzymes. The DNA nucleotide sequence of the inserted portion was determined and it was confirmed that the sequence that had been amplified by PCR and inserted was identical to the gene sequence used as a template. The respective vectors were expressed in L929 cells together with the pEF1/hLAT1-EGFP vector prepared in Example 1 by the same method as in Example 2, and the binding of the respective FITC-labeled antibodies was examined by the FACS analysis by the same method as in Example 10. As a result (FIG. 4), the K3, 7-95-8, 10-60-7, and 3-69-6 antibodies bound only to L929 cells expressing the chimera CD98-3, similarly to the commercially available FITC-labeled anti-human CD98 antibody (clone UM7F8, manufactured by Becton Dickinson Ca. No. 556076), and it was suggested that the region from the amino acid residue 372 to the amino acid residue 530 of hCD98 is important for binding of these antibodies. On the other hand, the C2 antibody and the 1-40-1 neutralized antibody bound strongly only to the chimera CD98-2, showing that the region from the amino acid residue 104 to the amino acid residue 371 of hCD98 is important for the binding of these antibodies.

Example 12

Amino Acid Uptake Suppression Activity of Each of the Monoclonal Antibodies

Figure 5:
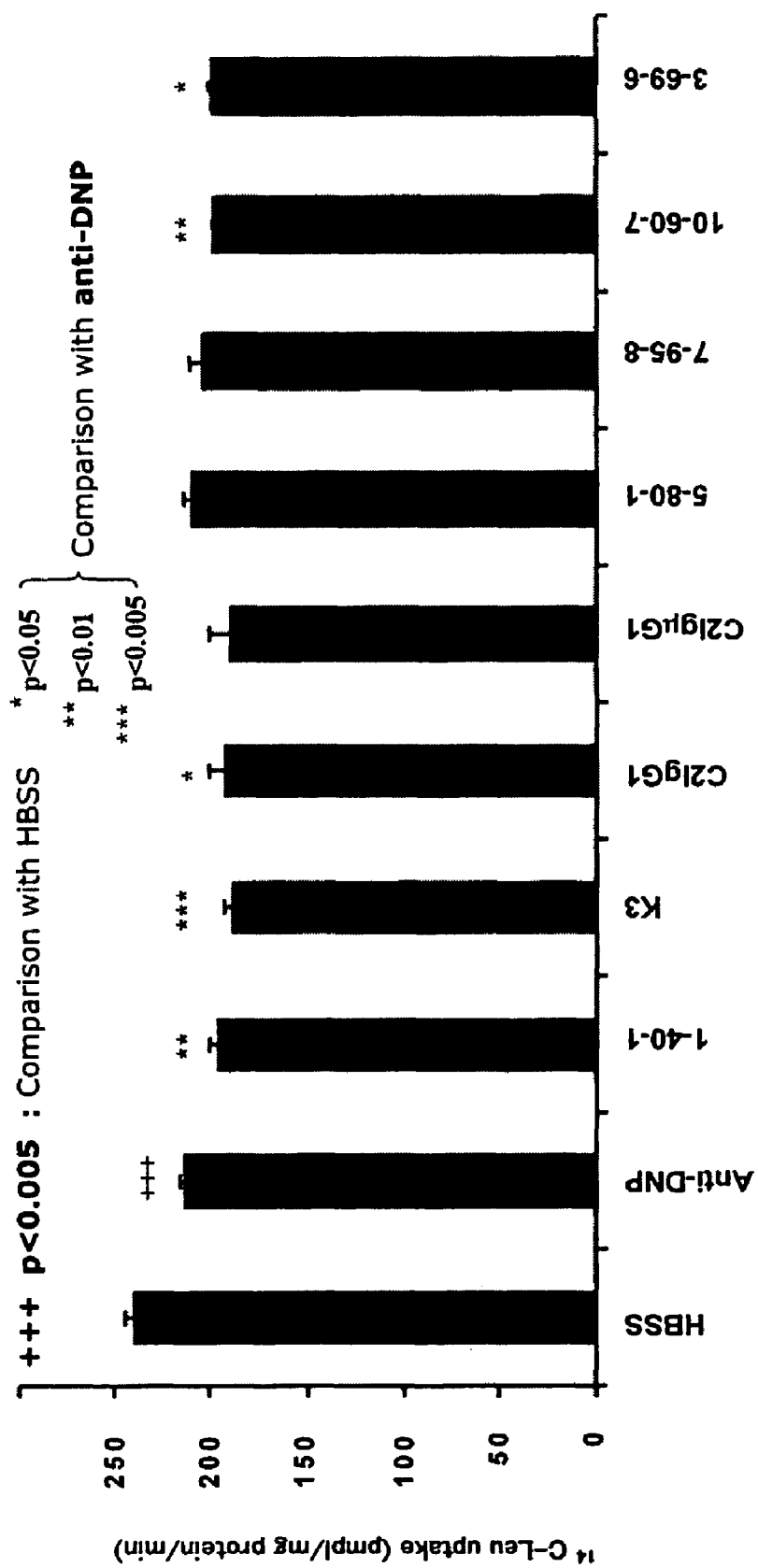
FIG. 5 shows activities of human anti-CD98 monoclonal antibodies to suppress the amino acid uptake by a T24 human bladder cancer cell line.

In order to determine whether or not the monoclonal antibodies influenced amino acid uptake of human bladder cancer cell line T24 cells, a substrate uptake experiment was conducted using leucine as a substrate in accordance with the method of Kanai et al. (Kim et al., Biochim. Biophys. Acta 1565: 112-122, 2002) as described below. $1\times10^5$ cells of the T24 cell line were inoculated to a 24-well culture plate and cultured in an MEM medium (manufactured by SIGMA ALDRICH) containing 10% FCS at 37° C. in 5% $CO_2$ for 2 days. After the culturing, the medium was removed, 0.25 mL/well of HBSS(−)(Na+-free) containing 200 μg/mL of the antibody was added and the cells were cultured at 37° C. in 5% $CO_2$ for 10 minutes. The recombinant antibodies were used for the C2, K3, 7-95-8, 10-60-7, 3-69-6, 1-40-1, and anti-DNP human antibodies and the antibody derived from a hybridoma was used for the 5-80-1. After that, the supernatant was removed, 0.5 mL/well of HBSS(−)(Na+-free) containing 1 μM $^{14}C$-Leu (manufactured by MORAVEK BIOCHEMICALS) was added and the cells were cultured for 1 minute. After washing with an ice-cooled HBSS(−)(Na+-free) solution 3 times, 0.1 N sodium hydroxide was added at 0.5 mL/well and the cells were collected. The amount of $^{14}C$-Leu in the collected solution was measured with a liquid scintillation counter model LSC-5100 (manufactured by ALOKA). The $^{14}C$-Leu uptake of the respective cells was obtained by measuring the protein concentration of the collected solution by the BCA method and standardizing the obtained value by the protein amount. The results (FIG. 5) show that the 1-40-1, K3, C2IgG1, 10-60-7, and 3-69-6 significantly suppressed leucine uptake as compared with the control antibody (DNP human antibody). The following experiments were conducted using the 1-40-1, K3, C2IgG1, 10-60-7, and 3-69-6 that significantly suppressed leucine uptake.

Example 13

Fluorescence Labeling of Each of the Monoclonal anti-hCD98/hLAT1 Antibodies

Each of the antibodies was fluorescently labeled by the method described below. A fluorescent substance, fluorescein isothiocyanate (FITC, manufactured by Sigma), was bound to the respective recombinant antibodies prepared in Example 4 to Example 8 in accordance with the attached instruction manual. To 1 to 2 mg/mL of the antibody in 200 mM sodium carbonate buffer (pH 8.3 to 8.5), FITC dissolved in dimethyl formamide was added in an amount of 20 to 40 times that of the antibody molecule, and the mixture was reacted while stirring at room temperature for 2 to 3 hours. The mixture was applied to a gel filtration column (NAP5, manufactured by Amersham Pharmacia Biotech) equilibrated with PBS to remove FITC that did not bind to the antibody. Under this condition, about three FITCs bound to 1 molecule of the antibody. All the fluorescently-labeled antibodies bound to a human colorectal cancer DLD-1 cell line that had been confirmed to express hCD98.

Example 14

Reactivity of Each of the Monoclonal Antibodies to Human Peripheral Blood-Derived T Cells, B Cells, and Monocytes and Normal Human Aortic Endothelial Cells (HAEC)

CD98 was known to be expressed in monocytes, activated T cells, and cultured normal endothelial cells. Thus, reactivities of the respective antibodies to human peripheral blood-derived T cells, B cells, and monocytes and human aortic endothelial cells (HAEC) were determined. The human peripheral blood-derived cells were prepared by the following method. 10 mL of human peripheral blood containing 1 mL of heparin (manufactured by Novo) was diluted 2 times with PBS, overlaid on 20 mL of a Ficoll-Paque PLUS solution (manufactured by Amersham Pharmacia Biotech), and centrifuged at 1500 rpm for 30 minutes, and then the cells were collected. After washing with PBS 2 times, mononuclear cells were prepared. Part of the mononuclear cells was cultured in an RPMI medium (manufactured by Gibco) containing 10 μg/mL of phytohaemagglutinin (manufactured by Sigma, PHA), 10% FCS, 0.1 mM non-essential amino acid solution (manufactured by Gibco), $5.5\times10^{-6}$ M 2-mercaptoethanol (manufactured by Gibco), and Penicillin/Streptomycin/Glutamine (manufactured by Gibco) at 37° C. in 5% $CO_2$ for 72 hours. Expression of CD25 that was an activation marker was observed for human peripheral blood-derived T cells and B cells by PHA stimulation (FACS analysis using an FITC-labeled anti-human CD25 antibody (manufactured by Becton Dickinson Ca. 555431)). The respective prepared cells were suspended in the a Staining Buffer (SB) at $2\times10^6$/mL, and the cell suspension was dispensed in a 96-well round-bottomed plate (manufactured by Becton Dickinson) at 50 µL/well. The respective FITC-labeled antibodies prepared in Example 13 at 5 µg/mL was reacted with an anti-human CD3 antibody (manufactured by Becton Dickinson Ca. No. 555340), an anti-human CD14 antibody (manufactured by Becton Dickinson Ca. No. 347497), or an anti-human CD19 antibody (manufactured by Immunotech Ca. No. IM1285) at ice temperature for 30 minutes. The commercially available FITC-labeled anti-human CD98 antibody (clone UM7F8) was used as a positive control, and the FITC-labeled anti-DNP human IgG1 antibody was used as a negative control. After washing with SB once, the resultant was suspended in 300 µL of FACS buffer and the reactivities of the respective antibodies were determined by FACS.

Figure 6A:
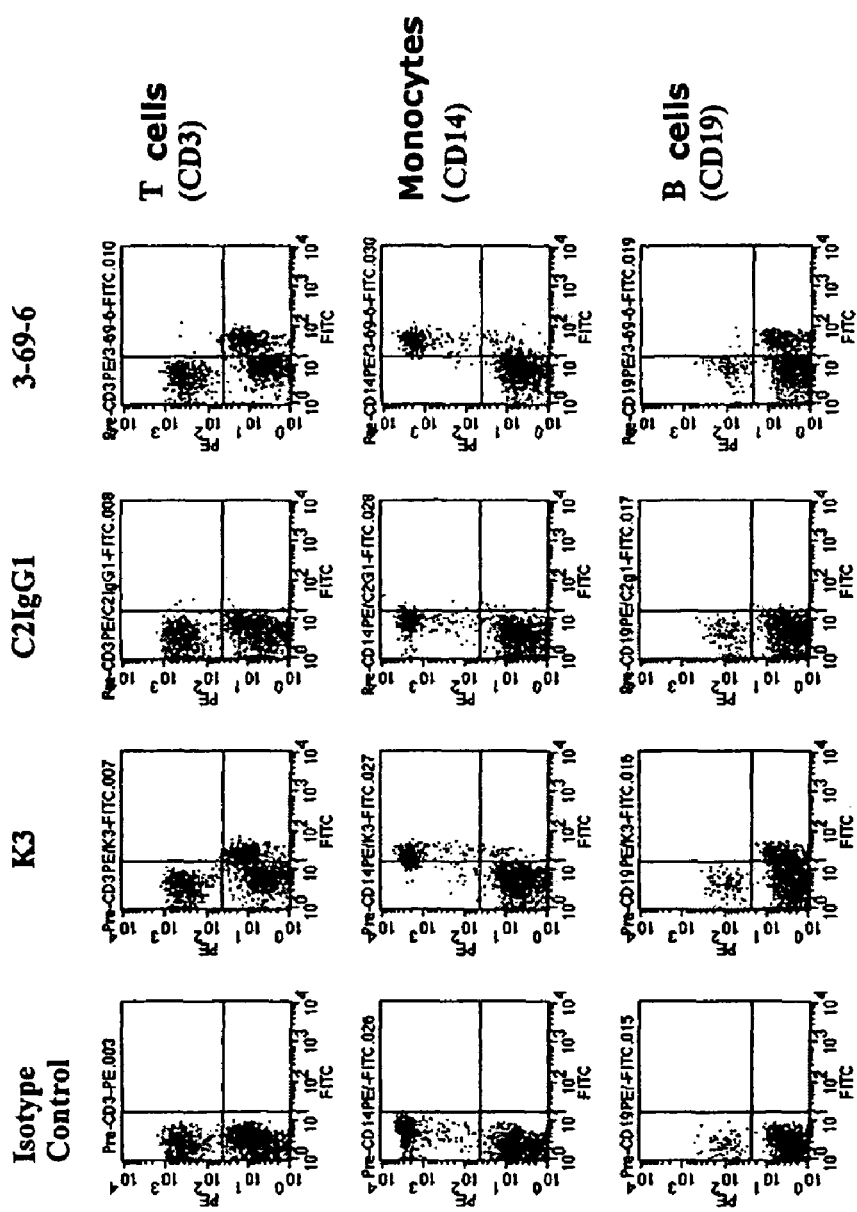
FIG. 6A shows the binding of human anti-CD98 monoclonal antibodies to human peripheral blood T cells, B cells, and monocytes.
Figure 6B:
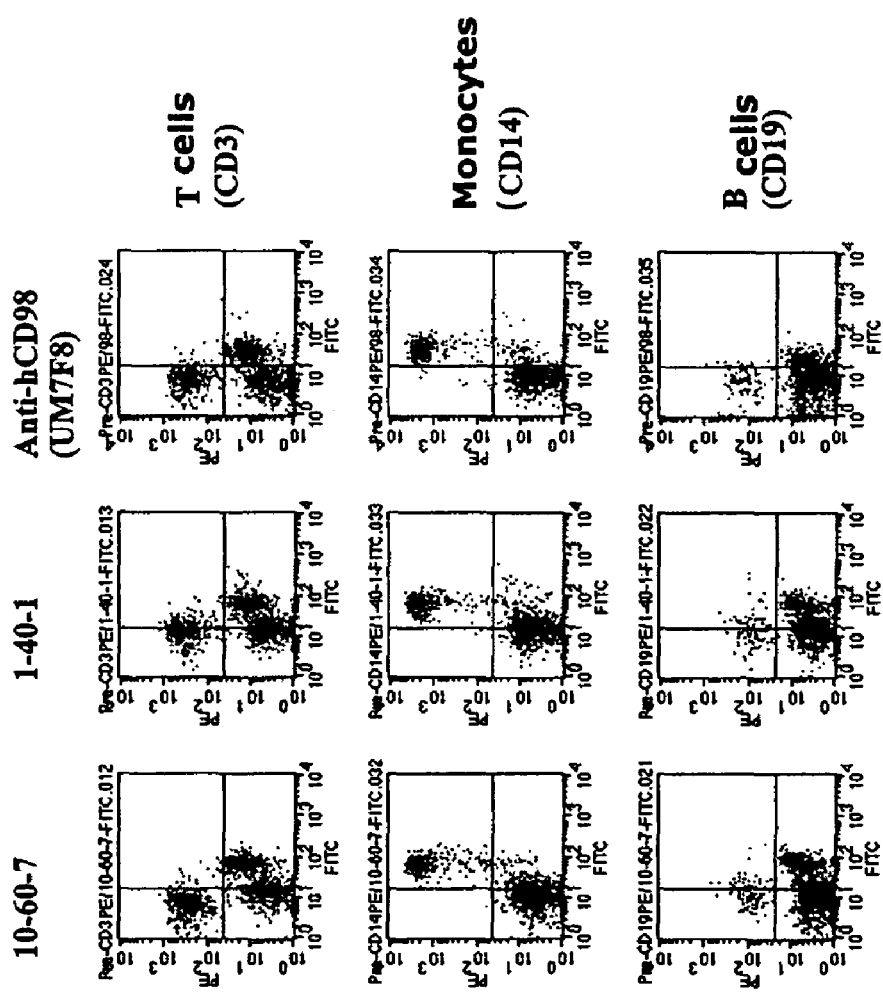
FIG. 6B shows the binding of human anti-CD98 monoclonal antibodies to human peripheral blood T cells, B cells, and monocytes.
Figure 7:
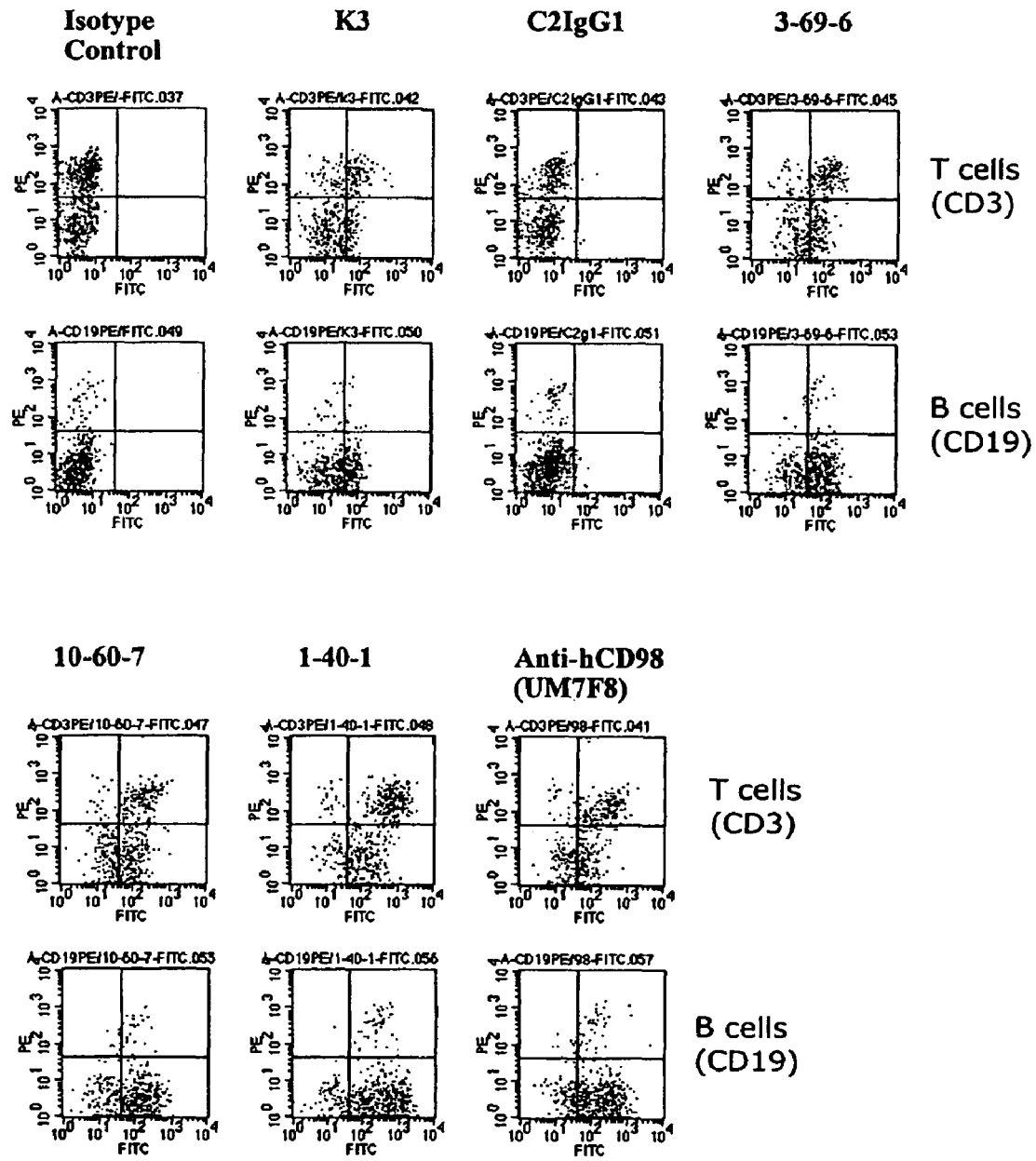
FIG. 7 shows the binding of human anti-CD98 monoclonal antibodies to PHA-activated human peripheral blood T cells and B cells.

As a result, the antibodies other than C2IgG1 exhibited a binding mode similar to UM7F8, thus bound significantly to the monocytes, activated T cells, and activated B cells (FIG. 6 and FIG. 7). On the other hand, C2IgG1 was not observed to bind significantly to any of the cells (FIG. 6 and FIG. 7).

HAEC cells (manufactured by Cambrex) were cultured in accordance with the attached instruction manual and then the cells subcultured not more than 4 times were used. The reactivities of C2IgG1, K3, 7-95-8, 10-60-7, 3-69-6, and 1-40-1 antibodies to the cultured HAEC were examined by the same method as described above. When the respective antibodies were reacted at the concentrations of 3.2 ng/mL to 50 µg/mL, the K3, 7-95-8, 10-60-7, 3-69-6, and 1-40-1 bound to HAEC, but C2IgG1 did not bind to HAEC (FIG. 8).

Figure 8:
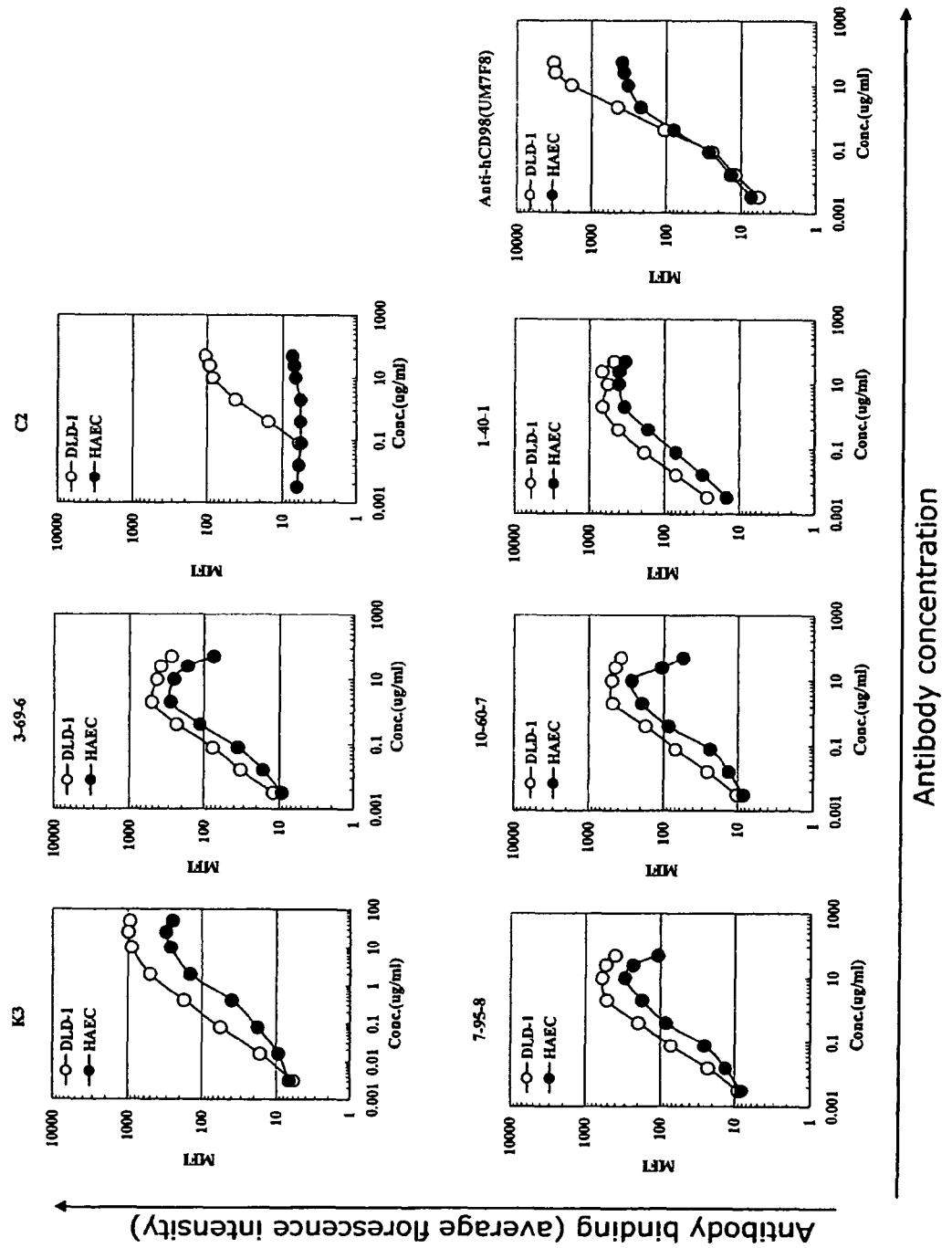
FIG. 8 shows the binding of human anti-CD98 monoclonal antibodies to human aortic endothelial cells (HAEC) and a human colorectal cancer cell line (DLD-1).

It was shown, on the other hand, that all the antibodies had higher specificity to DLD-1 cancer cells than UM7F8 under certain condition (an antibody concentration of 3 µg/mL or lower in the present Example) when the antibodies were reacted with the human colorectal cancer cell line DLD-1 under the same condition (FIG. 8). It was strongly suggested that C2IgG1, in particular, was an antibody having high cancer specificity. The experiment described below was conducted using the C2IgG1, K3, and 3-69-6.

Example 15

Reactivity of Each of the Monoclonal Antibodies to Cancer Cell Lines

The reactivities of the respective antibodies of C2IgG1, K3, and 3-69-6 to the colorectal cancer cell line (DLD-1), a lung cancer cell line (H226), a prostate cancer cell line (DU145), melanoma cell lines (G361, SKMEL28, and CRL1579), a non-Hodgkin lymphoma cell line (Ramos), a bladder cancer cell line (T24), breast cancer cell lines (MCF and MDA-MB-231), a pancreatic cancer cell line (HS766T), a multiple myeloma cell line (IM9), and an erythroblastic leukemia cell lines (see FIG. 3 for K562) were examined by the FACS analysis by the same method as in Example 9. The cell suspension at $2\times10^6$/mL was prepared with a Staining Buffer (SB) for the cell lines and dispensed in a 96-well round-bottomed plate (manufactured by Becton Dickinson) at 50 µL/well. The antibody or the FITC-labeled antibody prepared to 5 µg/mL was added at 50 µL/well and allowed to react at ice temperature for 30 minutes. The anti-DNP human IgG1 antibody or the FITC-labeled anti-DNP human IgG1 antibody was used as a negative control. After washing with SB once, 50 µL of the RPE fluorescently-labeled goat anti-human Igγ F(ab')₂ antibody (manufactured by SuthernBiotech) diluted 200 times with SB was added and the mixture was incubated at ice temperature for 30 minutes. In the case of the FITC-labeled antibody, this operation was omitted. After washing with SB once, the resultant was suspended in 300 µL of FACS buffer and the average fluorescence intensity of the respective cells was measured by FACS.

Figure 9A:
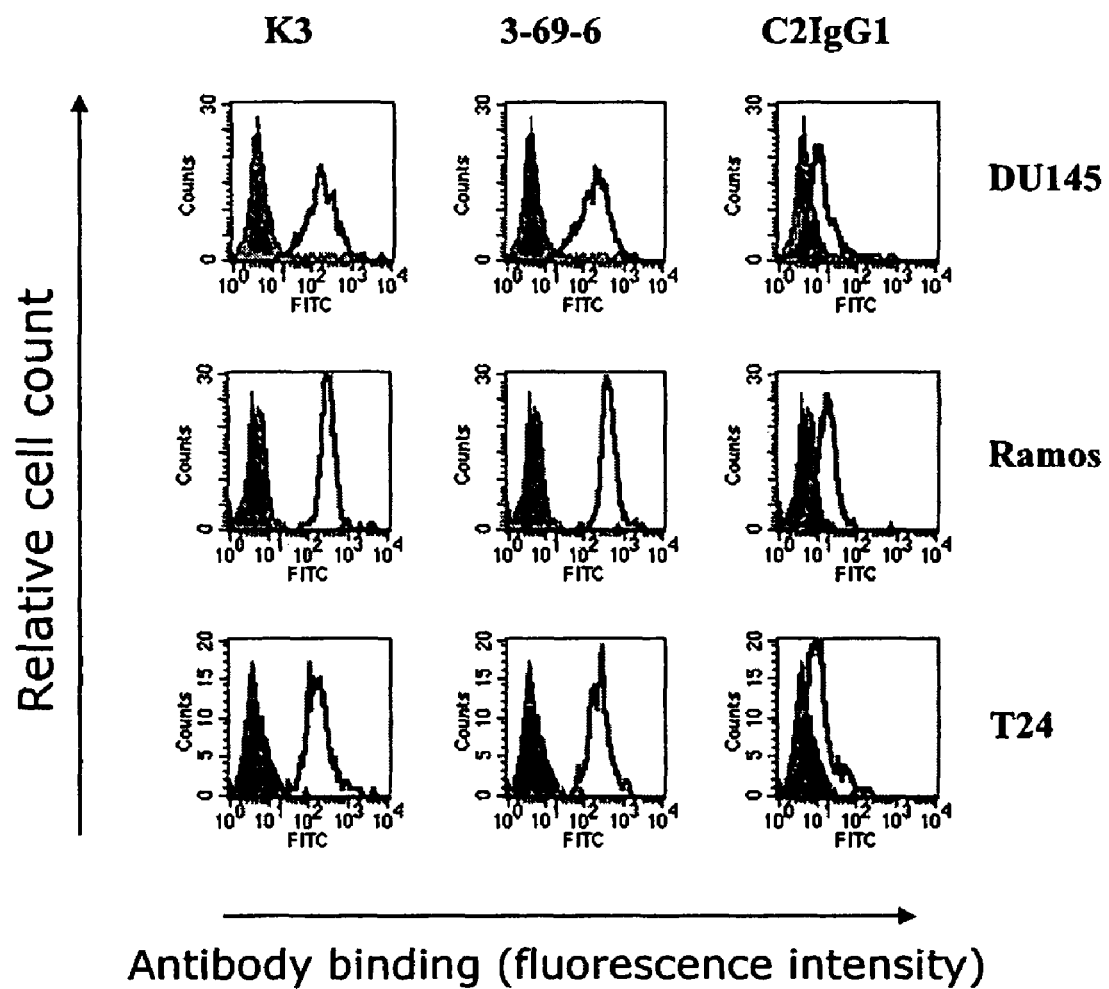
FIG. 9A shows the binding of human anti-CD98 monoclonal antibodies to various cancer cell lines.
Figure 9B:
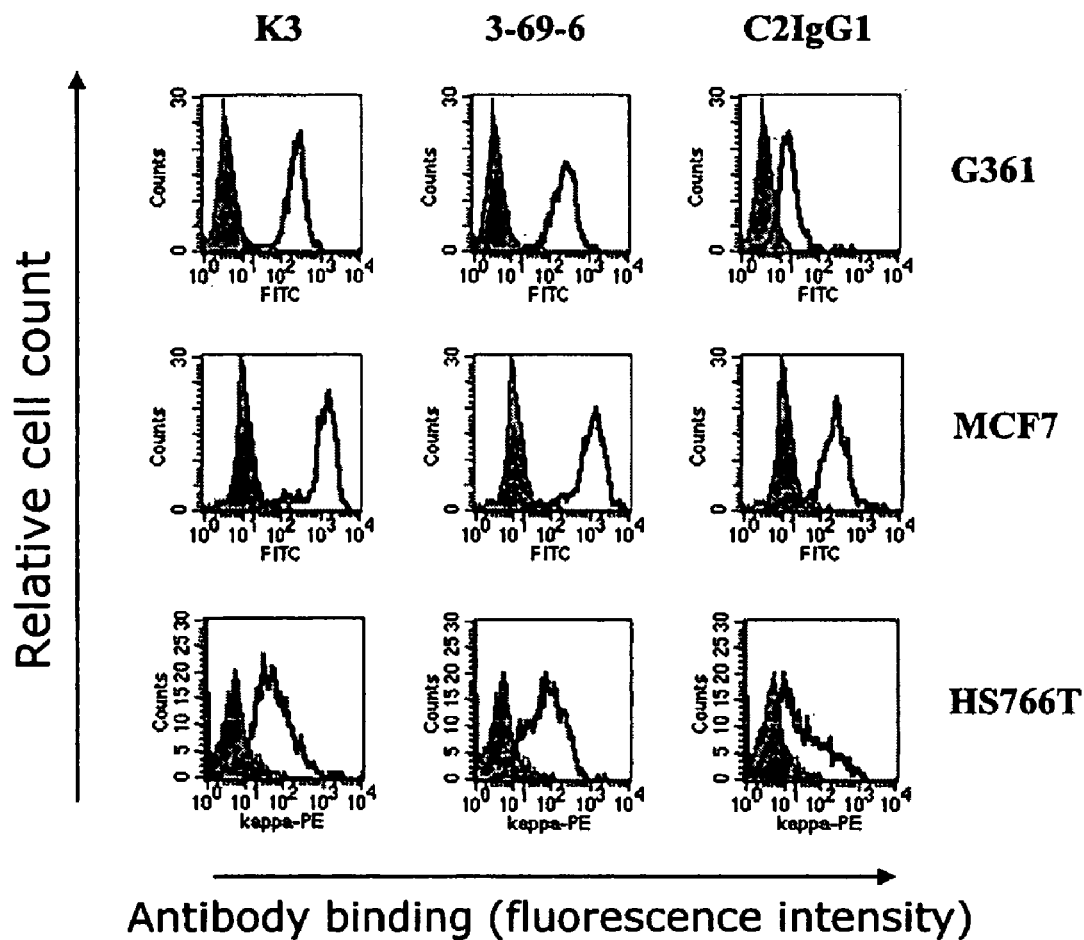
FIG. 9B shows the binding of human anti-CD98 monoclonal antibodies to various cancer cell lines.
Figure 10A:
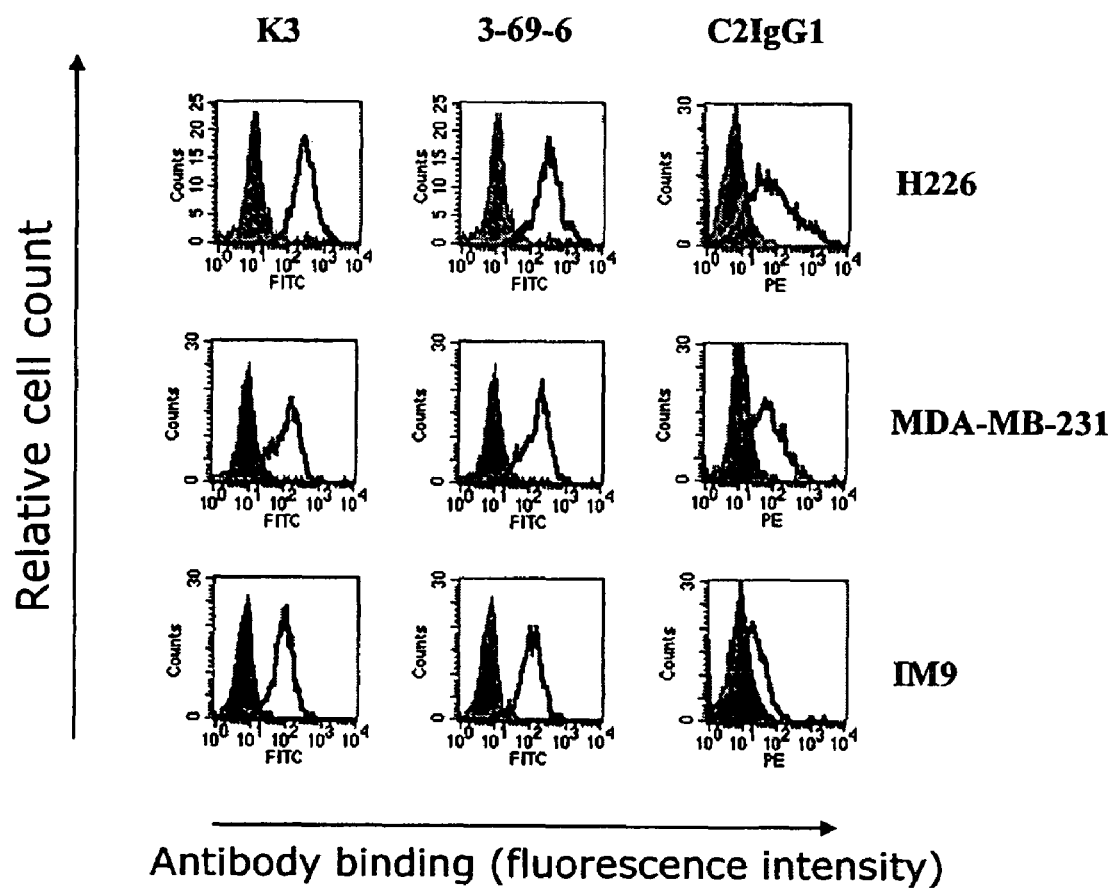
FIG. 10A shows the binding of human anti-CD98 monoclonal antibodies to various cancer cell lines.
Figure 10B:
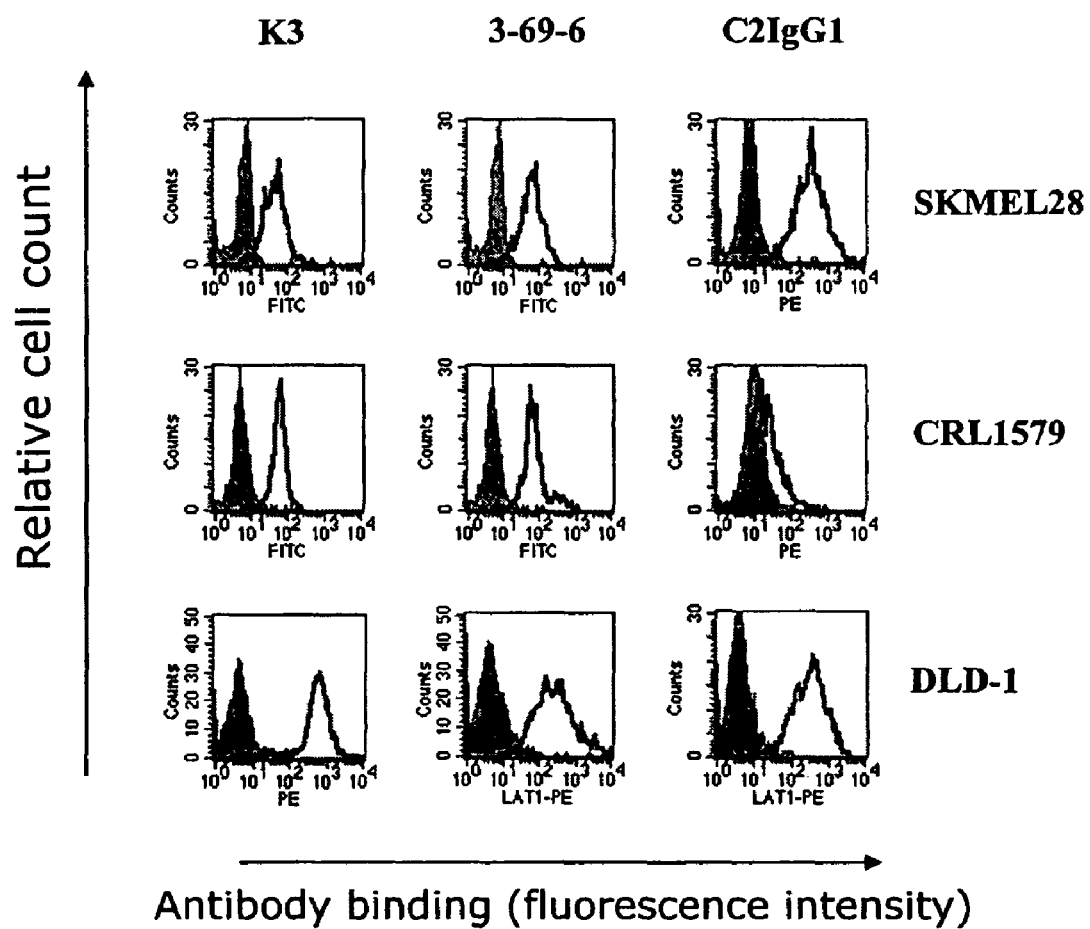
FIG. 10B shows the binding of human anti-CD98 monoclonal antibodies to various cancer cell lines.

As a result, all the antibodies were found to have binding activity to the respective cancer cell lines (FIG. 9 and FIG. 10). In addition, all the antibodies bound strongly to the human colorectal cancer cell line of Colo205, SW480, SW620, LOVO, LS180, and HT29.

Example 16

Anti-Tumor Effect of K3, C2IgG1, and 3-69-6 in Cancer Mouse Model

The anti-tumor effect of the recombinant monoclonal antibodies of K3, C2IgG1, and 3-69-6 prepared in Example 4 to Example 8 were examined using a cancer mouse model in accordance with the method described below.

5-week old Balb/c nude mice (purchased from Clea Japan) were allocated into groups consisting of 5 mice based on the individual body weight. A mixture of $5\times10^6$ colorectal cancer Colo205 cells and 5 µg of the antibody in 100 µL of PBS was subcutaneously transplanted in the abdomen. On days 2, 4, and 6 after transplantation, the antibody dissolved in a solvent (PBS containing 1% mouse serum) at 100 µg/100 µL was administered intraperitoneally to the mice and a tumor size was measured. The solvent was used as a negative control for the antibody.

Figure 11:
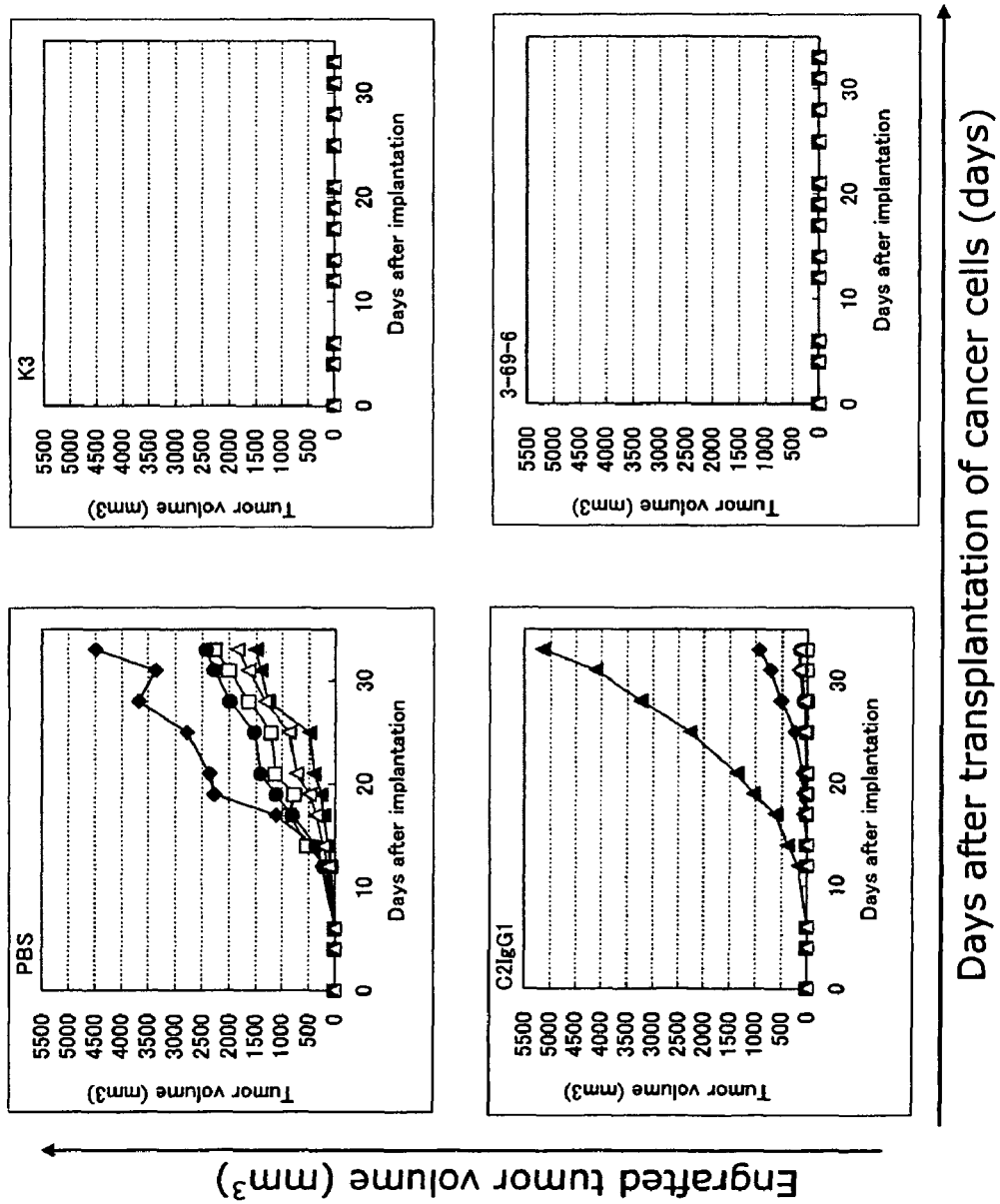
FIG. 11 shows the tumor volume in each of nude mice observed when human anti-CD98 monoclonal antibody K3, 3-69-6, or C2IgG1 was administered to the mice to which tumor cells had been transplanted.

The results of the experiment above are shown in FIG. 11. The respective broken lines in the FIG. show data for the individual mice. In the control group, engraftment of cells of the cancer cell line was observed in all the individuals on day 5 and the average tumor volume (calculated by long diameter x short diameter x short diameter×0.5)±SE was 165.55±31.71 mm³ on day 12. In the C2IgG1 group, on the other hand, only one individual exhibited tumor growth as in the control group (a tumor mass of 169.44 mm³ on day 12), but a stronger anti-tumor activity of administration of the C2IgG1 antibody was observed in other individuals. The averages volume±SE of the tumor masses on day 28 were 1977.64±442.04 for the control group and 775.31±622.47 for the C2IgG1 antibody administration group, thus the C2IgG1 antibody suppressed significantly the growth of the Colo205 cancer cell-derived tumor (p<0.01). No engraftment of cancer was observed in any individuals of the K3 group or the 3-69-6 group even after 30 days or more had passed. The average body weight decreased only in the control group (a decrease by about 20% as compared with the K3 group on day 30 after transplantation).

Based on these results, the K3, C2IgG1, and 3-69-6 were found to be antibodies with cancer cell growth suppressing activity.

Example 17

Anti-Tumor Effect of C2IgG1 Monoclonal Antibody in Cancer-Bearing Isogenic Mouse Model The anti-tumor effect of the recombinant monoclonal antibody C2IgG1 prepared in Example 4 to Example 8 was examined in a cancer-bearing isogenic mouse model in accordance with the method described below.

Figure 12:
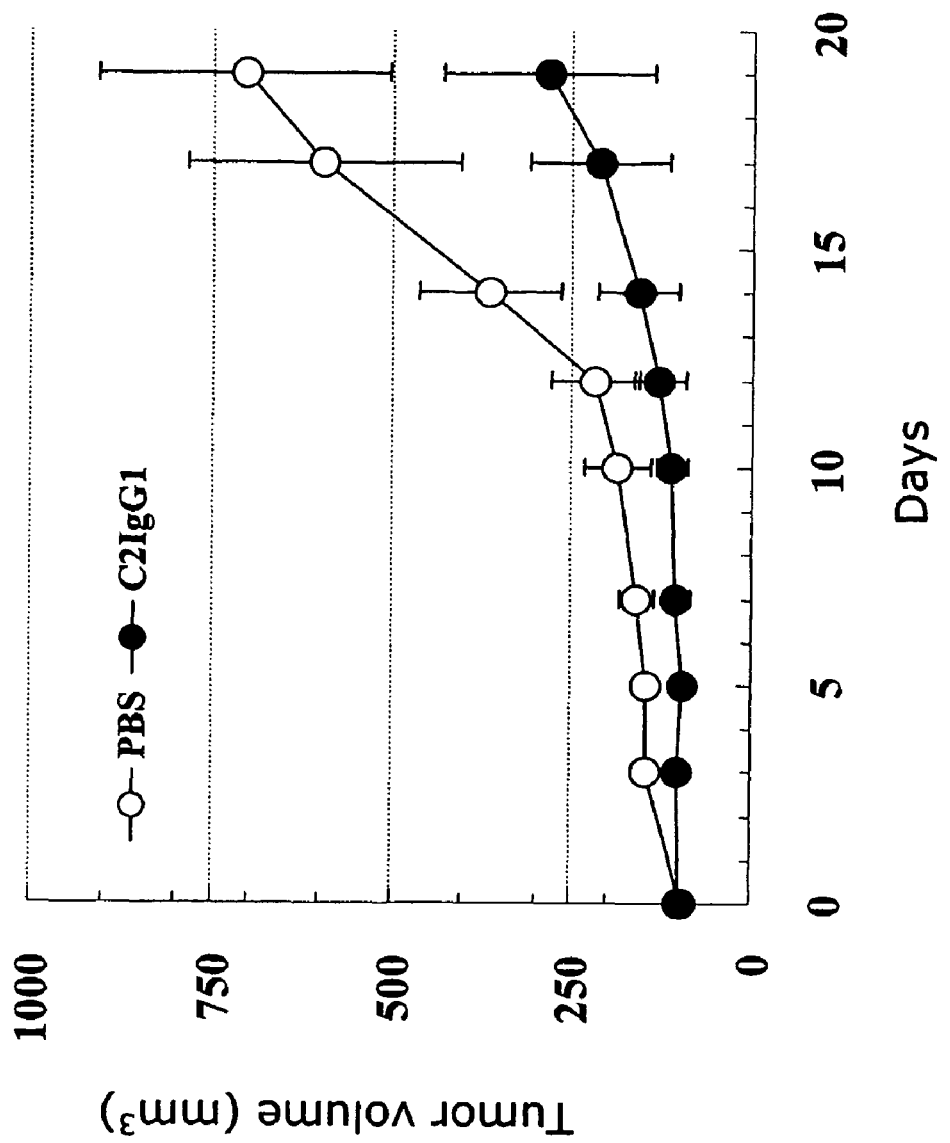
FIG. 12 shows the result of measurement of tumor volume after administration of a human anti-CD98 monoclonal antibody C2IgG1 at 100 μg/mouse 3 times every other day to cancer-bearing mice having a tumor grown to 90 mm$^3$.

Balb/c female mice to which the hCD98/hLAT1-E-expressing CT26 cells prepared in Example 2 were transplanted at $5\times10^6$ cells were divided into 2 groups by 5 mice each based on tumor volume. 100 μg/100 μL of the C2IgG1 in a solvent (PBS containing 1% mouse serum) was administered intraperitoneally to the mice at the point (on day 0) when a tumor volume increased to about 90 mm3 (calculated by long diameter x short diameter x short diameter×0.5), on days 3 and 5. As a control, the solvent was administered. As a result, C2IgG1 was observed to have an activity of significantly strongly suppressing the growth of an engrafted tumor (FIG. 12).

Example 18

Cross Reactivities of C2IgG1 and K3 Antibodies to Monkey Cells

Figure 13:
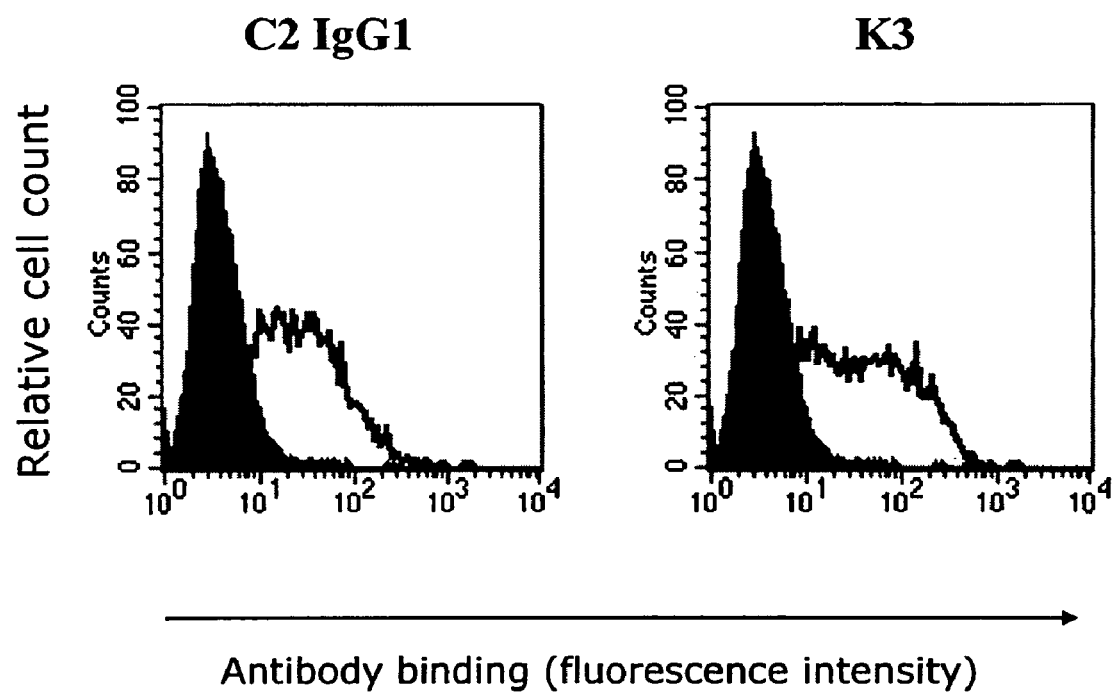
FIG. 13 shows the cross-reaction of human anti-CD98 monoclonal antibodies K3 and C2IgG1 with a monkey cell line COS-7.

Cross-reactivities of the C2IgG1 and K3 to monkey cells (COS-7 cells) were examined by the FACS analysis. $2 \times 10^6$/mL cells were suspended in a Staining Buffer (SB). The cell suspension was dispensed in a 96-well round-bottomed plate (manufactured by Becton Dickinson) at 50 μL/well. Subsequently, 50 μL of the antibody prepared in 5 μg/mL with SB was added, and the resultant was allowed to react at ice temperature for 30 minutes. The DNP human IgG1 antibody was used as a negative control. After washing with SB once, 50 μL/well of the RPE fluorescently-labeled goat anti-human Igy F(ab')$_2$ antibody (manufactured by SuthernBiotech) diluted 200 times with SB was added and allowed to react at ice temperature for 30 minutes. After washing with SB once, the resultant was suspended in 300 μL of FACS buffer and fluorescence intensity showing antibody binding was measured by FACS. As a result, both antibodies bound to the COS-7 cell line, and the C2IgG1 and the K3 were found to be antibodies having cross-reactivity to monkey cells (FIG. 13).

Example 19

Effect of C2IgG1 in CANCER-Bearing Mouse Model

The anti-tumor activity of the C2IgG1 was examined using a cancer-bearing mouse model in accordance with the method described below.

Burkitt's lymphoma cell line Ramos (purchased from ATCC) was transplanted subcutaneously at $3 \times 10^6$/mouse individual to the back of 6-week old Balb/c-SCID mice (purchased from Clea Japan). On day 13 after transplantation, the size of engrafted tumor was measured, and cancer-bearing mice having a tumor of 30 to 140 mm$^3$ were separated into groups consisting 6 mice/group. The C2IgG1 was administered intraperitoneally at 100 mg/mouse individual (dissolved in 200 mL of PBS) 3 times/week. Rituximab (manufactured by Zenyaku Kogyo) was used as a positive control and PBS was used as a negative control. A tumor volume and body weight were measured 3 times a week. A longer diameter, a shorter diameter, and a height of a tumor mass were measured, and a value obtained in accordance with the formula of (longer diameter)×(shorter diameter)×(height)/2 was defined as a tumor volume.

Figure 14:
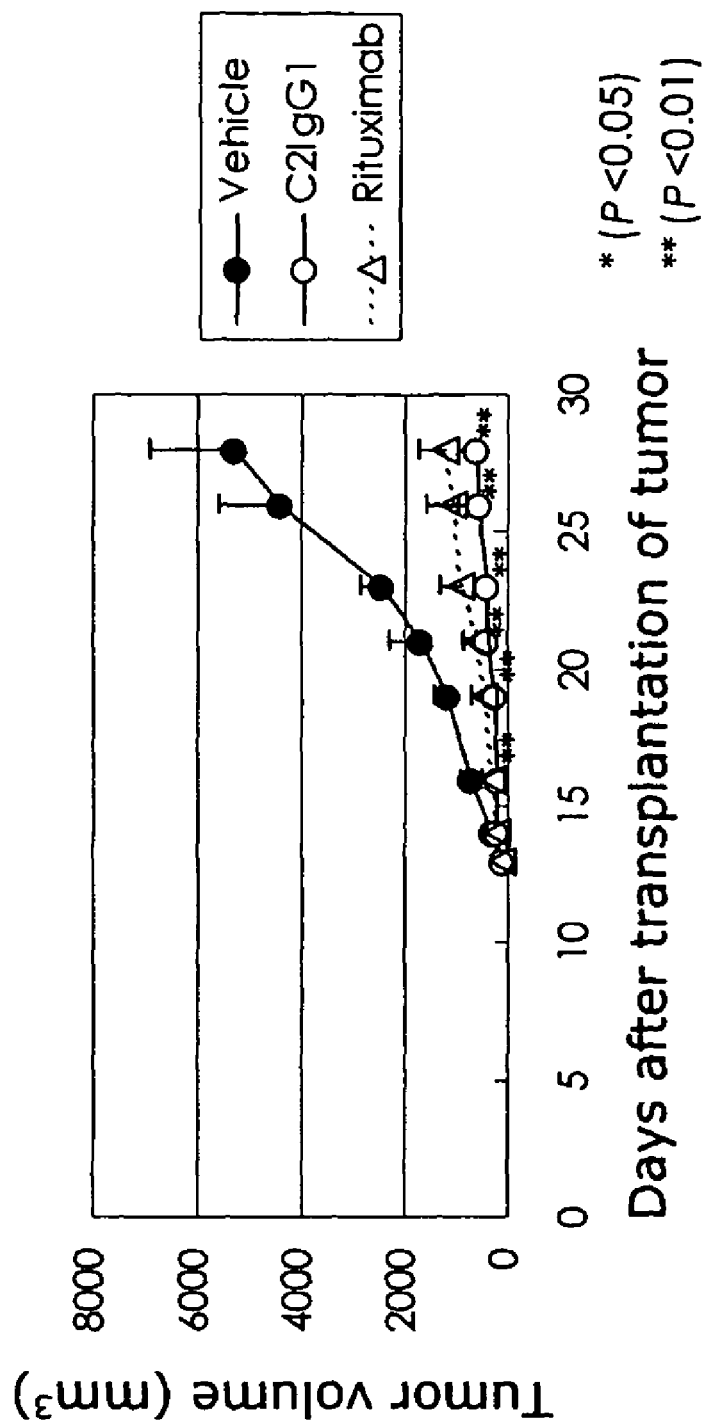
FIG. 14 shows the result of measurement of tumor size after administration of a human anti-CD98 monoclonal antibody C2IgG1 and Rituximab at 100 mg/mouse 3 times per week, respectively, to cancer-bearing mice having a tumor grown 30 to 140 mm$^3$ to which a Burkitt's lymphoma cell line Ramos had been transplanted.

The results are shown in FIG. 14. A significant tumor growth suppressing effect of the C2IgG1 administration was observed beginning day 16 after tumor transplantation.

Example 20

Amino Acid-Modified C2IgG1NS

Both of the C2IgG1 and C2IgG1NS have a high aggregate content when recombinant antibodies are prepared. Therefore, I (isoleucine) at position 117 from the fifth M (methionine) as the amino acid at position 1 that corresponds to a translation initiation codon ATG in the light chain variable region sequence of the C2IgG1NS represented by SEQ ID NO: 47 was replaced with other amino acids to prepare variants.

Preparation of C2IgG1NS/I117N Vector

In order to prepare C2IgG1NS/I117N in which isoleucine at position 117 of the light chain was replaced with asparagine, various mutant DNAs encoding amino acid substitution were prepared using the N5KG1-Val C2IgG1NS vector prepared in Example 6 as a template by the site-specific mutagenesis method with a GeneEditor™ in vitro Site-Directed Mutagenesis System (Promega No. Q9280).

C2NS Lc 117I/HYND-p: (5'-TCAGTATGGT AGCT-CACCTN ATTTCACTTT CGGCCCTGGG ACC-3' (N=A·T·G·C) (SEQ ID NO: 69)) was used as an oligonucleotide (5'-end phosphorylated) for mutagenesis. An intended oligonucleotide for mutagenesis and a Selection Oligonucleotide attached to the above kit were annealed to a template DNA to synthesize mutated chains, and then a mutant was selected using the fact that only the mutant grows in the presence of GeneEditor™ Antibiotic Selection Mix. More specifically, a dsDNA template was incubated under an alkaline condition (0.2 M NaOH, 0.2 mM EDTA (final concentration)) at room temperature for 5 minutes, then 1/10 volume of 2 M ammonium acetate (pH 4.6) was added for neutralization, and the template was recovered by ethanol precipitation. To the template DNA that had been subjected to alkaline degeneration, an oligonucleotide for mutagenesis, a new Selection Oligonucleotide (Bottom Select Oligo, 5'-end phosphorylated 5'-CCGCGAGACC CACCCTTGGA GGCTCCAGAT TTATC-3' (SEQ ID NO: 85)) for acquisition of antibiotic resistance, and an annealing buffer attached to the kit were added. The mixture was kept at 75° C. for 5 minutes and the temperature was slowly decreased to 37° C. for annealing. Then, for synthesis and ligation of a mutated chain, Synthesis 10× buffer attached to the kit, a T4 DNA Polymerase, and a T4 DNA ligase were added and the resultant was allowed to react at 37° C. for 90 minutes. A plasmid DNA was prepared from a transformed E. coli obtained by transforming a competent cells BMH 71-18 mutS in the presence of the GeneEditor™ Antibiotic Selection Mix and culturing, and then ElectroMAX DH10B Cells (Invitrogen No. 18290-015) were transformed with the DNA by the electroporation and inoculated to an LB plate containing the GeneEditor™ Antibiotic Selection Mix. The transformant generated on the plate was cultured, and the plasmid DNA was purified and the DNA nucleotide sequence was analyzed. Based on the result concerning the DNA nucleotide sequence, an expression vector of C2IgG1NS mutant to which mutation of an intended amino acid was introduced was obtained. The obtained plasmid DNA expressing the mutant protein with one amino acid substitution was named N5KG1-Val C2IgG1NS/I117N vector.

Preparation of C2IgG1NS/I117C Vector

In order to prepare C2IgG1NS/I117C in which isoleucine at position 117 of the light chain was replaced with cystein, various mutant DNAs encoding amino acid substitution were prepared by the site-specific mutagenesis method using GeneEditor™ in vitro Site-Directed Mutagenesis System (Promega No. Q9280) using the N5KG1-Val C2IgG1NS vector prepared in Example 6 as a template.

C2NS Lc 117I/GRC-p(5'-TCAGTATGGT AGCTCAC-CTB GTTTCACTTT CGGCCCTGGG ACC-3' (B=C·G·T) (SEQ ID NO: 70)) was used as an oligonucleotide for mutagenesis (5'-end phosphorylated). An intended oligonucleotide for mutagenesis and a Selection Oligonucleotide attached to the above kit were annealed with a template DNA to synthesize mutated chain, and then a mutant was selected by using the fact that only the mutant grows in the presence of GeneEditor™ Antibiotic Selection Mix. More specifically, a dsDNA template was incubated under an alkaline condition (0.2 M NaOH, 0.2 mM EDTA (final concentration)) at room temperature for 5 minutes, then 1/10 volume of 2 M ammonium acetate (pH 4.6) was added for neutralization, and the template was recovered by ethanol precipitation. To the template DNA that had been subjected to alkaline degeneration, an oligonucleotide for mutagenesis and a new Selection Oligonucleotide (Bottom Select Oligo, 5'-end phosphorylated 5'-CCGCGAGACC CACCCTTGGA GGCTCCAGAT TTATC-3' (SEQ ID NO: 85)) for acquisition of antibiotic resistance, and an annealing buffer attached to the kit were added, and then the mixture was kept at 75° C. for 5 minutes and the temperature was slowly decreased to 37° C. for annealing. Then, for synthesis and ligation of the mutated chain, Synthesis 10× buffer attached to the kit, a T4 DNA Polymerase, and a T4 DNA ligase were added and the resultant was allowed to react at 37° C. for 90 minutes. A plasmid DNA was prepared from a transformed *E. coli* obtained by transforming a competent cells BMH 71-18 mutS in the presence of the GeneEditor™ Antibiotic Selection Mix and culturing, and then ElectroMAX DH10B Cells (Invitrogen No. 18290-015) were transformed with the DNA by the electroporation and inoculated to an LB plate containing the GeneEditor™ Antibiotic Selection Mix. The transformant generated on the plate was cultured, and the plasmid DNA was purified and the DNA nucleotide sequence was analyzed. Based on the result concerning the DNA nucleotide sequence, an expression vector of C2IgG1NS mutant to which mutation of an intended amino acid was introduced was obtained. The obtained plasmid DNA expressing the mutant protein with one amino acid substitution was named N5KG1-Val C2IgG1NS/I117C vector.

Preparation of C2IgG1NS/117IL vector

C2IgG1NS/I117L in which isoleucine at 117 of the light chain was replaced with leucine was prepared using the N5KG1-Val C2IgG1NS vector prepared in Example 6 as a template by the method described below.

For DNA amplification, KOD-Plus of Toyobo was used. A reaction solution having a composition of 1 μL of cDNA, 5 μL of 10×KOD-Plus Buffer, 5 μL of dNTP mix, 1 μL of KOD-Plus, 2 μL of 25 mM MgSO$_4$, a F primer, and a R primer was prepared in a final volume of 50 μL using double distilled water and subjected to PCR.

C2NS Lc 117IL R (5'-GGTCCCAGGG CCGAAAGTGA ATAGAGGTGA GCTACCATAC TGCTG-3' (SEQ ID NO: 71)) was synthesized, the C2NS Lc 117IL R and the C2-1 Lc Bgl II F (5'-AGA GAG AGA GAT CTC TCA CCA TGG AAA CCC CAG CGCAGC TTC TCT TC-3' (SEQ ID NO: 18)) were used, the N5KG1-Val C2IgG1NS vector was used as a template, and a cycle of 94° C. for 15 seconds, 60° C. for 30 seconds, and 68° C. for 1 minute was repeated 25 times. This reaction solution was subjected to 0.8% agarose gel electrophoresis, and the PCR amplification product was purified by the QIAquick gel extraction kit. This PCR amplification product was named C2NSI117L-F. Next, C2NS Lc 117IL F (5'-GCAGTATGGT AGCTCACCTC TATTCAC-TTT CGGCCCTGGG ACC-3' (SEQ ID NO: 72)) and C2NS EcoRI R (5'-CCGGAATTCA ACACTCTCCC CTGT-TGAAGC TCTTTGTGAC GG-3' (SEQ ID NO: 73)) were used together with the N5KG1-Val C2IgG1NS vector as a template and a cycle of 94° C. for 15 seconds, 60° C. for 30 seconds, and 68° C. for 1 minute was repeated 25 times. This reaction solution was subjected to 0.8% agarose gel electrophoresis and the PCR amplification product was purified by the QIAquick gel extraction kit. This PCR amplification product was named C2NSI117L-R. Next, 5 μL each of 2-time diluted C2NSI117L-F and C2NSI117L-R was placed, and PCR was conduced without primer by repeating a cycle of 94° C. for 15 seconds, 55° C. for 30 seconds, 68° C. 60 seconds 3 times. This reaction solution was heated at 99° C. for 5 minutes and then diluted 5 times, 5 μL of this solution was used as a template, the C2-1 Lc Bgl II F primer and the C2NS EcoRI R primer were used, and a cycle of 94° C. for 15 seconds, 55° C. for 30 seconds, and 68° C. 60 seconds was repeated 25 times. This reaction solution was subjected to 0.8% agarose gel electrophoresis and the PCR amplification product was purified by the QIAquick gel extraction kit. This PCR amplified cDNA fragment was digested with BglII and EcoRI and introduced into the N5KG1-Val Lark vector that had been cleaved by the same enzymes and contained the above C2 heavy chain gene. The DNA nucleotide sequence of the inserted portion was determined and it was confirmed that the sequence that had been amplified by PCR and inserted was identical to the gene sequence used as a template. The obtained plasmid DNA expressing the mutant protein with one amino acid substitution mutant was named N5KG1-Val C2IgG1NS/I117L vector.

Preparation of C2IgG1NS/117IM Vector

C2IgG1NS/I117M in which isoleucine at 117 of the light chain was replaced with methionine was prepared using the N5KG1-Val C2IgG1NS vector prepared in Example 6 as a template by the method described below.

For DNA amplification, KOD-Plus of Toyobo was used. A reaction solution having a composition of 1 μL of cDNA, 5 μL of 10×KOD-Plus Buffer, 5 μL of dNTP mix, 1 μL of KOD-Plus, 2 μL of 25 mM MgSO$_4$, a F primer, and a R primer was prepared in a final volume of 50 μL using double distilled water and subjected to PCR.

C2NS Lc 117IM R (5'-GGTCCCAGGG CCGAAAGTGA ACATAGGTGA GCTACCATAC TGCTG-3' (SEQ ID NO: 74)) was synthesized, the C2NS Lc 117IM R and the C2-1 Lc Bgl II F (5'-AGA GAG AGA GAT CTC TCA CCA TGG AAA CCC CAG CGCAGC TTC TCT TC-3' (SEQ ID NO: 18)) were used, the N5KG1-Val C2IgG1NS vector was used as a template, and a cycle of 94° C. for 15 seconds, 60° C. for 30 seconds, and 68° C. for 1 minute was repeated 25 times. This reaction solution was subjected to 0.8% agarose gel electrophoresis and the PCR amplification product was purified by the QIAquick gel extraction kit. This PCR amplification product was named C2NSI117M-F. Next, C2NS Lc 117IM F (5'-GCAGTATGGT AGCTCACCTA TGT-TCACTTT CGGCCCTGGG ACC-3' (SEQ ID NO: 75)) and C2NS EcoRI R (5'-CCGGAATTCA ACACTCTCCC CTGT-TGAAGC TCTTTGTGAC GG-3' (SEQ ID NO: 76)) were used together with the N5KG1-Val C2IgG1NS vector as a template and a cycle of 94° C. for 15 seconds, 60° C. for 30 seconds, and 68° C. for 1 minute was repeated 25 times. This reaction solution was subjected to 0.8% agarose gel electrophoresis and the PCR amplification product was purified by the QIAquick gel extraction kit. This PCR amplification product was named C2NSI117M-R. Then 5 μL each of 2-time diluted C2NSI117M-F and C2NSI117M-R was placed and a cycle of 94° C. for 15 seconds, 55° C. for 30 seconds, and 68° C. for 60 seconds was repeated 3 times in the absence of a primer. This reaction solution was heated at 99° C. for 5 minutes and then diluted 5 times, 5 μL of this solution was used as a template together with the C2-1 Lc Bgl II F primer and the C2NS EcoRI R primer, and a cycle of 94° C. for 15 seconds, 55° C. for 30 seconds, and 68° C. 60 seconds was repeated 25 times. This reaction solution was subjected to 0.8% agarose gel electrophoresis and the PCR amplification product was purified by the QIAquick gel extraction kit. This PCR-amplified cDNA fragment was digested with BglII and EcoRI and introduced into the N5KG1-Val Lark vector that had been cleaved by the same enzymes and contained the above C2 heavy chain gene. The DNA nucleotide sequence of the inserted portion was determined and it was confirmed that the sequence that had been amplified by PCR and inserted was identical to the gene sequence used as a template. The obtained plasmid DNA expressing the mutant protein with one amino acid substitution was named N5KG1-Val C2IgG1NS/117M vector.

Preparation of Amino Acid-Modified C2IgG1NS

By the method described in Example 7, the C2IgG1NS/I117L vector, the C2IgG1NS/I117M vector, the C2IgG1NS/I117N vector, and the C2IgG1NS/I117C vector were introduced into FreeStyle293 cells (manufactured by Invitrogen) in accordance with the attached instruction manual to express recombinant antibodies. The antibody was purified by the method described in Example 8 of which part was modified. On day 6, the culture supernatant was collected and filtered through Steriflip-GP (MILLIPORE, SCGPOO525) to remove contaminants such as cells and the like. The culture supernatant containing an antibody was affinity purified using Protein A (manufactured by Amersham), PBS as an absorption buffer, and 20 mM sodium citrate buffer (pH 3.4) as an elution buffer. The elution fractions were adjusted to about pH 5.5 by adding 200 mM sodium phosphate buffer (pH 7.0). The prepared antibody solution was concentrated at 3000 rpm using vivaspin 6 (10 KMW cut VIVA SCIENCE, VS0601), PBS was further added, and the mixture was centrifuged to obtain purified antibody replaced with PBS. The concentration of the purified antibody was obtained by measuring the absorbance at 280 nm and calculating 1.45 Optimal density as 1 mg/mL.

Measurement of Content of Aggregate of Amino Acid-Modified C2IgG1 NS

The contents of aggregate of the respective purified antibodies were measured using 10 µg (0.1 mg/mL) of the amino acid-modified antibodies.

The content of aggregate of the antibody solution was analyzed by using a high performance liquid chromatograph (manufactured by Shimadzu), TSK-G3000 SW column (manufactured by Toso), and 20 mM sodium phosphate and 500 mM NaCl pH 7.0 as solvents. Elution positions were compared with a molecular marker for gel filtration HPLC (manufactured by Oriental Yeast) (Cat No. 40403701) to identify a monomer and aggregates of the antibody protein, and the content of the aggregate was calculated from the respective peak areas.

Figure 15:
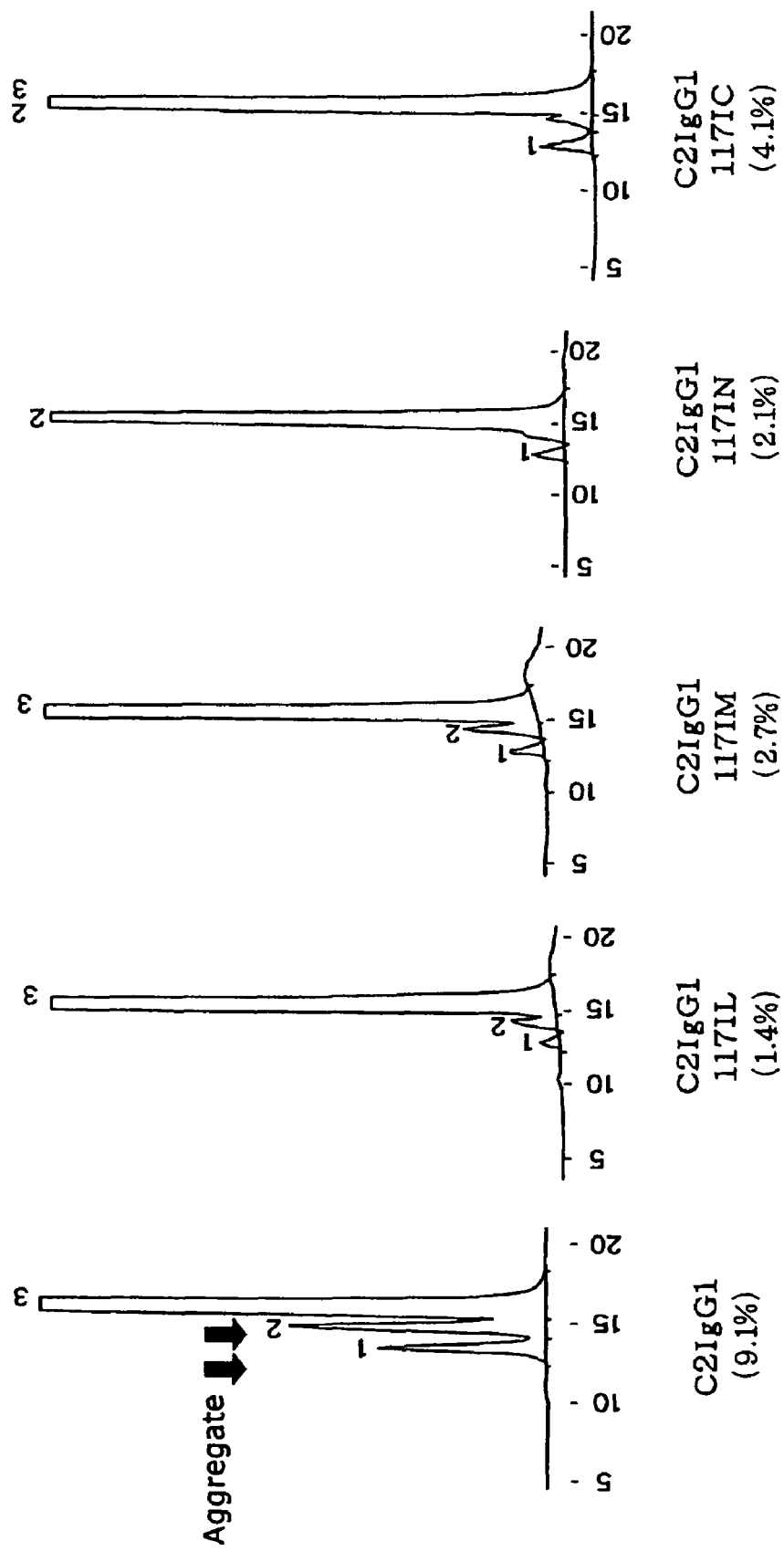
FIG. 15 shows a content of aggregates measured by HPLC in amino-acid modified antibodies of human anti-CD98 monoclonal antibodies C2IgG1NS after the purification thereof.

The results are shown in FIG. 15. FIG. 15 shows that the content of aggregate was decreased by the amino acid modifications above.

Measurement of Amount of Aggregate of Amino Acid-Modified C2IgG1NS

Reactivities of the amino acid-modified C2IgG1NS antibodies to a tumor cell line, a human CD98/human LAT1 enforced expression cell line, and HAEC by FACS in accordance with the methods described in Examples 14 and 15.

Figure 16A:
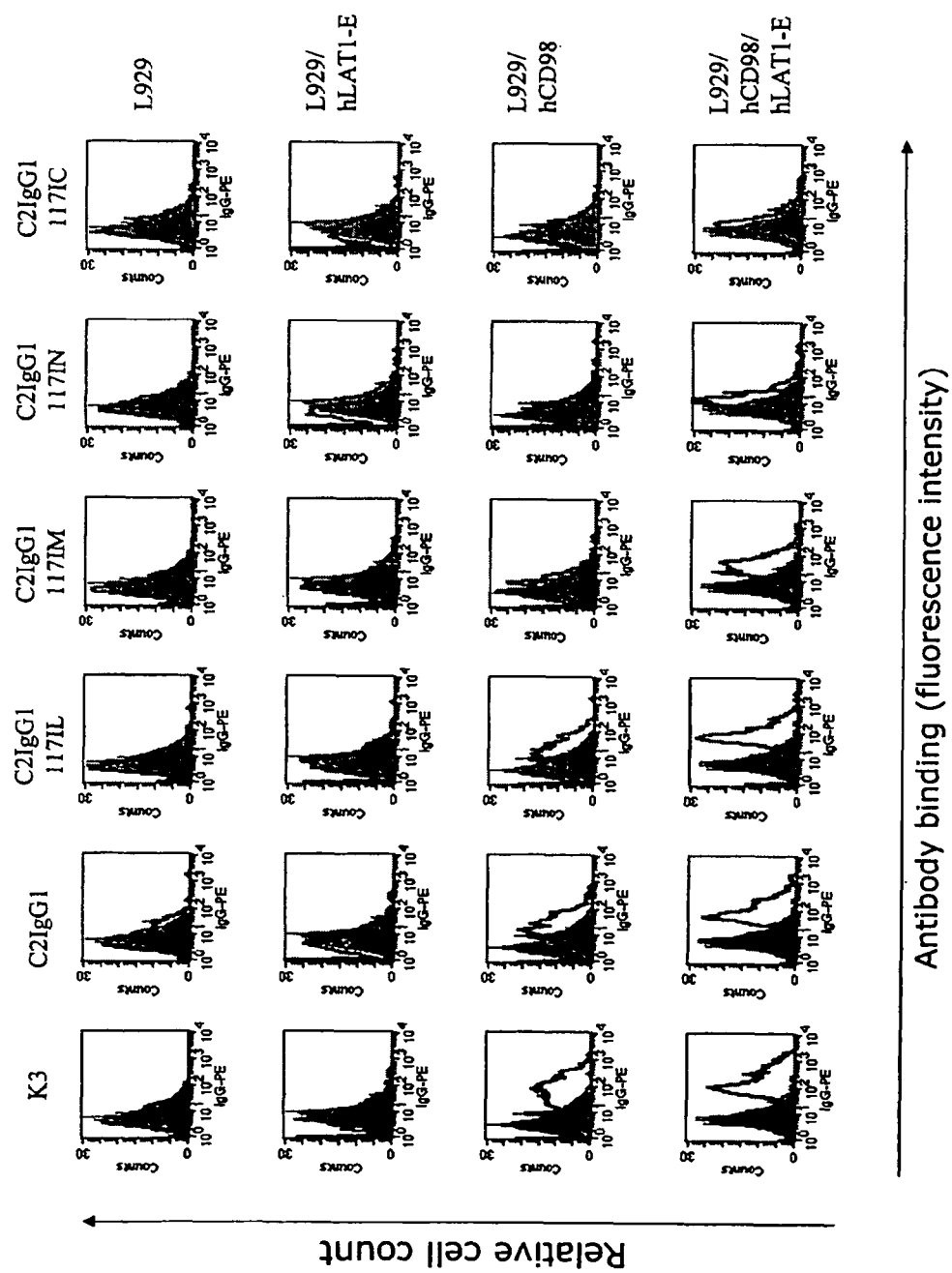
FIG. 16A shows the binding of human anti-CD98 monoclonal antibodies K3 and C2IgG1 as well as each amino-acid modified antibodies of C2IgG1 to human CD98/human LAT1-expressing L929 cell line.
Figure 16B:
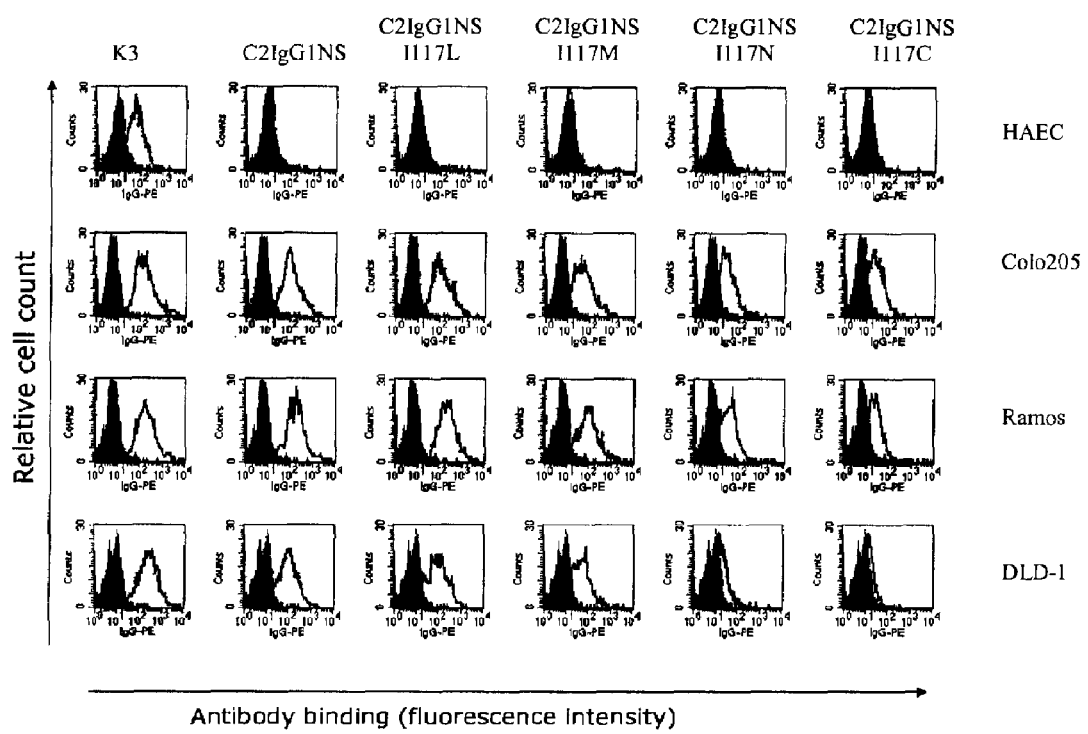
FIG. 16B shows the binding of human anti-CD98 monoclonal antibodies K3 and C2IgG1 as well as each amino-acid modified antibodies of C2IgG1 to a human colorectal cancer cell line (DLD-1), a Burkitt's lymphoma cell line (Ramos), a human colorectal cancer cell line (Colo205), and human aortic endothelial cells (HAEC).

The results are shown in FIG. 16A and FIG. 16B. The above amino acid-modified antibodies, especially C2IgG1NS/I117L, bound to L929 cells forcibly expressing human CD98 and human LAT1, but did not bound to untreated L929 (FIG. 16A). In addition, these amino acid-modified antibodies did not bind to HAEC, but bound to various cancer cells such as colo204, Ramos, and DLD-1 (FIG. 16B).

Figure 2A:
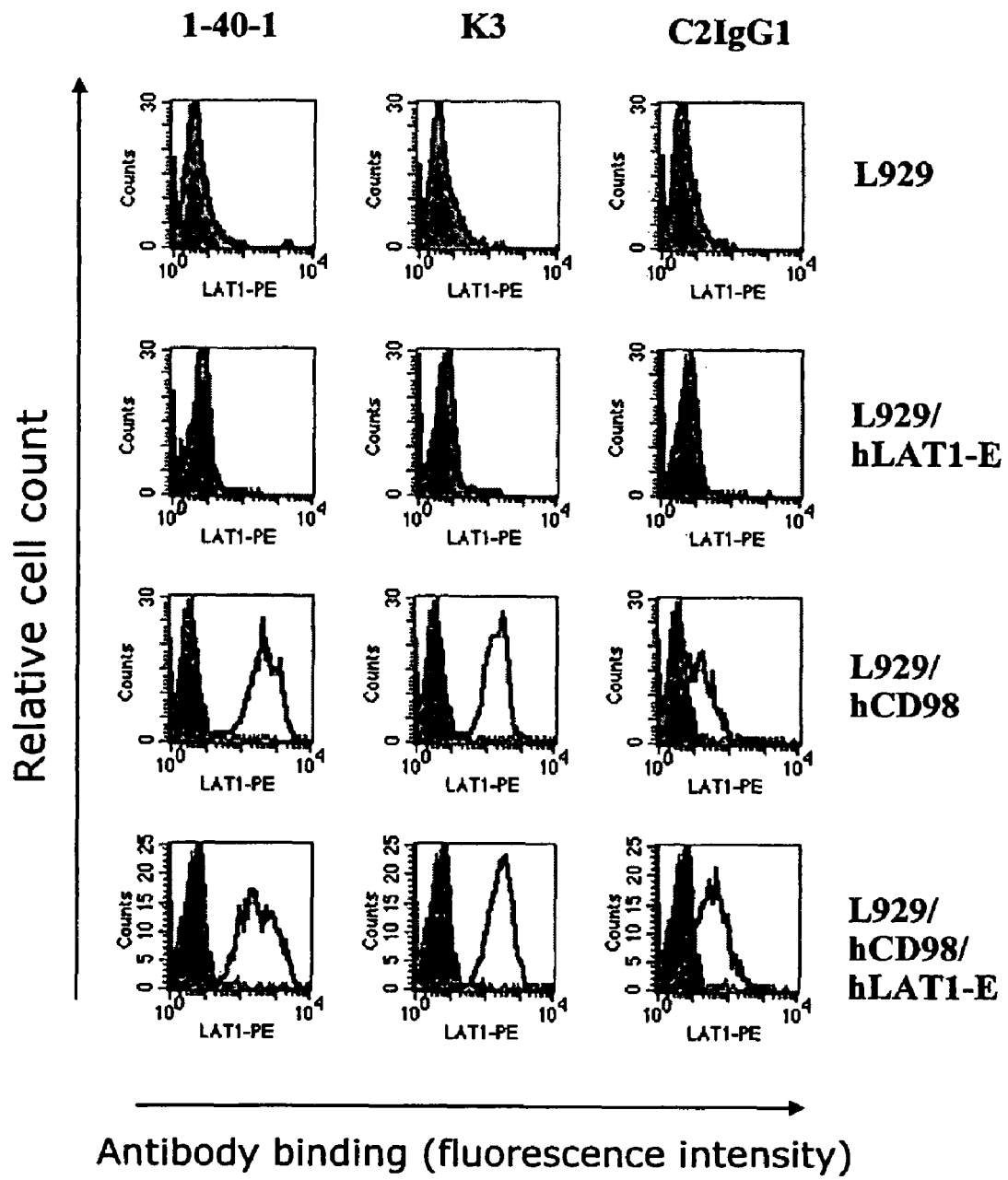
FIG. 2A shows the binding of human anti-CD98 monoclonal antibodies to a human CD98-expressing L929 cell line.
Figure 2B:
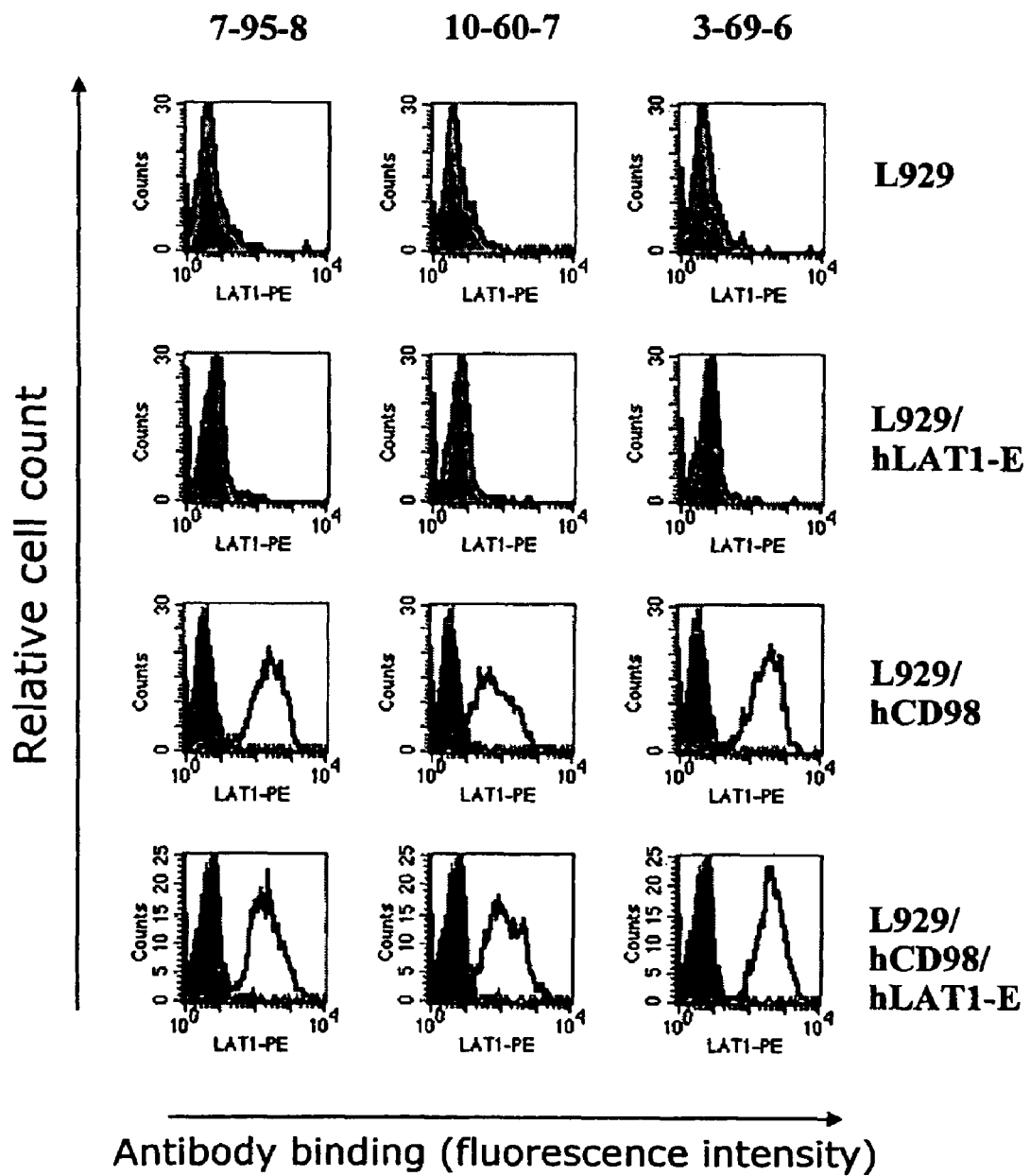
FIG. 2B shows the binding of human anti-CD98 monoclonal antibodies to a human CD98-expressing L929 cell line.

Since these results are similar to the binding property of C2IgG1 shown in FIG. 2A and FIG. 8, it is considered that the above amino acid-modified antibodies, especially C2IgG1NS/I117L, has a low aggregate content, has binding specificity to cancer cells similarly to C2IgG1, and may be expected to exhibit anti-tumor activity similarly to C2IgG1.

<Amino Acid Sequence of the Heavy Chain Variable Region of Amino Acid-Modified C2IgG1Ns (Identical to Amino Acid Sequence of C2IgG1 Heavy Chain Variable Region)> (SEQ ID NO: 43)

STTMKHLWFFLLLLVAAPRWVLSQLQLQESGPGLVKPSETLSLTCTVSGG

SISSSSYYWGWIRQPPGKGLEWIGSIYYSGSTYYNPSLKSRVTISVDTS

KSQFFLKLSSVTAADTAVYYCARQGTGLALFDYWGQGTLVTVSS

<Nucleotide Sequence of the Heavy Chain Variable Region of Amino Acid-Modified C2IgG1Ns (Identical to Nucleotide Sequence of C2IgG1Ns Heavy Chain Variable Region)> (SEQ ID NO: 42)

GTCGACCACCATGAAGCACCTGTGGTTCTTCCTCCTGCTGGTGGCGG

CTCCCAGATGGGTCCTGTCCCAGCTGCAGCTGCAGGAGTCGGGCCCA

GGACTGGTGAAGCCTTCGGAGACCCTGTCCCTCACCTGCACTGTCTC

TGGTGGCTCCATCAGCAGTAGTAGTTACTACTGGGGCTGGATCCGCCA

GCCCCCAGGGAAGGGGCTGGAGTGGATTGGGAGTATCTATTATAGTG

GGAGTACCTACTACAACCCGTCCCTCAAGAGTCGAGTCACCATATCCG

TAGACACGTCCAAGAACCAGTTCTCCCTGAAGCTGAGCTCTGTGACC

GCCGCAGACACGGCTGTGTATTACTGTGCGAGACAAGGGACGGGGC

TCGCCCTATTTGACTACTGGGGCCAGGGAACCCTGGTCACCGTCTCCT

CA

<Amino Acid Sequence of the Light Chain Variable Region of C2IgG1NS/117IL> (SEQ ID NO: 77)

RSLTMETPAQLLFLLLLWLPDTTGEIVLTQSPGTLSLSPGERATLSCRAS

QSVSSSFLAWYQQKPGQAPRLLIYGASSRATGIPDRFSGSGSGTDFTLTI

SRLEPEDFAVYYCQQYGSSPLFTFGPGTKVDIK

<Nucleotide Sequence of the Light Chain Variable Region of C2IgG1NS/117IL> (SEQ ID NO: 78)

AGATCTCTCACCATGGAAACCCCAGCGCAGCTTCTCTTCCTCCTGCTA

CTCTGGCTCCCAGATACCACCGGAGAAATTGTGTTGACGCAGTCTCCA

GGCACCCTGTCTTTGTCTCCAGGGGAAAGAGCCACCCTCTCCTGCAG

GGCCAGTCAGAGTGTTAGCAGCAGCTTCTTAGCCTGGTACCAGCAGA

AACCTGGCCAGGCTCCCAGGCTCCTCATCTATGGTGCATCCAGCAGG

GCCACTGGCATCCCAGACAGGTTCAGTGGCAGTGGGTCTGGGACAG

ACTTCACTCTCACCATCAGCAGACTGGAGCCTGAAGATTTCGCAGTGT

ATTACTGTCAGCAGTATGGTAGCTCACCTCTATTCACTTTCGGCCCTGG

GACCAAAGTGGATATCAAA

<Amino Acid Sequence of the Light Chain Variable Region of C2IgG1NS/117IM> (SEQ ID NO: 79)

RSLTMETPAQLLFLLLLWLPDTTGEIVLTQSPGTLSLSPGERATLSCRAS

QSVSSSFLAWYQQKPGQAPRLLIYGASSRATGIPDRFSGSGSGTDFTLTI

SRLEPEDFAVYYCQQYGSSPMFTFGPGTKVDIK

<Nucleotide Sequence of the Light Chain Variable Region of C2IgG1NS/117IM> (SEQ ID NO: 80)

AGATCTCTCACCATGGAAACCCCAGCGCAGCTTCTCTTCCTCCTGCTA

CTCTGGCTCCCAGATACCACCGGAGAAATTGTGTTGACGCAGTCTCCA

GGCACCCTGTCTTTGTCTCCAGGGGAAAGAGCCACCCTCTCCTGCAG

GGCCAGTCAGAGTGTTAGCAGCAGCTTCTTAGCCTGGTACCAGCAGA

AACCTGGCCAGGCTCCCAGGCTCCTCATCTATGGTGCATCCAGCAGG

GCCACTGGCATCCCAGACAGGTTCAGTGGCAGTGGGTCTGGGACAG

ACTTCACTCTCACCATCAGCAGACTGGAGCCTGAAGATTTCGCAGTGT

ATTACTGTCAGCAGTATGGTAGCTCACCTATGTTCACTTTCGGCCCTGG

GACCAAAGTGGATATCAAA

<Amino Acid Sequence of the Light Chain Variable Region of C2IgG1NS/117IN> (SEQ ID NO: 81)

RSLTMETPAQLLFLLLLWLPDTTGEIVLTQSPGTLSLSPGERATLSCRAS

QSVSSSFLAWYQQKPGQAPRLLIYGASSRATGIPDRFSGSGSGTDFTLTI

SRLEPEDFAVYYCQQYGSSPNFTFGPGTKVDIK

<Nucleotide Sequence of the Light Chain Variable Region of C2IgG1NS/117IN> (SEQ ID NO: 82)

AGATCTCTCACCATGGAAACCCCAGCGCAGCTTCTCTTCCTCCTGCTA

CTCTGGCTCCCAGATACCACCGGAGAAATTGTGTTGACGCAGTCTCCA

GGCACCCTGTCTTTGTCTCCAGGGGAAAGAGCCACCCTCTCCTGCAG

GGCCAGTCAGAGTGTTAGCAGCAGCTTCTTAGCCTGGTACCAGCAGA

AACCTGGCCAGGCTCCCAGGCTCCTCATCTATGGTGCATCCAGCAGG

GCCACTGGCATCCCAGACAGGTTCAGTGGCAGTGGGTCTGGGACAG

ACTTCACTCTCACCATCAGCAGACTGGAGCCTGAAGATTTCGCAGTGT

ATTACTGTCAGCAGTATGGTAGCTCACCTAATTTCACTTTCGGCCCTGG

GACCAAAGTGGATATCAAA

<Amino Acid Sequence of the Light Chain Variable Region of C2IgG1NS/117IC> (SEQ ID NO: 83)

RSLTMETPAQLLFLLLLWLPDTTGEIVLTQSPGTLSLSPGERATLSCRAS

QSVSSSFLAWYQQKPGQAPRLLIYGASSRATGIPDRFSGSGSGTDFTLTI

SRLEPEDFAVYYCQQYGSSPCFTFGPGTKVDIK

<Nucleotide Sequence of the Light Chain Variable Region of C2IgG1NS/117IC> (SEQ ID NO: 84)

AGATCTCTCACCATGGAAACCCCAGCGCAGCTTCTCTTCCTCCTGCTA

CTCTGGCTCCCAGATACCACCGGAGAAATTGTGTTGACGCAGTCTCCA

GGCACCCTGTCTTTGTCTCCAGGGGAAAGAGCCACCCTCTCCTGCAG

GGCCAGTCAGAGTGTTAGCAGCAGCTTCTTAGCCTGGTACCAGCAGA

AACCTGGCCAGGCTCCCAGGCTCCTCATCTATGGTGCATCCAGCAGG

GCCACTGGCATCCCAGACAGGTTCAGTGGCAGTGGGTCTGGGACAG

ACTTCACTCTCACCATCAGCAGACTGGAGCCTGAAGATTTCGCAGTGT

ATTACTGTCAGCAGTATGGTAGCTCACCTTGTTTCACTTTCGGCCCTGG

GACCAAAGTGGATATCAAA

```
                        SEQUENCE LISTING

<160> NUMBER OF SEQ ID NOS: 85

<210> SEQ ID NO 1
<211> LENGTH: 26
<212> TYPE: DNA
<213> ORGANISM: Artificial
<220> FEATURE:
<223> OTHER INFORMATION: Primer

<400> SEQUENCE: 1
gttgaagctc tttgtgacgg gcgagc                                          26

<210> SEQ ID NO 2
<211> LENGTH: 30
```

```
<212> TYPE: DNA
<213> ORGANISM: Artificial
<220> FEATURE:
<223> OTHER INFORMATION: Primer

<400> SEQUENCE: 2
aggcacacaa cagaggcagt tccagatttc                                    30

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
attaaccctc actaaaggga                                               20

<210> SEQ ID NO 4
<211> LENGTH: 45
<212> TYPE: DNA
<213> ORGANISM: Artificial
<220> FEATURE:
<223> OTHER INFORMATION: Primer

<400> SEQUENCE: 4
agagagagag atctctcacc atggaagccc cagctcagct tctct                   45

<210> SEQ ID NO 5
<211> LENGTH: 42
<212> TYPE: DNA
<213> ORGANISM: Artificial
<220> FEATURE:
<223> OTHER INFORMATION: Primer

<400> SEQUENCE: 5
agagagagag cgtacgttta atctccagtc gtgtcccttg gc                      42

<210> SEQ ID NO 6
<211> LENGTH: 31
<212> TYPE: DNA
<213> ORGANISM: Artificial
<220> FEATURE:
<223> OTHER INFORMATION: Primer

<400> SEQUENCE: 6
tcttgtccac cttggtgttg ctgggcttgt g                                  31

<210> SEQ ID NO 7
<211> LENGTH: 31
<212> TYPE: DNA
<213> ORGANISM: Artificial
<220> FEATURE:
<223> OTHER INFORMATION: Primer

<400> SEQUENCE: 7
tgcacgccgc tggtcagggc gcctgagttc c                                  31

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
gctggagggc acggtcacca cgctg                                         25
```

<210> SEQ ID NO 9
<211> LENGTH: 50
<212> TYPE: DNA
<213> ORGANISM: Artificial
<220> FEATURE:
<223> OTHER INFORMATION: Primer

<400> SEQUENCE: 9
agagagagag gtcgaccacc atggggtcaa ccgccatcct cgccctcctc                50

<210> SEQ ID NO 10
<211> LENGTH: 39
<212> TYPE: DNA
<213> ORGANISM: Artificial
<220> FEATURE:
<223> OTHER INFORMATION: Primer

<400> SEQUENCE: 10
agagagagag gctagctgag gagacggtga ccagggttc                            39

<210> SEQ ID NO 11
<211> LENGTH: 45
<212> TYPE: DNA
<213> ORGANISM: Artificial
<220> FEATURE:
<223> OTHER INFORMATION: Primer

<400> SEQUENCE: 11
agagagagag gtcgaccacc atggagtttg ggctgagctg ggttt                     45

<210> SEQ ID NO 12
<211> LENGTH: 42
<212> TYPE: DNA
<213> ORGANISM: Artificial
<220> FEATURE:
<223> OTHER INFORMATION: Primer

<400> SEQUENCE: 12
agagagagag cgtacgtttg atttccacct tggtcccttg gc                        42

<210> SEQ ID NO 13
<211> LENGTH: 16
<212> TYPE: DNA
<213> ORGANISM: Artificial
<220> FEATURE:
<223> OTHER INFORMATION: Primer

<400> SEQUENCE: 13
gtaaaacgac ggccag                                                     16

<210> SEQ ID NO 14
<211> LENGTH: 17
<212> TYPE: DNA
<213> ORGANISM: Artificial
<220> FEATURE:
<223> OTHER INFORMATION: Primer

<400> SEQUENCE: 14
caggaaacag ctatgac                                                    17

<210> SEQ ID NO 15
<211> LENGTH: 47
<212> TYPE: DNA
<213> ORGANISM: Artificial
<220> FEATURE:
<223> OTHER INFORMATION: Primer

```
<400> SEQUENCE: 15
agagagagag atctctcacc atggaaaccc cagcgcagct tctcttc          47

<210> SEQ ID NO 16
<211> LENGTH: 40
<212> TYPE: DNA
<213> ORGANISM: Artificial
<220> FEATURE:
<223> OTHER INFORMATION: Primer

<400> SEQUENCE: 16
agagagagag cgtacgtttg atctccagct tggtccctg                   40

<210> SEQ ID NO 17
<211> LENGTH: 41
<212> TYPE: DNA
<213> ORGANISM: Artificial
<220> FEATURE:
<223> OTHER INFORMATION: Primer

<400> SEQUENCE: 17
agagagagag gtcgacccac catggactgg agcatccttt t                41

<210> SEQ ID NO 18
<211> LENGTH: 47
<212> TYPE: DNA
<213> ORGANISM: Artificial
<220> FEATURE:
<223> OTHER INFORMATION: Primer

<400> SEQUENCE: 18
agagagagag atctctcacc atggaaaccc cagcgcagct tctcttc          47

<210> SEQ ID NO 19
<211> LENGTH: 41
<212> TYPE: DNA
<213> ORGANISM: Artificial
<220> FEATURE:
<223> OTHER INFORMATION: Primer

<400> SEQUENCE: 19
agagagagag cgtacgtttg atatccactt tggtcccagg g                41

<210> SEQ ID NO 20
<211> LENGTH: 24
<212> TYPE: DNA
<213> ORGANISM: Artificial
<220> FEATURE:
<223> OTHER INFORMATION: Primer

<400> SEQUENCE: 20
ggcgaagacc cggatggcta tgtc                                   24

<210> SEQ ID NO 21
<211> LENGTH: 24
<212> TYPE: DNA
<213> ORGANISM: Artificial
<220> FEATURE:
<223> OTHER INFORMATION: Primer

<400> SEQUENCE: 21
aaacccgtgg cctggcagat gagc                                   24

<210> SEQ ID NO 22
<211> LENGTH: 49
```

-continued

<212> TYPE: DNA
<213> ORGANISM: Artificial
<220> FEATURE:
<223> OTHER INFORMATION: Primer

<400> SEQUENCE: 22
agagagagag gtcgaccacc atgaagcacc tgtggttctt cctcctgct          49

<210> SEQ ID NO 23
<211> LENGTH: 30
<212> TYPE: DNA
<213> ORGANISM: Artificial
<220> FEATURE:
<223> OTHER INFORMATION: Primer

<400> SEQUENCE: 23
cgtccaagaa ccagttctcc ctgaagctga                               30

<210> SEQ ID NO 24
<211> LENGTH: 30
<212> TYPE: DNA
<213> ORGANISM: Artificial
<220> FEATURE:
<223> OTHER INFORMATION: Primer

<400> SEQUENCE: 24
tcagcttcag ggagaactgg ttcttggacg                               30

<210> SEQ ID NO 25
<211> LENGTH: 54
<212> TYPE: DNA
<213> ORGANISM: Artificial
<220> FEATURE:
<223> OTHER INFORMATION: Primer

<400> SEQUENCE: 25
caccggttcg gggaagtagt ccttgacgag gcagcaaacg gccacgctgc tcgt    54

<210> SEQ ID NO 26
<211> LENGTH: 54
<212> TYPE: DNA
<213> ORGANISM: Artificial
<220> FEATURE:
<223> OTHER INFORMATION: Primer

<400> SEQUENCE: 26
acgagcagcg tggccgttgg ctgcctcgtc aaggactact ccccgaaccg gtg     54

<210> SEQ ID NO 27
<211> LENGTH: 39
<212> TYPE: DNA
<213> ORGANISM: Artificial
<220> FEATURE:
<223> OTHER INFORMATION: Primer

<400> SEQUENCE: 27
cgcggatcct catcatttac ccggagacag ggagaggct                     39

<210> SEQ ID NO 28
<211> LENGTH: 434
<212> TYPE: DNA
<213> ORGANISM: Artificial
<220> FEATURE:
<223> OTHER INFORMATION: H-chain variable region of antibody K3

<400> SEQUENCE: 28
agagagagag gtcgaccacc atggggtcaa ccgccatcct cgccctcctc ctggctgttc    60

```
tccaaggagt ctgtgccgag gtgcagctgg tgcagtctgg agcagaagtg aaaaagcccg      120
gggagtctct gaagatctcc tgtaagggtt ctggatacag gtttaccgac tactggatcg      180
gctgggtgcg ccagatgccc gggaaaggcc tggagtggat ggggatcttc tatcctggtg      240
actctgatgc cagatacagc ccgtccttcc aaggccaggt caccatctca gccgacaagt      300
ccatcaacac cgcctacctg cagtggagca gcctgaaggc ctcggacacc gccatgtatt      360
attgtgcgag acggcgagat atagtgggag gtactgacta ctggggccag ggaaccctgg      420
tcaccgtctc ctca                                                       434
```

<210> SEQ ID NO 29
<211> LENGTH: 138
<212> TYPE: PRT
<213> ORGANISM: Artificial
<220> FEATURE:
<223> OTHER INFORMATION: H-chain variable region of antibody K3

<400> SEQUENCE: 29

```
Met Gly Ser Thr Ala Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Arg Phe
        35                  40                  45

Thr Asp Tyr Trp Ile Gly Trp Val Arg Gln Met Pro Gly Lys Gly Leu
    50                  55                  60

Glu Trp Met Gly Ile Phe Tyr Pro Gly Asp Ser Asp Ala Arg Tyr Ser
65                  70                  75                  80

Pro Ser Phe Gln Gly Gln Val Thr Ile Ser Ala Asp Lys Ser Ile Asn
                85                  90                  95

Thr Ala Tyr Leu Gln Trp Ser Ser Leu Lys Ala Ser Asp Thr Ala Met
            100                 105                 110

Tyr Tyr Cys Ala Arg Arg Arg Asp Ile Val Gly Gly Thr Asp Tyr Trp
        115                 120                 125

Gly Gln Gly Thr Leu Val Thr Val Ser Ser
    130                 135
```

<210> SEQ ID NO 30
<211> LENGTH: 398
<212> TYPE: DNA
<213> ORGANISM: Artificial
<220> FEATURE:
<223> OTHER INFORMATION: L-chain variable region of antibody K3

<400> SEQUENCE: 30

```
agagagagag atctctcacc atggaagccc agctcagct tctcttcctc ctgctactct       60
ggctcccaga taccaccgga gaaattgtgt tgacacagtc tccagccacc ctgtctttgt      120
ctccagggga aagagccacc ctctcctgca gggccagtca gagtgttagc agctacttag      180
actggtacca acagaaacct ggccaggctc ccaggctcct catctatgat gcatccagca      240
gggccactgg catcccagcc aggttcagtg gcagtgggtc tgggacagac ttcactctca      300
ccatcagcag cctagagcct gaagattttg cagtttatta ctgtcagcag cgtagcaact      360
ggatcacctt cggccaaggg acacgactgg agattaaa                              398
```

<210> SEQ ID NO 31
<211> LENGTH: 126
<212> TYPE: PRT

<213> ORGANISM: Artificial
<220> FEATURE:
<223> OTHER INFORMATION: L-chain variable region of antibody K3

<400> SEQUENCE: 31

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Asp Trp Tyr Gln Gln Lys Pro Gly Gln Ala Pro
    50                  55                  60

Arg Leu Leu Ile Tyr Asp Ala Ser Ser Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Ile Thr Phe Gly Gln Gly Thr Arg Leu Glu Ile Lys
        115                 120                 125

<210> SEQ ID NO 32
<211> LENGTH: 437
<212> TYPE: DNA
<213> ORGANISM: Artificial
<220> FEATURE:
<223> OTHER INFORMATION: H-chain variable region of antibody 1-40-1

<400> SEQUENCE: 32
agagagagag gtcgaccacc atggagtttg gctgagctg ggttttcctt gttgctattt    60
taaaaggtgt ccagtgtgag gtgcagctgg tggagtctgg ggaggtgtg gtacggcctg    120
gggggtccct gagactctcc tgtgcagcct ctggattcac ctttgatgat tatggcatga    180
cctgggtccg ccaagctcca gggaaggggc tggagtgggt ctctactatt agttggaatg    240
gtggtggcac aggttatgca gactctgtga agggccgatt caccatctcc agagacaacg    300
ccaagaactc cctgtatctg caaatgaaca gtctgagagc cgaggacacg gccttgtatt    360
actgtgcggg atattgtatt attaccggct gctatgcgga ctactggggc cagggaaccc    420
tggtcaccgt ctcctca                                                  437

<210> SEQ ID NO 33
<211> LENGTH: 139
<212> TYPE: PRT
<213> ORGANISM: Artificial
<220> FEATURE:
<223> OTHER INFORMATION: H-chain variable region of antibody 1-40-1

<400> SEQUENCE: 33

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Val Val Arg
            20                  25                  30

Pro Gly Gly Ser Leu Arg Leu Ser Cys Ala Ala Ser Gly Phe Thr Phe
        35                  40                  45

Asp Asp Tyr Gly Met Thr Trp Val Arg Gln Ala Pro Gly Lys Gly Leu
    50                  55                  60

Glu Trp Val Ser Thr Ile Ser Trp Asn Gly Gly Gly Thr Gly Tyr Ala
65                  70                  75                  80

```
Asp Ser Val Lys Gly Arg Phe Thr Ile Ser Arg Asp Asn Ala Lys Asn
            85                  90                  95

Ser Leu Tyr Leu Gln Met Asn Ser Leu Arg Ala Glu Asp Thr Ala Leu
            100                 105                 110

Tyr Tyr Cys Ala Gly Tyr Cys Ile Ile Thr Gly Cys Tyr Ala Asp Tyr
            115                 120                 125

Trp Gly Gln Gly Thr Leu Val Thr Val Ser Ser
    130                 135
```

<210> SEQ ID NO 34
<211> LENGTH: 398
<212> TYPE: DNA
<213> ORGANISM: Artificial
<220> FEATURE:
<223> OTHER INFORMATION: L-chain variable region of antibody 1-40-1

<400> SEQUENCE: 34

```
agagagagag atctctcacc atggaagccc cagctcagct tctcttcctc ctgctactct      60
ggctcccaga taccaccgga gaaattgtgt tgacacagtc tccagccacc ctgtctttgt     120
ctccagggga aagagccacc ctctcctgca gggccagtca gagtgttagc agctacttag     180
cctggtacca acagaaacct ggccaggctc ccaggctcct catctatgat gcatccaaca     240
gggccactgg catcccagcc aggttcagtg gcagtgggtc tgggacagac ttcactctca     300
ccatcagcag cctagagcct gaagattttg cagtttatta ctgtcagcag cgtagcaact     360
ggtggacgtt cggccaaggg accaaggtgg aaatcaaa                             398
```

<210> SEQ ID NO 35
<211> LENGTH: 126
<212> TYPE: PRT
<213> ORGANISM: Artificial
<220> FEATURE:
<223> OTHER INFORMATION: L-chain variable region of antibody 1-40-1

<400> SEQUENCE: 35

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
            85                  90                  95

Ser Leu Glu Pro Glu Asp Phe Ala Val Tyr Tyr Cys Gln Gln Arg Ser
            100                 105                 110

Asn Trp Trp Thr Phe Gly Gln Gly Thr Lys Val Glu Ile Lys
            115                 120                 125
```

<210> SEQ ID NO 36
<211> LENGTH: 431
<212> TYPE: DNA
<213> ORGANISM: Artificial
<220> FEATURE:
<223> OTHER INFORMATION: H-chain variable region of antibody 3-69-6

<400> SEQUENCE: 36

```
gtcgacccac catggactgg acctggagca tccttttctt ggtggcagca gcaacaggtg     60
cccactccca ggttcaactg gtgcagtctg gagctgaggt gaagaagcct ggggcctcag    120
tgaaggtctc ctgtaaggct tctggttaca cctttaccag ctatggtatc agctggatgc    180
gacaggcccc tggacaaggg cttgagtgga tgggatggat cagcgcttac aatggtaata    240
cgaactatgt acagaagttc caggacagag tcaccatgac cagagacaca tccacgagca    300
cagcctacat ggagctgagg agcctgagat ctgacgacac ggccgtgtat tactgtgcga    360
gagatcgggg cagcaattgg tatgggtggt tcgaccctg ggccaggga accctggtca      420 ccgtctcctc a                                                         431

<210> SEQ ID NO 37
<211> LENGTH: 144
<212> TYPE: PRT
<213> ORGANISM: Artificial
<220> FEATURE:
<223> OTHER INFORMATION: H-chain variable region of antibody 3-69-6

<400> SEQUENCE: 37

Arg Arg Pro Thr Met Asp Trp Thr Trp Ser Ile Leu Phe Leu Val Ala
1               5                   10                  15

Ala Ala Thr Gly Ala His Ser Gln Val Gln Leu Val Gln Ser Gly Ala
            20                  25                  30

Glu Val Lys Lys Pro Gly Ala Ser Val Lys Val Ser Cys Lys Ala Ser
        35                  40                  45

Gly Tyr Thr Phe Thr Ser Tyr Gly Ile Ser Trp Met Arg Gln Ala Pro
    50                  55                  60

Gly Gln Gly Leu Glu Trp Met Gly Trp Ile Ser Ala Tyr Asn Gly Asn
65                  70                  75                  80

Thr Asn Tyr Val Gln Lys Phe Gln Asp Arg Val Thr Met Thr Arg Asp
                85                  90                  95

Thr Ser Thr Ser Thr Ala Tyr Met Glu Leu Arg Ser Leu Arg Ser Asp
            100                 105                 110

Asp Thr Ala Val Tyr Tyr Cys Ala Arg Asp Arg Gly Ser Asn Trp Tyr
        115                 120                 125

Gly Trp Phe Asp Pro Trp Gly Gln Gly Thr Leu Val Thr Val Ser Ser
    130                 135                 140

<210> SEQ ID NO 38
<211> LENGTH: 393
<212> TYPE: DNA
<213> ORGANISM: Artificial
<220> FEATURE:
<223> OTHER INFORMATION: L-chain variable region of antibody 3-69-6

<400> SEQUENCE: 38
agatctctca ccatggaaac cccagcgcag cttctcttcc tcctgctact ctggctccca     60
gataccaccg gagaaattgt gttgacgcag tctccaggca ccctgtcttt gtctccaggg    120
gaaagagcca ccctctcctg cagggccagt cagagtgtta gcagcagcta cttagcctgg    180
taccagcaga aacctggcca ggctcccagg ctcctcatct atggtgcatc cagcagggcc    240
actggcatcc cagacaggtt cagtggcagt gggtctggga cagacttcac tctcaccatc    300
agcagactgg agcctgaaga ttttgcagtg tattactgtc agcagtatgg tagctcgtac    360
acttttggcc aggggaccaa gctggagatc aaa                                 393

<210> SEQ ID NO 39
```

```
<211> LENGTH: 131
<212> TYPE: PRT
<213> ORGANISM: Artificial
<220> FEATURE:
<223> OTHER INFORMATION: L-chain variable region of antibody 3-69-6

<400> SEQUENCE: 39

Arg Ser Leu Thr Met Glu Thr Pro Ala Gln Leu Leu Phe Leu Leu Leu
1               5                   10                  15

Leu Trp Leu Pro Asp Thr Thr Gly Glu Ile Val Leu Thr Gln Ser Pro
            20                  25                  30

Gly Thr Leu Ser Leu Ser Pro Gly Glu Arg Ala Thr Leu Ser Cys Arg
        35                  40                  45

Ala Ser Gln Ser Val Ser Ser Tyr Leu Ala Trp Tyr Gln Gln Lys
    50                  55                  60

Pro Gly Gln Ala Pro Arg Leu Leu Ile Tyr Gly Ala Ser Ser Arg Ala
65                  70                  75                  80

Thr Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys Gln Gln Tyr Gly Ser Ser Tyr Thr Phe Gly Gln Gly Thr Lys Leu
        115                 120                 125

Glu Ile Lys
    130

<210> SEQ ID NO 40
<211> LENGTH: 427
<212> TYPE: DNA
<213> ORGANISM: Artificial
<220> FEATURE:
<223> OTHER INFORMATION: H-chain variable region of antibody C2IgG1

<400> SEQUENCE: 40
gtcgaccacc atgaagcacc tgtggttctt cctcctgctg gtggcggctc ccagatgggt      60
cctgtcccag ctgcagctgc aggagtcggg cccaggactg gtgaagcctt cggagaccct     120
gtccctcacc tgcactgtct ctggtggctc catcagcagt agtagttact actggggctg     180
gatccgccag cccccaggga aggggctgga gtggattggg agtatctatt atagtgggag     240
tacctactac aacccgtccc tcaagagtcg agtcaccata tccgtagaca cgtccaagag     300
ccagttcttc ctgaagctga gctctgtgac cgccgcagac acggctgtgt attactgtgc     360
gagacaaggg acggggctcg ccctatttga ctactggggc cagggaaccc tggtcaccgt     420
ctcctca                                                               427

<210> SEQ ID NO 41
<211> LENGTH: 142
<212> TYPE: PRT
<213> ORGANISM: Artificial
<220> FEATURE:
<223> OTHER INFORMATION: H-chain variable region of antibody C2IgG1

<400> SEQUENCE: 41

Ser Thr Thr Met Lys His Leu Trp Phe Phe Leu Leu Leu Val Ala Ala
1               5                   10                  15

Pro Arg Trp Val Leu Ser Gln Leu Gln Leu Gln Glu Ser Gly Pro Gly
            20                  25                  30

Leu Val Lys Pro Ser Glu Thr Leu Ser Leu Thr Cys Thr Val Ser Gly
        35                  40                  45
```

```
Gly Ser Ile Ser Ser Ser Tyr Tyr Trp Gly Trp Ile Arg Gln Pro
        50                  55                  60

Pro Gly Lys Gly Leu Glu Trp Ile Gly Ser Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Ser Gln Phe Phe Leu Lys Leu Ser Ser Val Thr Ala Ala
                100                 105                 110

Asp Thr Ala Val Tyr Tyr Cys Ala Arg Gln Gly Thr Gly Leu Ala Leu
            115                 120                 125

Phe Asp Tyr Trp Gly Gln Gly Thr Leu Val Thr Val Ser Ser
        130                 135                 140

<210> SEQ ID NO 42
<211> LENGTH: 427
<212> TYPE: DNA
<213> ORGANISM: Artificial
<220> FEATURE:
<223> OTHER INFORMATION: H-chain variable region of antibody C2IgG1NS

<400> SEQUENCE: 42
gtcgaccacc atgaagcacc tgtggttctt cctcctgctg gtggcggctc ccagatgggt      60
cctgtcccag ctgcagctgc aggagtcggg cccaggactg gtgaagcctt cggagaccct     120
gtccctcacc tgcactgtct ctggtggctc catcagcagt agtagttact actggggctg     180
gatccgccag cccccaggga aggggctgga gtggattggg agtatctatt atagtgggag     240
tacctactac aacccgtccc tcaagagtcg agtcaccata tccgtagaca cgtccaagaa     300
ccagttctcc ctgaagctga gctctgtgac cgccgcagac acggctgtgt attactgtgc     360
gagacaaggg acgggctcg ccctatttga ctactggggc cagggaaccc tggtcaccgt     420
ctcctca                                                              427

<210> SEQ ID NO 43
<211> LENGTH: 142
<212> TYPE: PRT
<213> ORGANISM: Artificial
<220> FEATURE:
<223> OTHER INFORMATION: H-chain variable region of antibody C2IgG1NS

<400> SEQUENCE: 43

Ser Thr Thr Met Lys His Leu Trp Phe Phe Leu Leu Val Ala Ala
1               5                   10                  15

Pro Arg Trp Val Leu Ser Gln Leu Gln Leu Gln Glu Ser Gly Pro Gly
                20                  25                  30

Leu Val Lys Pro Ser Glu Thr Leu Ser Leu Thr Cys Thr Val Ser Gly
            35                  40                  45

Gly Ser Ile Ser Ser Ser Tyr Tyr Trp Gly Trp Ile Arg Gln Pro
        50                  55                  60

Pro Gly Lys Gly Leu Glu Trp Ile Gly Ser Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
                100                 105                 110

Asp Thr Ala Val Tyr Tyr Cys Ala Arg Gln Gly Thr Gly Leu Ala Leu
            115                 120                 125

Phe Asp Tyr Trp Gly Gln Gly Thr Leu Val Thr Val Ser Ser
        130                 135                 140
```

<210> SEQ ID NO 44
<211> LENGTH: 505
<212> TYPE: DNA
<213> ORGANISM: Artificial
<220> FEATURE:
<223> OTHER INFORMATION: Partial sequence of antibody C2Ig(Mu)G1 from
      H-chain variable region to IgG1-binding site

<400> SEQUENCE: 44
gtcgaccacc atgaagcacc tgtggttctt cctcctgctg gtggcggctc ccagatgggt    60
cctgtcccag ctgcagctgc aggagtcggg cccaggactg gtgaagcctt cggagaccct   120
gtccctcacc tgcactgtct ctggtggctc catcagcagt agtagttact actggggctg   180
gatccgccag ccccagggga aggggctgga gtggattggg agtatctatt atagtgggag   240
tacctactac aacccgtccc tcaagagtcg agtcaccata tccgtagaca cgtccaagag   300
ccagttcttc ctgaagctga gctctgtgac cgccgcagac acggctgtgt attactgtgc   360
gagacaaggg acggggctcg ccctatttga ctactggggc cagggaaccc tggtcaccgt   420
ctcctcaggg agtgcatccg ccccaaccct tttccccctc gtctcctgtg agaattcccc   480
gtcggatacg agcagcgtgg ccgtt                                          505

<210> SEQ ID NO 45
<211> LENGTH: 168
<212> TYPE: PRT
<213> ORGANISM: Artificial
<220> FEATURE:
<223> OTHER INFORMATION: Partial sequence of antibody C2Ig(Mu)G1 from
      H-chain variable region to IgG1-binding site

<400> SEQUENCE: 45

Ser Thr Thr Met Lys His Leu Trp Phe Phe Leu Leu Leu Val Ala Ala
1               5                   10                  15

Pro Arg Trp Val Leu Ser Gln Leu Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Gly Ser Ile Ser Ser Ser Ser Tyr Tyr Trp Gly Trp Ile Arg Gln Pro
    50                  55                  60

Pro Gly Lys Gly Leu Glu Trp Ile Gly Ser Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Ser Gln Phe Phe Leu Lys Leu Ser Ser Val Thr Ala Ala
            100                 105                 110

Asp Thr Ala Val Tyr Tyr Cys Ala Arg Gln Gly Thr Gly Leu Ala Leu
        115                 120                 125

Phe Asp Tyr Trp Gly Gln Gly Thr Leu Val Thr Val Ser Ser Gly Ser
    130                 135                 140

Ala Ser Ala Pro Thr Leu Phe Pro Leu Val Ser Cys Glu Asn Ser Pro
145                 150                 155                 160

Ser Asp Thr Ser Ser Val Ala Val
                165

<210> SEQ ID NO 46
<211> LENGTH: 399
<212> TYPE: DNA
<213> ORGANISM: Artificial
<220> FEATURE:

<223> OTHER INFORMATION: L-chain variable region of antibody C2IgG1 or
      C2Ig(Mu)G1

<400> SEQUENCE: 46

```
agatctctca ccatggaaac cccagcgcag cttctcttcc tcctgctact ctggctccca      60
gataccaccg gagaaattgt gttgacgcag tctccaggca ccctgtcttt gtctccaggg     120
gaaagagcca ccctctcctg cagggccagt cagagtgtta gcagcagctt cttagcctgg     180
taccagcaga aacctggcca ggctcccagg ctcctcatct atggtgcatc cagcagggcc     240
actggcatcc cagacaggtt cagtggcagt gggtctggga cagacttcac tctcaccatc     300
agcagactgg agcctgaaga tttcgcagtg tattactgtc agcagtatgg tagctcacct     360
atattcactt tcggccctgg gaccaaagtg gatatcaaa                            399
```

<210> SEQ ID NO 47
<211> LENGTH: 133
<212> TYPE: PRT
<213> ORGANISM: Artificial
<220> FEATURE:
<223> OTHER INFORMATION: L-chain variable region of antibody C2IgG1 or
      C2Ig(Mu)G1

<400> SEQUENCE: 47

```
Arg Ser Leu Thr Met Glu Thr Pro Ala Gln Leu Leu Phe Leu Leu Leu
1               5                   10                  15

Leu Trp Leu Pro Asp Thr Thr Gly Glu Ile Val Leu Thr Gln Ser Pro
            20                  25                  30

Gly Thr Leu Ser Leu Ser Pro Gly Glu Arg Ala Thr Leu Ser Cys Arg
        35                  40                  45

Ala Ser Gln Ser Val Ser Ser Phe Leu Ala Trp Tyr Gln Gln Lys
    50                  55                  60

Pro Gly Gln Ala Pro Arg Leu Leu Ile Tyr Gly Ala Ser Ser Arg Ala
65                  70                  75                  80

Thr Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys Gln Gln Tyr Gly Ser Ser Pro Ile Phe Thr Phe Gly Pro Gly Thr
        115                 120                 125

Lys Val Asp Ile Lys
        130
```

<210> SEQ ID NO 48
<211> LENGTH: 864
<212> TYPE: DNA
<213> ORGANISM: Artificial
<220> FEATURE:
<223> OTHER INFORMATION: Sequence of an insert containing variable
      regions and restriction sites in K3/pCR4

<400> SEQUENCE: 48

```
agagagagag atctctcacc atggaagccc cagctcagct tctcttcctc ctgctactct      60
ggctcccaga taccaccgga gaaattgtgt tgacacagtc tccagccacc ctgtctttgt     120
ctccagggga aagagccacc ctctcctgca gggccagtca gagtgttagc agctacttag     180
actggtacca acagaaacct ggccaggctc ccaggctcct catctatgat gcatccagca     240
gggccactgg catcccagcc aggttcagtg gcagtgggtc tgggacagac ttcactctca     300
ccatcagcag cctagagcct gaagattttg cagtttatta ctgtcagcag cgtagcaact     360
```

```
ggatcacctt cggccaaggg acacgactgg agattaaacg tacgctctct ctctagagag      420
agaggtcgac caccatgggg tcaaccgcca tcctcgccct cctcctggct gttctccaag      480
gagtctgtgc cgaggtgcag ctggtgcagt ctggagcaga agtgaaaaag cccggggagt      540
ctctgaagat ctcctgtaag ggttctggat acaggtttac cgactactgg atcggctggg      600
tgcgccagat gcccgggaaa ggcctggagt ggatggggat cttctatcct ggtgactctg      660
atgccagata cagcccgtcc ttccaaggcc aggtcaccat ctcagccgac aagtccatca      720
acaccgccta cctgcagtgg agcagcctga aggcctcgga caccgccatg tattattgtg      780
cgagacggcg agatatagtg ggaggtactg actactgggg ccagggaacc ctggtcaccg      840
tctcctcagc tagcctctct ctct                                            864
```

<210> SEQ ID NO 49
<211> LENGTH: 876
<212> TYPE: DNA
<213> ORGANISM: Artificial
<220> FEATURE:
<223> OTHER INFORMATION: Sequence of an insert containing variable
      regions and restriction sites in C2IgG1/pCR4

<400> SEQUENCE: 49

```
agagagagag atctctcacc atggaaaccc cagcgcagct tctcttcctc ctgctactct      60
ggctcccaga taccaccgga gaaattgtgt tgacgcagtc tccaggcacc ctgtctttgt      120
ctccagggga aagagccacc ctctcctgca gggccagtca gagtgttagc agcagcttct      180
tagcctggta ccagcagaaa cctggccagg ctcccaggct cctcatctat ggtgcatcca      240
gcagggccac tggcatccca gacaggttca gtggcagtgg gtctgggaca gacttcactc      300
tcaccatcag cagactggag cctgaagatt tcgcagtgta ttactgtcag cagtatggta      360
gctcacctat attcactttc ggccctggga ccaaagtgga tatcaaacgt acgctctctc      420
tctagagaga gaggtcgacc accatgaagc acctgtggtt cttcctcctg ctggtggcgg      480
ctcccagatg ggtcctgtcc cagctgcagc tgcaggagtc gggcccagga ctggtgaagc      540
cttcggagac cctgtcctc acctgcactg tctctggtgg ctccatcagc agtagtagtt      600
actactgggg ctggatccgc cagcccccag gaaggggct ggagtggatt gggagtatct      660
attatagtgg gagtacctac tacaacccgt ccctcaagag tcgagtcacc atatccgtag      720
acacgtccaa gagccagttc ttcctgaagc tgagctctgt gaccgccgca gacacggctg      780
tgtattactg tgcgagacaa gggacggggc tcgccctatt tgactactgg ggccagggaa      840
ccctggtcac cgtctcctca gctagcctct ctctct                                876
```

<210> SEQ ID NO 50
<211> LENGTH: 42
<212> TYPE: DNA
<213> ORGANISM: Artificial
<220> FEATURE:
<223> OTHER INFORMATION: Primer

<400> SEQUENCE: 50

```
ccggaattcc caccatgagc caggacaccg aggtggatat ga                        42
```

<210> SEQ ID NO 51
<211> LENGTH: 51
<212> TYPE: DNA
<213> ORGANISM: Artificial
<220> FEATURE:
<223> OTHER INFORMATION: Primer

<400> SEQUENCE: 51

```
aaggaaaaaa gcggccgctc atcaggccgc gtaggggaag cggagcagca g          51
```

<210> SEQ ID NO 52
<211> LENGTH: 44
<212> TYPE: DNA
<213> ORGANISM: Artificial
<220> FEATURE:
<223> OTHER INFORMATION: Primer

<400> SEQUENCE: 52

```
ccggaattcc caccatgagc caggacaccg aagtggacat gaaa                 44
```

<210> SEQ ID NO 53
<211> LENGTH: 50
<212> TYPE: DNA
<213> ORGANISM: Artificial
<220> FEATURE:
<223> OTHER INFORMATION: Primer

<400> SEQUENCE: 53

```
aaggaaaaaa gcggccgctc atcaggccac aaagggaac tgtaacagca            50
```

<210> SEQ ID NO 54
<211> LENGTH: 27
<212> TYPE: DNA
<213> ORGANISM: Artificial
<220> FEATURE:
<223> OTHER INFORMATION: Primer

<400> SEQUENCE: 54

```
tcattctgga ccttactccc aactacc                                    27
```

<210> SEQ ID NO 55
<211> LENGTH: 27
<212> TYPE: DNA
<213> ORGANISM: Artificial
<220> FEATURE:
<223> OTHER INFORMATION: Primer

<400> SEQUENCE: 55

```
ggtagttggg agtaaggtcc agaatga                                    27
```

<210> SEQ ID NO 56
<211> LENGTH: 31
<212> TYPE: DNA
<213> ORGANISM: Artificial
<220> FEATURE:
<223> OTHER INFORMATION: Primer

<400> SEQUENCE: 56

```
tgctcttcac cctgccaggg acccctgttt t                               31
```

<210> SEQ ID NO 57
<211> LENGTH: 31
<212> TYPE: DNA
<213> ORGANISM: Artificial
<220> FEATURE:
<223> OTHER INFORMATION: Primer

<400> SEQUENCE: 57

```
aaaacagggg tccctggcag ggtgaagagc a                               31
```

<210> SEQ ID NO 58
<211> LENGTH: 44
<212> TYPE: DNA
<213> ORGANISM: Artificial

```
<220> FEATURE:
<223> OTHER INFORMATION: Primer

<400> SEQUENCE: 58
agagagagag gctagctgag gagacggtga ccagggttcc ctgg         44

<210> SEQ ID NO 59
<211> LENGTH: 42
<212> TYPE: DNA
<213> ORGANISM: Artificial
<220> FEATURE:
<223> OTHER INFORMATION: Primer

<400> SEQUENCE: 59
ccggaattcc caccatgagc caggacaccg aggtggatat ga           42

<210> SEQ ID NO 60
<211> LENGTH: 51
<212> TYPE: DNA
<213> ORGANISM: Artificial
<220> FEATURE:
<223> OTHER INFORMATION: Primer

<400> SEQUENCE: 60
aaggaaaaaa gcggccgctc atcaggccgc gtaggggaag cggagcagca g  51

<210> SEQ ID NO 61
<211> LENGTH: 45
<212> TYPE: DNA
<213> ORGANISM: Artificial
<220> FEATURE:
<223> OTHER INFORMATION: Primer

<400> SEQUENCE: 61
agtctcttgc aatcggctaa gaagaagagc atccgtgtca ttctg        45

<210> SEQ ID NO 62
<211> LENGTH: 45
<212> TYPE: DNA
<213> ORGANISM: Artificial
<220> FEATURE:
<223> OTHER INFORMATION: Primer

<400> SEQUENCE: 62
cagaatgaca cggatgctct tcttcttagc cgattgcaag agact        45

<210> SEQ ID NO 63
<211> LENGTH: 39
<212> TYPE: DNA
<213> ORGANISM: Artificial
<220> FEATURE:
<223> OTHER INFORMATION: Primer

<400> SEQUENCE: 63
ccggaattcc caccatggcg ggtgcgggcc cgaagcggc              39

<210> SEQ ID NO 64
<211> LENGTH: 39
<212> TYPE: DNA
<213> ORGANISM: Artificial
<220> FEATURE:
<223> OTHER INFORMATION: Primer

<400> SEQUENCE: 64
cggggtaccg tctcctgggg gaccacctgc atgagcttc             39
```

-continued

```
<210> SEQ ID NO 65
<211> LENGTH: 1879
<212> TYPE: DNA
<213> ORGANISM: Homo sapiens
<220> FEATURE:
<221> NAME/KEY: CDS
<222> LOCATION: (112)..(1698)

<400> SEQUENCE: 65
ctgcgcggag gcacagaggc cggggagagc gttctgggtc cgagggtcca ggtaggggtt        60
gagccaccat ctgaccgcaa gctgcgtcgt gtcgccggtt ctgcaggcac c atg agc       117
                                                          Met Ser
                                                            1 cag gac acc gag gtg gat atg aag gag gtg gag ctg aat gag tta gag      165
Gln Asp Thr Glu Val Asp Met Lys Glu Val Glu Leu Asn Glu Leu Glu
        5                  10                  15 ccc gag aag cag ccg atg aac gcg gcg tct ggg gcg gcc atg tcc ctg      213
Pro Glu Lys Gln Pro Met Asn Ala Ala Ser Gly Ala Ala Met Ser Leu
 20                  25                  30 gcg gga gcc gag aag aat ggt ctg gtg aag atc aag gtg gcg gaa gac      261
Ala Gly Ala Glu Lys Asn Gly Leu Val Lys Ile Lys Val Ala Glu Asp
 35                  40                  45                  50 gag gcg gag gcg gca gcc gcg gct aag ttc acg ggc ctg tcc aag gag      309
Glu Ala Glu Ala Ala Ala Ala Ala Lys Phe Thr Gly Leu Ser Lys Glu
                 55                  60                  65 gag ctg ctg aag gtg gca ggc agc ccc ggc tgg gta cgc acc cgc tgg      357
Glu Leu Leu Lys Val Ala Gly Ser Pro Gly Trp Val Arg Thr Arg Trp
             70                  75                  80 gca ctg ctg ctg ctc ttc tgg ctc ggc tgg ctc ggc atg ctt gct ggt      405
Ala Leu Leu Leu Leu Phe Trp Leu Gly Trp Leu Gly Met Leu Ala Gly
         85                  90                  95 gcc gtg gtc ata atc gtg cga gcg ccg cgt tgt cgc gag cta ccg gcg      453
Ala Val Val Ile Ile Val Arg Ala Pro Arg Cys Arg Glu Leu Pro Ala
    100                 105                 110 cag aag tgg tgg cac acg ggc gcc ctc tac cgc atc ggc gac ctt cag      501
Gln Lys Trp Trp His Thr Gly Ala Leu Tyr Arg Ile Gly Asp Leu Gln
115                 120                 125                 130 gcc ttc cag ggc cac ggc gcg ggc aac ctg gcg ggt ctg aag ggg cgt      549
Ala Phe Gln Gly His Gly Ala Gly Asn Leu Ala Gly Leu Lys Gly Arg
                135                 140                 145 ctc gat tac ctg agc tct ctg aag gtg aag ggc ctt gtg ctg ggt cca      597
Leu Asp Tyr Leu Ser Ser Leu Lys Val Lys Gly Leu Val Leu Gly Pro
            150                 155                 160 att cac aag aac cag aag gat gat gtc gct cag act gac ttg ctg cag      645
Ile His Lys Asn Gln Lys Asp Asp Val Ala Gln Thr Asp Leu Leu Gln
        165                 170                 175 atc gac ccc aat ttt ggc tcc aag gaa gat ttt gac agt ctc ttg caa      693
Ile Asp Pro Asn Phe Gly Ser Lys Glu Asp Phe Asp Ser Leu Leu Gln
    180                 185                 190 tcg gct aaa aaa aag agc atc cgt gtc att ctg gac ctt act ccc aac      741
Ser Ala Lys Lys Lys Ser Ile Arg Val Ile Leu Asp Leu Thr Pro Asn
195                 200                 205                 210 tac cgg ggt gag aac tcg tgg ttc tcc act cag gtt gac act gtg gcc      789
Tyr Arg Gly Glu Asn Ser Trp Phe Ser Thr Gln Val Asp Thr Val Ala
                215                 220                 225 acc aag gtg aag gat gct ctg gag ttt tgg ctg caa gct ggc gtg gat      837
Thr Lys Val Lys Asp Ala Leu Glu Phe Trp Leu Gln Ala Gly Val Asp
            230                 235                 240 ggg ttc cag gtt cgg gac ata gag aat ctg aag gat gca tcc tca ttc      885
Gly Phe Gln Val Arg Asp Ile Glu Asn Leu Lys Asp Ala Ser Ser Phe
        245                 250                 255
```

-continued

```
ttg gct gag tgg caa aat atc acc aag ggc ttc agt gaa gac agg ctc        933
Leu Ala Glu Trp Gln Asn Ile Thr Lys Gly Phe Ser Glu Asp Arg Leu
    260                 265                 270 ttg att gcg ggg act aac tcc tcc gac ctt cag cag atc ctg agc cta        981
Leu Ile Ala Gly Thr Asn Ser Ser Asp Leu Gln Gln Ile Leu Ser Leu
275                 280                 285                 290 ctc gaa tcc aac aaa gac ttg ctg ttg act agc tca tac ctg tct gat       1029
Leu Glu Ser Asn Lys Asp Leu Leu Leu Thr Ser Ser Tyr Leu Ser Asp
                295                 300                 305 tct ggt tct act ggg gag cat aca aaa tcc cta gtc aca cag tat ttg       1077
Ser Gly Ser Thr Gly Glu His Thr Lys Ser Leu Val Thr Gln Tyr Leu
            310                 315                 320 aat gcc act ggc aat cgc tgg tgc agc tgg agt ttg tct cag gca agg       1125
Asn Ala Thr Gly Asn Arg Trp Cys Ser Trp Ser Leu Ser Gln Ala Arg
        325                 330                 335 ctc ctg act tcc ttc ttg ccg gct caa ctt ctc cga ctc tac cag ctg       1173
Leu Leu Thr Ser Phe Leu Pro Ala Gln Leu Leu Arg Leu Tyr Gln Leu
    340                 345                 350 atg ctc ttc acc ctg cca ggg acc cct gtt ttc agc tac ggg gat gag       1221
Met Leu Phe Thr Leu Pro Gly Thr Pro Val Phe Ser Tyr Gly Asp Glu
355                 360                 365                 370 att ggc ctg gat gca gct gcc ctt cct gga cag cct atg gag gct cca       1269
Ile Gly Leu Asp Ala Ala Ala Leu Pro Gly Gln Pro Met Glu Ala Pro
                375                 380                 385 gtc atg ctg tgg gat gag tcc agc ttc cct gac atc cca ggg gct gta       1317
Val Met Leu Trp Asp Glu Ser Ser Phe Pro Asp Ile Pro Gly Ala Val
            390                 395                 400 agt gcc aac atg act gtg aag ggc cag agt gaa gac cct ggc tcc ctc       1365
Ser Ala Asn Met Thr Val Lys Gly Gln Ser Glu Asp Pro Gly Ser Leu
        405                 410                 415 ctt tcc ttg ttc cgg cgg ctg agt gac cag cgg agt aag gag cgc tcc       1413
Leu Ser Leu Phe Arg Arg Leu Ser Asp Gln Arg Ser Lys Glu Arg Ser
    420                 425                 430 cta ctg cat ggg gac ttc cac gcg ttc tcc gct ggg cct gga ctc ttc       1461
Leu Leu His Gly Asp Phe His Ala Phe Ser Ala Gly Pro Gly Leu Phe
435                 440                 445                 450 tcc tat atc cgc cac tgg gac cag aat gag cgt ttt ctg gta gtg ctt       1509
Ser Tyr Ile Arg His Trp Asp Gln Asn Glu Arg Phe Leu Val Val Leu
                455                 460                 465 aac ttt ggg gat gtg ggc ctc tcg gct gga ctg cag gcc tcc gac ctg       1557
Asn Phe Gly Asp Val Gly Leu Ser Ala Gly Leu Gln Ala Ser Asp Leu
            470                 475                 480 cct gcc agc gcc agc ctg cca gcc aag gct gac ctc ctc ctc agc acc       1605
Pro Ala Ser Ala Ser Leu Pro Ala Lys Ala Asp Leu Leu Leu Ser Thr
        485                 490                 495 cag cca ggc cgt gag gag ggc tcc cct ctt gag ctg gaa cgc ctg aaa       1653
Gln Pro Gly Arg Glu Glu Gly Ser Pro Leu Glu Leu Glu Arg Leu Lys
    500                 505                 510 ctg gag cct cac gaa ggg ctg ctc ctc cgc ttc ccc tac gcg gcc           1698
Leu Glu Pro His Glu Gly Leu Leu Leu Arg Phe Pro Tyr Ala Ala
515                 520                 525 tgacttcagc tgacatgga cccactaccc ttctcctttc cttcccaggc cctttggctt      1758 ctgattttc tctttttaa aaacaaacaa acaaactgtt gcagattatg agtgaacccc       1818
caaatagggt gttttctgcc ttcaaataaa gtcacccct gcatggtgaa gtcttccctc      1878
t                                                                     1879

<210> SEQ ID NO 66
<211> LENGTH: 529
<212> TYPE: PRT
```

<213> ORGANISM: Homo sapiens

<400> SEQUENCE: 66

```
Met Ser Gln Asp Thr Glu Val Asp Met Lys Glu Val Glu Leu Asn Glu
1               5                   10                  15

Leu Glu Pro Glu Lys Gln Pro Met Asn Ala Ala Ser Gly Ala Ala Met
            20                  25                  30

Ser Leu Ala Gly Ala Glu Lys Asn Gly Leu Val Lys Ile Lys Val Ala
        35                  40                  45

Glu Asp Glu Ala Glu Ala Ala Ala Ala Lys Phe Thr Gly Leu Ser
    50                  55                  60

Lys Glu Glu Leu Leu Lys Val Ala Gly Ser Pro Gly Trp Val Arg Thr
65                  70                  75                  80

Arg Trp Ala Leu Leu Leu Leu Phe Trp Leu Gly Trp Leu Gly Met Leu
                85                  90                  95

Ala Gly Ala Val Val Ile Ile Val Arg Ala Pro Arg Cys Arg Glu Leu
            100                 105                 110

Pro Ala Gln Lys Trp Trp His Thr Gly Ala Leu Tyr Arg Ile Gly Asp
        115                 120                 125

Leu Gln Ala Phe Gln Gly His Gly Ala Gly Asn Leu Ala Gly Leu Lys
    130                 135                 140

Gly Arg Leu Asp Tyr Leu Ser Ser Leu Lys Val Lys Gly Leu Val Leu
145                 150                 155                 160

Gly Pro Ile His Lys Asn Gln Lys Asp Val Ala Gln Thr Asp Leu
                165                 170                 175

Leu Gln Ile Asp Pro Asn Phe Gly Ser Lys Glu Asp Phe Asp Ser Leu
            180                 185                 190

Leu Gln Ser Ala Lys Lys Lys Ser Ile Arg Val Ile Leu Asp Leu Thr
        195                 200                 205

Pro Asn Tyr Arg Gly Glu Asn Ser Trp Phe Ser Thr Gln Val Asp Thr
    210                 215                 220

Val Ala Thr Lys Val Lys Asp Ala Leu Glu Phe Trp Leu Gln Ala Gly
225                 230                 235                 240

Val Asp Gly Phe Gln Val Arg Asp Ile Glu Asn Leu Lys Asp Ala Ser
                245                 250                 255

Ser Phe Leu Ala Glu Trp Gln Asn Ile Thr Lys Gly Phe Ser Glu Asp
            260                 265                 270

Arg Leu Leu Ile Ala Gly Thr Asn Ser Ser Asp Leu Gln Gln Ile Leu
        275                 280                 285

Ser Leu Leu Glu Ser Asn Lys Asp Leu Leu Leu Thr Ser Ser Tyr Leu
    290                 295                 300

Ser Asp Ser Gly Ser Thr Gly Glu His Thr Lys Ser Leu Val Thr Gln
305                 310                 315                 320

Tyr Leu Asn Ala Thr Gly Asn Arg Trp Cys Ser Trp Ser Leu Ser Gln
                325                 330                 335

Ala Arg Leu Leu Thr Ser Phe Leu Pro Ala Gln Leu Leu Arg Leu Tyr
            340                 345                 350

Gln Leu Met Leu Phe Thr Leu Pro Gly Thr Pro Val Phe Ser Tyr Gly
        355                 360                 365

Asp Glu Ile Gly Leu Asp Ala Ala Leu Pro Gly Gln Pro Met Glu
    370                 375                 380

Ala Pro Val Met Leu Trp Asp Glu Ser Ser Phe Pro Asp Ile Pro Gly
385                 390                 395                 400

Ala Val Ser Ala Asn Met Thr Val Lys Gly Gln Ser Glu Asp Pro Gly
```

```
                          405                 410                 415
Ser Leu Leu Ser Leu Phe Arg Arg Leu Ser Asp Gln Arg Ser Lys Glu
            420                 425                 430

Arg Ser Leu Leu His Gly Asp Phe His Ala Phe Ser Ala Gly Pro Gly
        435                 440                 445

Leu Phe Ser Tyr Ile Arg His Trp Asp Gln Asn Glu Arg Phe Leu Val
    450                 455                 460

Val Leu Asn Phe Gly Asp Val Gly Leu Ser Ala Gly Leu Gln Ala Ser
465                 470                 475                 480

Asp Leu Pro Ala Ser Ala Ser Leu Pro Ala Lys Ala Asp Leu Leu Leu
                485                 490                 495

Ser Thr Gln Pro Gly Arg Glu Glu Gly Ser Pro Leu Glu Leu Glu Arg
            500                 505                 510

Leu Lys Leu Glu Pro His Glu Gly Leu Leu Leu Arg Phe Pro Tyr Ala
        515                 520                 525

Ala

<210> SEQ ID NO 67
<211> LENGTH: 4539
<212> TYPE: DNA
<213> ORGANISM: Homo sapiens
<220> FEATURE:
<221> NAME/KEY: CDS
<222> LOCATION: (66)..(1586)

<400> SEQUENCE: 67
cggcgcgcac actgctcgct gggccgcggc tcccgggtgt cccaggcccg gccggtgcgc      60 agagc atg gcg ggt gcg ggc ccg aag cgg cgc gcg cta gcg gcg ccg gcg     110
      Met Ala Gly Ala Gly Pro Lys Arg Arg Ala Leu Ala Ala Pro Ala
      1               5                   10                  15 gcc gag gag aag gaa gag gcg cgg gag aag atg ctg gcc gcc aag agc     158
Ala Glu Glu Lys Glu Glu Ala Arg Glu Lys Met Leu Ala Ala Lys Ser
                20                  25                  30 gcg gac ggc tcg gcg ccg gca ggc gag ggc gag ggc gtg acc ctg cag     206
Ala Asp Gly Ser Ala Pro Ala Gly Glu Gly Glu Gly Val Thr Leu Gln
            35                  40                  45 cgg aac atc acg ctg ctc aac ggc gtg gcc atc atc gtg ggg acc att     254
Arg Asn Ile Thr Leu Leu Asn Gly Val Ala Ile Ile Val Gly Thr Ile
        50                  55                  60 atc ggc tcg ggc atc ttc gtg acg ccc acg ggc gtg ctc aag gag gca     302
Ile Gly Ser Gly Ile Phe Val Thr Pro Thr Gly Val Leu Lys Glu Ala
    65                  70                  75 ggc tcg ccg ggg ctg gcg ctg gtg gtg tgg gcc gcg tgc ggc gtc ttc     350
Gly Ser Pro Gly Leu Ala Leu Val Val Trp Ala Ala Cys Gly Val Phe
80                  85                  90                  95 tcc atc gtg ggc gcg ctc tgc tac gcg gag ctc ggc acc acc atc tcc     398
Ser Ile Val Gly Ala Leu Cys Tyr Ala Glu Leu Gly Thr Thr Ile Ser
                100                 105                 110 aaa tcg ggc ggc gac tac gcc tac atg ctg gag gtc tac ggc tcg ctg     446
Lys Ser Gly Gly Asp Tyr Ala Tyr Met Leu Glu Val Tyr Gly Ser Leu
            115                 120                 125 ccc gcc ttc ctc aag ctc tgg atc gag ctg ctc atc atc cgg cct tca     494
Pro Ala Phe Leu Lys Leu Trp Ile Glu Leu Leu Ile Ile Arg Pro Ser
        130                 135                 140 tcg cag tac atc gtg gcc ctg gtc ttc gcc acc tac ctg ctc aag ccg     542
Ser Gln Tyr Ile Val Ala Leu Val Phe Ala Thr Tyr Leu Leu Lys Pro
    145                 150                 155 ctc ttc ccc acc tgc ccg gtg ccc gag gag gca gcc aag ctc gtg gcc     590
Leu Phe Pro Thr Cys Pro Val Pro Glu Glu Ala Ala Lys Leu Val Ala
```

|  |  |  |  |  |  |  |  |  |  |  |  |  |  |  |  |
|---|---|---|---|---|---|---|---|---|---|---|---|---|---|---|---|
| 160 | | | | | 165 | | | | | 170 | | | | | 175 |

```
tgc ctc tgc gtg ctg ctg ctc acg gcc gtg aac tgc tac agc gtg aag            638
Cys Leu Cys Val Leu Leu Leu Thr Ala Val Asn Cys Tyr Ser Val Lys
                180                 185                 190 gcc gcc acc cgg gtc cag gat gcc ttt gcc gcc aag ctc ctg gcc                686
Ala Ala Thr Arg Val Gln Asp Ala Phe Ala Ala Lys Leu Leu Ala
        195                 200                 205 ctg gcc ctg atc atc ctg ctg ggc ttc gtc cag atc ggg aag ggt gat            734
Leu Ala Leu Ile Ile Leu Leu Gly Phe Val Gln Ile Gly Lys Gly Asp
            210                 215                 220 gtg tcc aat cta gat ccc aac ttc tca ttt gaa ggc acc aaa ctg gat            782
Val Ser Asn Leu Asp Pro Asn Phe Ser Phe Glu Gly Thr Lys Leu Asp
        225                 230                 235 gtg ggg aac att gtg ctg gca tta tac agc ggc ctc ttt gcc tat gga            830
Val Gly Asn Ile Val Leu Ala Leu Tyr Ser Gly Leu Phe Ala Tyr Gly
    240                 245                 250                 255 gga tgg aat tac ttg aat ttc gtc aca gag gaa atg atc aac ccc tac            878
Gly Trp Asn Tyr Leu Asn Phe Val Thr Glu Glu Met Ile Asn Pro Tyr
            260                 265                 270 aga aac ctg ccc ctg gcc atc atc atc tcc ctg ccc atc gtg acg ctg            926
Arg Asn Leu Pro Leu Ala Ile Ile Ile Ser Leu Pro Ile Val Thr Leu
        275                 280                 285 gtg tac gtg ctg acc aac ctg gcc tac ttc acc acc ctg tcc acc gag            974
Val Tyr Val Leu Thr Asn Leu Ala Tyr Phe Thr Thr Leu Ser Thr Glu
        290                 295                 300 cag atg ctg tcg tcc gag gcc gtg gcc gtg gac ttc ggg aac tat cac           1022
Gln Met Leu Ser Ser Glu Ala Val Ala Val Asp Phe Gly Asn Tyr His
    305                 310                 315 ctg ggc gtc atg tcc tgg atc atc ccc gtc ttc gtg ggc ctg tcc tgc           1070
Leu Gly Val Met Ser Trp Ile Ile Pro Val Phe Val Gly Leu Ser Cys
320                 325                 330                 335 ttc ggc tcc gtc aat ggg tcc ctg ttc aca tcc tcc agg ctc ttc ttc           1118
Phe Gly Ser Val Asn Gly Ser Leu Phe Thr Ser Ser Arg Leu Phe Phe
            340                 345                 350 gtg ggg tcc cgg gaa ggc cac ctg ccc tcc atc ctc tcc atg atc cac           1166
Val Gly Ser Arg Glu Gly His Leu Pro Ser Ile Leu Ser Met Ile His
        355                 360                 365 cca cag ctc ctc acc ccc gtg ccg tcc ctc gtg ttc acg tgt gtg atg           1214
Pro Gln Leu Leu Thr Pro Val Pro Ser Leu Val Phe Thr Cys Val Met
        370                 375                 380 acg ctg ctc tac gcc ttc tcc aag gac atc ttc tcc gtc atc aac ttc           1262
Thr Leu Leu Tyr Ala Phe Ser Lys Asp Ile Phe Ser Val Ile Asn Phe
385                 390                 395 ttc agc ttc ttc aac tgg ctc tgc gtg gcc ctg gcc atc atc ggc atg           1310
Phe Ser Phe Phe Asn Trp Leu Cys Val Ala Leu Ala Ile Ile Gly Met
400                 405                 410                 415 atc tgg ctg cgc cac aga aag cct gag ctt gag cgg ccc atc aag gtg           1358
Ile Trp Leu Arg His Arg Lys Pro Glu Leu Glu Arg Pro Ile Lys Val
                420                 425                 430 aac ctg gcc ctg cct gtg ttc ttc atc ctg gcc tgc ctc ttc ctg atc           1406
Asn Leu Ala Leu Pro Val Phe Phe Ile Leu Ala Cys Leu Phe Leu Ile
            435                 440                 445 gcc gtc tcc ttc tgg aag aca ccc gtg gag tgt ggc atc ggc ttc acc           1454
Ala Val Ser Phe Trp Lys Thr Pro Val Glu Cys Gly Ile Gly Phe Thr
        450                 455                 460 atc atc ctc agc ggg ctg ccc gtc tac ttc ttc ggg gtc tgg tgg aaa           1502
Ile Ile Leu Ser Gly Leu Pro Val Tyr Phe Phe Gly Val Trp Trp Lys
        465                 470                 475 aac aag ccc aag tgg ctc ctc cag ggc atc ttc tcc acg acc gtc ctg           1550
Asn Lys Pro Lys Trp Leu Leu Gln Gly Ile Phe Ser Thr Thr Val Leu
```

```
                480               485               490               495
tgt cag aag ctc atg cag gtg gtc ccc cag gag aca tagccaggag              1596
Cys Gln Lys Leu Met Gln Val Val Pro Gln Glu Thr
            500                       505 gccgagtggc tgccggagga gcatgcgcag aggccagtta agtagatca cctcctcgaa         1656 cccactccgg ttccccgcaa cccacagctc agctgcccat cccagtccct cgccgtccct        1716
cccaggtcgg gcagtggagg ctgctgtgaa aactctggta cgaatctcat ccctcaactg        1776
agggccaggg acccaggtgt gcctgtgctc ctgcccagga gcagcttttg gtctccttgg        1836
gccctttttc ccttccctcc tttgtttact tatatatata ttttttttaa acttaaattt        1896
tgggtcaact tgacaccact aagatgattt tttaaggagc tgggggaagg caggagcctt        1956
cctttctcct gccccaaggg cccagaccct gggcaaacag agctactgag acttggaacc        2016
tcattgctac gacagacttg cactgaagcc ggacagctgc ccagacacat gggcttgtga        2076
cattcgtgaa aaccaaccct gtgggcttat gtctctgcct tagggtttgc agagtggaaa       2136
ctcagccgta gggtggcact gggaggggt ggggatctg ggcaaggtgg gtgattcctc         2196
ccaggaggtg cttgaggccc cgatggactc ctgaccataa tcctagcccc gagacaccat       2256
cctgagccag ggaacagccc cagggttggg gggtgccggc atctccccta gctcaccagg       2316
cctggcctct gggcagtgtg gcctcttggc tatttctgtt ccagttttgg aggctgagtt       2376
ctggttcatg cagacaaagc cctgtccttc agtcttctag aaacagagac aagaaaggca       2436
gacacaccgc ggccaggcac ccatgtgggc gcccaccctg ggctccacac agcagtgtcc       2496
cctgccccag aggtcgcagc taccctcagc ctccaatgca ttggcctctg taccgcccgg      2556
cagccccttc tggccggtgc tgggttccca ctcccggcct aggcacctcc ccgctctccc       2616
tgtcacgctc atgtcctgtc ctggtcctga tgcccgttgt ctaggagaca gagccaagca       2676
ctgctcacgt ctctgccgcc tgcgtttgga ggccctggg ctctcaccca gtccccaccc        2736
gcctgcagag agggaactag ggcacccctt gtttctgttg ttcccgtgaa tttttttcgc       2796
tatgggaggc agccgaggcc tggccaatgc ggcccacttt cctgagctgt cgctgcctcc       2856
atggcagcag ccaaggaccc ccagaacaag aagacccccc cgcaggatcc ctcctgagct       2916
cggggggctc tgccttctca ggccccgggc ttcccttctc cccagccaga ggtggagcca       2976
agtggtccag cgtcactcca gtgctcagct gtggctggag gagctggcct gtggcacagc       3036
cctgagtgtc ccaagccggg agccaacgaa gccggacacg gcttcactga ccagcggctg      3096
ctcaagccgc aagctctcag caagtgccca gtggagcctg ccgcccccac ctgggcaccg       3156
ggaccccctc accatccagt gggcccggag aaacctgatg aacagtttgg ggactcagga      3216
ccagatgtcc gtctctcttg cttgaggaat gaagaccttt attcacccct gccccgttgc      3276
ttcccgctgc acatggacag acttcacagc gtctgctcat aggacctgca tccttcctgg      3336
ggacgaattc cactcgtcca agggacagcc cacggtctgg aggccgagga ccaccagcag      3396
gcaggtggac tgactgtgtt gggcaagacc tcttccctct gggcctgttc tcttggctgc      3456
aaataaggac agcagctggt gccccacctg cctggtgcat tgctgtgtga atccaggagg      3516
cagtggacat cgtaggcagc cacggccccg ggtccaggag aagtgctccc tggaggcacg     3576
caccactgct tcccactggg gccggcgggg cccacgcacg acgtcagcct cttaccttcc      3636
cgcctcggct aggggtcctc gggatgccgt tctgttccaa cctcctgctc tgggaggtgg     3696
acatgcctca aggatacagg gagccggcgg cctctcgacg gcacgcactt gcctgttggc      3756
tgctgcggct gtgggcgagc atgggggctg ccagcgtctg ttgtggaaag tagctgctag      3816
```

```
tgaaatggct ggggccgctg gggtccgtct tcacactgcg caggtctctt ctgggcgtct    3876
gagctggggt gggagctcct ccgcagaagg ttggtggggg gtccagtctg tgatccttgg    3936
tgctgtgtgc cccactccag cctggggacc ccacttcaga aggtaggggc cgtgtcccgc    3996
ggtgctgact gaggcctgct tcccctcccc cctcctgctg tgctggaatt ccacagggac    4056
cagggccacc gcagggact gtctcagaag acttgatttt tccgtcccctt tttctccaca    4116
ctccactgac aaacgtcccc agcggttttcc acttgtgggc ttcaggtgtt ttcaagcaca    4176
acccaccaca acaagcaagt gcattttcag tcgttgtgct tttttgtttt gtgctaacgt    4236
cttactaatt taaagatgct gtcggcacca tgtttattta tttccagtgg tcatgctcag    4296
ccttgctgct ctgcgtggcg caggtgccat gcctgctccc tgtctgtgtc ccagccacgc    4356
agggccatcc actgtgacgt cggccgacca ggctggacac cctctgccga gtaatgacgt    4416
gtgtggctgg gaccttcttt attctgtgtt aatggctaac ctgttacact gggctgggtt    4476
gggtagggtg ttctggcttt tttgtggggt ttttatttt aaagaaacac tcaatcatcc    4536
tag                                                                  4539
```

<210> SEQ ID NO 68
<211> LENGTH: 507
<212> TYPE: PRT
<213> ORGANISM: Homo sapiens

<400> SEQUENCE: 68

```
Met Ala Gly Ala Gly Pro Lys Arg Arg Ala Leu Ala Ala Pro Ala Ala
1               5                   10                  15

Glu Glu Lys Glu Glu Ala Arg Glu Lys Met Leu Ala Ala Lys Ser Ala
            20                  25                  30

Asp Gly Ser Ala Pro Ala Gly Glu Gly Glu Gly Val Thr Leu Gln Arg
        35                  40                  45

Asn Ile Thr Leu Leu Asn Gly Val Ala Ile Ile Val Gly Thr Ile Ile
    50                  55                  60

Gly Ser Gly Ile Phe Val Thr Pro Thr Gly Val Leu Lys Glu Ala Gly
65                  70                  75                  80

Ser Pro Gly Leu Ala Leu Val Val Trp Ala Ala Cys Gly Val Phe Ser
                85                  90                  95

Ile Val Gly Ala Leu Cys Tyr Ala Glu Leu Gly Thr Thr Ile Ser Lys
            100                 105                 110

Ser Gly Gly Asp Tyr Ala Tyr Met Leu Glu Val Tyr Gly Ser Leu Pro
        115                 120                 125

Ala Phe Leu Lys Leu Trp Ile Glu Leu Leu Ile Ile Arg Pro Ser Ser
    130                 135                 140

Gln Tyr Ile Val Ala Leu Val Phe Ala Thr Tyr Leu Leu Lys Pro Leu
145                 150                 155                 160

Phe Pro Thr Cys Pro Val Pro Glu Glu Ala Lys Leu Val Ala Cys
                165                 170                 175

Leu Cys Val Leu Leu Leu Thr Ala Val Asn Cys Tyr Ser Val Lys Ala
            180                 185                 190

Ala Thr Arg Val Gln Asp Ala Phe Ala Ala Lys Leu Leu Ala Leu
        195                 200                 205

Ala Leu Ile Ile Leu Leu Gly Phe Val Gln Ile Gly Lys Gly Asp Val
    210                 215                 220

Ser Asn Leu Asp Pro Asn Phe Ser Phe Glu Gly Thr Lys Leu Asp Val
225                 230                 235                 240

Gly Asn Ile Val Leu Ala Leu Tyr Ser Gly Leu Phe Ala Tyr Gly Gly
```

```
                    245                 250                 255
Trp Asn Tyr Leu Asn Phe Val Thr Glu Glu Met Ile Asn Pro Tyr Arg
            260                 265                 270

Asn Leu Pro Leu Ala Ile Ile Ile Ser Leu Pro Ile Val Thr Leu Val
            275                 280                 285

Tyr Val Leu Thr Asn Leu Ala Tyr Phe Thr Thr Leu Ser Thr Glu Gln
            290                 295                 300

Met Leu Ser Ser Glu Ala Val Ala Val Asp Phe Gly Asn Tyr His Leu
305                 310                 315                 320

Gly Val Met Ser Trp Ile Ile Pro Val Phe Val Gly Leu Ser Cys Phe
                325                 330                 335

Gly Ser Val Asn Gly Ser Leu Phe Thr Ser Ser Arg Leu Phe Phe Val
            340                 345                 350

Gly Ser Arg Glu Gly His Leu Pro Ser Ile Leu Ser Met Ile His Pro
            355                 360                 365

Gln Leu Leu Thr Pro Val Pro Ser Leu Val Phe Thr Cys Val Met Thr
            370                 375                 380

Leu Leu Tyr Ala Phe Ser Lys Asp Ile Phe Ser Val Ile Asn Phe Phe
385                 390                 395                 400

Ser Phe Phe Asn Trp Leu Cys Val Ala Leu Ala Ile Ile Gly Met Ile
                405                 410                 415

Trp Leu Arg His Arg Lys Pro Glu Leu Glu Arg Pro Ile Lys Val Asn
            420                 425                 430

Leu Ala Leu Pro Val Phe Phe Ile Leu Ala Cys Leu Phe Leu Ile Ala
            435                 440                 445

Val Ser Phe Trp Lys Thr Pro Val Glu Cys Gly Ile Gly Phe Thr Ile
450                 455                 460

Ile Leu Ser Gly Leu Pro Val Tyr Phe Phe Gly Val Trp Trp Lys Asn
465                 470                 475                 480

Lys Pro Lys Trp Leu Leu Gln Gly Ile Phe Ser Thr Thr Val Leu Cys
                485                 490                 495

Gln Lys Leu Met Gln Val Val Pro Gln Glu Thr
                500                 505

<210> SEQ ID NO 69
<211> LENGTH: 43
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: n is a, t, c or g.

<400> SEQUENCE: 69
tcagtatggt agctcacctn atttcacttt cggccctggg acc            43

<210> SEQ ID NO 70
<211> LENGTH: 43
<212> TYPE: DNA
<213> ORGANISM: Artificial
<220> FEATURE:
<223> OTHER INFORMATION: Oligonucleotide

<400> SEQUENCE: 70
tcagtatggt agctcacctb gtttcacttt cggccctggg acc            43

<210> SEQ ID NO 71
```

```
<211> LENGTH: 45
<212> TYPE: DNA
<213> ORGANISM: Artificial
<220> FEATURE:
<223> OTHER INFORMATION: Primer

<400> SEQUENCE: 71
ggtcccaggg ccgaaagtga atagaggtga gctaccatac tgctg          45

<210> SEQ ID NO 72
<211> LENGTH: 43
<212> TYPE: DNA
<213> ORGANISM: Artificial
<220> FEATURE:
<223> OTHER INFORMATION: Primer

<400> SEQUENCE: 72
gcagtatggt agctcacctc tattcacttt cggccctggg acc            43

<210> SEQ ID NO 73
<211> LENGTH: 42
<212> TYPE: DNA
<213> ORGANISM: Artificial
<220> FEATURE:
<223> OTHER INFORMATION: Primer

<400> SEQUENCE: 73
ccggaattca acactctccc ctgttgaagc tctttgtgac gg             42

<210> SEQ ID NO 74
<211> LENGTH: 45
<212> TYPE: DNA
<213> ORGANISM: Artificial
<220> FEATURE:
<223> OTHER INFORMATION: Primer

<400> SEQUENCE: 74
ggtcccaggg ccgaaagtga acataggtga gctaccatac tgctg          45

<210> SEQ ID NO 75
<211> LENGTH: 43
<212> TYPE: DNA
<213> ORGANISM: Artificial
<220> FEATURE:
<223> OTHER INFORMATION: Primer

<400> SEQUENCE: 75
gcagtatggt agctcaccta tgttcacttt cggccctggg acc            43

<210> SEQ ID NO 76
<211> LENGTH: 42
<212> TYPE: DNA
<213> ORGANISM: Artificial
<220> FEATURE:
<223> OTHER INFORMATION: Primer

<400> SEQUENCE: 76
ccggaattca acactctccc ctgttgaagc tctttgtgac gg             42

<210> SEQ ID NO 77
<211> LENGTH: 133
<212> TYPE: PRT
<213> ORGANISM: Artificial
<220> FEATURE:
<223> OTHER INFORMATION: L-chain variable region of antibody
      C2IgG1NS/117IL

<400> SEQUENCE: 77
```

```
Arg Ser Leu Thr Met Glu Thr Pro Ala Gln Leu Leu Phe Leu Leu Leu
 1               5                  10                  15

Leu Trp Leu Pro Asp Thr Thr Gly Glu Ile Val Leu Thr Gln Ser Pro
            20                  25                  30

Gly Thr Leu Ser Leu Ser Pro Gly Glu Arg Ala Thr Leu Ser Cys Arg
            35                  40                  45

Ala Ser Gln Ser Val Ser Ser Phe Leu Ala Trp Tyr Gln Gln Lys
     50                  55                  60

Pro Gly Gln Ala Pro Arg Leu Leu Ile Tyr Gly Ala Ser Ser Arg Ala
 65                  70                  75                  80

Thr Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys Gln Gln Tyr Gly Ser Ser Pro Leu Phe Thr Phe Gly Pro Gly Thr
            115                 120                 125

Lys Val Asp Ile Lys
            130
```

<210> SEQ ID NO 78
<211> LENGTH: 399
<212> TYPE: DNA
<213> ORGANISM: Artificial
<220> FEATURE:
<223> OTHER INFORMATION: L-chain variable region of antibody
      C2IgG1NS/117IL

<400> SEQUENCE: 78

```
agatctctca ccatggaaac cccagcgcag cttctcttcc tcctgctact ctggctccca    60
gataccaccg gagaaattgt gttgacgcag tctccaggca ccctgtcttt gtctccaggg   120
gaaagagcca ccctctcctg cagggccagt cagagtgtta gcagcagctt cttagcctgg   180
taccagcaga aacctggcca ggctcccagg ctcctcatct atggtgcatc cagcagggcc   240
actggcatcc cagacaggtt cagtggcagt gggtctggga cagacttcac tctcaccatc   300
agcagactgg agcctgaaga tttcgcagtg tattactgtc agcagtatgg tagctcacct   360
ctattcactt tcggccctgg gaccaaagtg gatatcaaa                           399
```

<210> SEQ ID NO 79
<211> LENGTH: 133
<212> TYPE: PRT
<213> ORGANISM: Artificial
<220> FEATURE:
<223> OTHER INFORMATION: L-chain variable region of antibody
      C2IgG1NS/117IM

<400> SEQUENCE: 79

```
Arg Ser Leu Thr Met Glu Thr Pro Ala Gln Leu Leu Phe Leu Leu Leu
 1               5                  10                  15

Leu Trp Leu Pro Asp Thr Thr Gly Glu Ile Val Leu Thr Gln Ser Pro
            20                  25                  30

Gly Thr Leu Ser Leu Ser Pro Gly Glu Arg Ala Thr Leu Ser Cys Arg
            35                  40                  45

Ala Ser Gln Ser Val Ser Ser Phe Leu Ala Trp Tyr Gln Gln Lys
     50                  55                  60

Pro Gly Gln Ala Pro Arg Leu Leu Ile Tyr Gly Ala Ser Ser Arg Ala
 65                  70                  75                  80

Thr Gly Ile Pro Asp Arg Phe Ser Gly Ser Gly Ser Gly Thr Asp Phe
```

```
                   85                  90                  95
Thr Leu Thr Ile Ser Arg Leu Glu Pro Glu Asp Phe Ala Val Tyr Tyr
            100                 105                 110

Cys Gln Gln Tyr Gly Ser Ser Pro Met Phe Thr Phe Gly Pro Gly Thr
            115                 120                 125

Lys Val Asp Ile Lys
    130

<210> SEQ ID NO 80
<211> LENGTH: 399
<212> TYPE: DNA
<213> ORGANISM: Artificial
<220> FEATURE:
<223> OTHER INFORMATION: L-chain variable region of antibody
      C2IgG1NS/117IM

<400> SEQUENCE: 80
agatctctca ccatggaaac cccagcgcag cttctcttcc tcctgctact ctggctccca    60
gataccaccg gagaaattgt gttgacgcag tctccaggca ccctgtcttt gtctccaggg   120
gaaagagcca ccctctcctg cagggccagt cagagtgtta gcagcagctt cttagcctgg   180
taccagcaga aacctggcca ggctcccagg ctcctcatct atggtgcatc cagcagggcc   240
actggcatcc cagacaggtt cagtggcagt gggtctggga cagacttcac tctcaccatc   300
agcagactgg agcctgaaga tttcgcagtg tattactgtc agcagtatgg tagctcacct   360
atgttcactt tcggccctgg gaccaaagtg gatatcaaa                          399

<210> SEQ ID NO 81
<211> LENGTH: 133
<212> TYPE: PRT
<213> ORGANISM: Artificial
<220> FEATURE:
<223> OTHER INFORMATION: L-chain variable region of antibody
      C2IgG1NS/117IN

<400> SEQUENCE: 81

Arg Ser Leu Thr Met Glu Thr Pro Ala Gln Leu Leu Phe Leu Leu Leu
1               5                   10                  15

Leu Trp Leu Pro Asp Thr Thr Gly Glu Ile Val Leu Thr Gln Ser Pro
            20                  25                  30

Gly Thr Leu Ser Leu Ser Pro Gly Glu Arg Ala Thr Leu Ser Cys Arg
            35                  40                  45

Ala Ser Gln Ser Val Ser Ser Phe Leu Ala Trp Tyr Gln Gln Lys
        50                  55                  60

Pro Gly Gln Ala Pro Arg Leu Leu Ile Tyr Gly Ala Ser Ser Arg Ala
65                  70                  75                  80

Thr Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys Gln Gln Tyr Gly Ser Ser Pro Asn Phe Thr Phe Gly Pro Gly Thr
            115                 120                 125

Lys Val Asp Ile Lys
    130

<210> SEQ ID NO 82
<211> LENGTH: 399
<212> TYPE: DNA
<213> ORGANISM: Artificial
<220> FEATURE:
```

<223> OTHER INFORMATION: L-chain variable region of antibody
C2IgG1NS/117IN

<400> SEQUENCE: 82

```
agatctctca ccatggaaac cccagcgcag cttctcttcc tcctgctact ctggctccca      60
gataccaccg gagaaattgt gttgacgcag tctccaggca ccctgtcttt gtctccaggg     120
gaaagagcca ccctctcctg cagggccagt cagagtgtta gcagcagctt cttagcctgg     180
taccagcaga aacctggcca ggctcccagg ctcctcatct atggtgcatc cagcagggcc     240
actggcatcc cagacaggtt cagtggcagt gggtctggga cagacttcac tctcaccatc     300
agcagactgg agcctgaaga tttcgcagtg tattactgtc agcagtatgg tagctcacct     360
aatttcactt tcggccctgg gaccaaagtg gatatcaaa                            399
```

<210> SEQ ID NO 83
<211> LENGTH: 133
<212> TYPE: PRT
<213> ORGANISM: Artificial
<220> FEATURE:
<223> OTHER INFORMATION: L-chain variable region of antibody
C2IgG1NS/117IC

<400> SEQUENCE: 83

```
Arg Ser Leu Thr Met Glu Thr Pro Ala Gln Leu Leu Phe Leu Leu Leu
1               5                   10                  15

Leu Trp Leu Pro Asp Thr Thr Gly Glu Ile Val Leu Thr Gln Ser Pro
                20                  25                  30

Gly Thr Leu Ser Leu Ser Pro Gly Glu Arg Ala Thr Leu Ser Cys Arg
            35                  40                  45

Ala Ser Gln Ser Val Ser Ser Phe Leu Ala Trp Tyr Gln Gln Lys
        50                  55                  60

Pro Gly Gln Ala Pro Arg Leu Leu Ile Tyr Gly Ala Ser Ser Arg Ala
65                  70                  75                  80

Thr Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
                100                 105                 110

Cys Gln Gln Tyr Gly Ser Ser Pro Cys Phe Thr Phe Gly Pro Gly Thr
            115                 120                 125

Lys Val Asp Ile Lys
            130
```

<210> SEQ ID NO 84
<211> LENGTH: 399
<212> TYPE: DNA
<213> ORGANISM: Artificial
<220> FEATURE:
<223> OTHER INFORMATION: L-chain variable region of antibody
C2IgG1NS/117IC

<400> SEQUENCE: 84

```
agatctctca ccatggaaac cccagcgcag cttctcttcc tcctgctact ctggctccca      60
gataccaccg gagaaattgt gttgacgcag tctccaggca ccctgtcttt gtctccaggg     120
gaaagagcca ccctctcctg cagggccagt cagagtgtta gcagcagctt cttagcctgg     180
taccagcaga aacctggcca ggctcccagg ctcctcatct atggtgcatc cagcagggcc     240
actggcatcc cagacaggtt cagtggcagt gggtctggga cagacttcac tctcaccatc     300
agcagactgg agcctgaaga tttcgcagtg tattactgtc agcagtatgg tagctcacct     360
```

-continued

```
tgtttcactt tcggccctgg gaccaaagtg gatatcaaa                      399

<210> SEQ ID NO 85
<211> LENGTH: 35
<212> TYPE: DNA
<213> ORGANISM: Artificial
<220> FEATURE:
<223> OTHER INFORMATION: Oligonucleotide

<400> SEQUENCE: 85
ccgcgagacc caccettgga ggctccagat ttatc                          35
```

The invention claimed is:

1. A human monoclonal antibody or a functional fragment thereof that binds CD98 and that has any, pair of sequences of the following (b) to (g) as a heavy chain variable region and a light chain variable region:
    (b) SEQ ID NOs: 41 and 47,
    (c) SEQ ID NOs: 43 and 47,
    (d) SEQ ID NOs: 43 and 77,
    (e) SEQ ID NOs: 43 and 79,
    (f) SEQ ID NOs: 43 and 81, and
    (g) SEQ ID NOs: 43 and 83,
    wherein said functional fragment is selected from the group consisting of Fab, Fab', (Fab')2, Fv, scFv, and sdFv of said antibody and a combination thereof.

2. The human monoclonal antibody or a functional fragment thereof according to claim 1, wherein a subclass of the antibody heavy chain constant region is IgG.

3. A conjugate, comprising:
    (i) the human monoclonal antibody or a functional fragment thereof according to any one of claim 1 or claim 2; and (ii) a heterogeneous domain containing a binding protein, an enzyme, a drug, a toxin, an immunomodulator, a detectable portion or a tag.

4. A cell expressing the human monoclonal antibody or a functional fragment thereof according to any one of claims 1 or 2.

5. A pharmaceutical composition comprising the human monoclonal antibody or a functional fragment thereof according to any one of claims 1 or 2 as an active ingredient.

6. A therapeutic agent for colorectal cancer or colon cancer comprising the human monoclonal antibody or a functional fragment thereof according to any one of claims 1 or 2 as an active ingredient.

7. A method for producing an antibody that binds CD98, comprising:
    introducing to a host cell an expression vector containing any pair of sequences of the following (b) to (g):
    (b) SEQ ID NOs: 40 and 46,
    (c) SEQ ID NOs: 42 and 46,
    (d) SEQ ID NOs: 42 and 78,
    (e) SEQ ID NOs: 42 and 80,
    (f) SEQ ID NOs: 42 and 82, and
    (g) SEQ ID NOs: 42 and 84,
    or a degenerate nucleotide sequence thereof; then culturing the host cell to produce a culture; and obtaining the antibody from the culture.

8. The method according to claim 7, wherein the host cell is selected from the group consisting of *E. coli*, yeast cells, insect cells, mammal cells, and plant cells.

* * * * *